United States Patent
Austin et al.

(10) Patent No.: US 10,603,313 B2
(45) Date of Patent: Mar. 31, 2020

(54) ALLOSTERIC MODULATORS OF THE MU OPIOID RECEPTOR

(71) Applicant: Chiromics, LLC, Princeton, NJ (US)

(72) Inventors: Joel Francis Austin, West Windsor, NJ (US); Michael David VanHeyst, Morrisville, PA (US); James S. Harvey, Brookline, MA (US); Elizabeth Gerig Rowley, Kendall Park, NJ (US); Christophe Lamarque-Lacoste, Princeton, NJ (US)

(73) Assignee: CHIROMICS, LLC, Princeton, NJ (US)

( * ) Notice: Subject to any disclaimer, the term of this patent is extended or adjusted under 35 U.S.C. 154(b) by 0 days.

(21) Appl. No.: 16/048,051

(22) Filed: Jul. 27, 2018

(65) Prior Publication Data

US 2019/0030020 A1    Jan. 31, 2019

Related U.S. Application Data

(60) Provisional application No. 62/605,106, filed on Jul. 31, 2017.

(51) Int. Cl.
| | |
|---|---|
| *A61K 31/451* | (2006.01) |
| *A61K 31/4545* | (2006.01) |
| *A61K 38/07* | (2006.01) |
| *A61P 25/04* | (2006.01) |
| *C07D 401/06* | (2006.01) |
| *C07D 401/04* | (2006.01) |
| *A61K 31/439* | (2006.01) |
| *C07D 401/12* | (2006.01) |
| *C07D 211/96* | (2006.01) |
| *C07D 401/14* | (2006.01) |
| *C07D 221/22* | (2006.01) |
| *A61K 31/506* | (2006.01) |
| *A61K 38/17* | (2006.01) |
| *C07D 209/52* | (2006.01) |
| *C07D 207/48* | (2006.01) |

(52) U.S. Cl.
CPC ........ *A61K 31/4545* (2013.01); *A61K 31/439* (2013.01); *A61K 31/506* (2013.01); *A61K 38/07* (2013.01); *A61K 38/1787* (2013.01); *A61P 25/04* (2018.01); *C07D 207/48* (2013.01); *C07D 209/52* (2013.01); *C07D 211/96* (2013.01); *C07D 221/22* (2013.01); *C07D 401/04* (2013.01); *C07D 401/06* (2013.01); *C07D 401/12* (2013.01); *C07D 401/14* (2013.01)

(58) Field of Classification Search
CPC ... A61K 31/451; A61K 31/506; C07D 471/04
USPC ......... 514/256, 318; 544/326, 328; 546/192, 546/194
See application file for complete search history.

(56) References Cited

FOREIGN PATENT DOCUMENTS

| WO | WO2000058285 | * 10/2000 | .......... C07D 207/48 |
|---|---|---|---|
| WO | 2014107344 A1 | 7/2014 | |

OTHER PUBLICATIONS

Bartuzi, D., Kaczor, A. & Matosiuk, D., 2016. Interplay between Two Allosteric Sites and their influence on agonist binding in human mu opioid receptor. J Chem Inf Model, vol. 56, pp. 563-570.

Bartuzi, D., Kaczor, A. & Matosiuk, D., 2019. Molecular mechanisms of allosteric probe dependence in mu-opiod receptor. Journal of Biomolecular Structure and Dynamics, 37(1), pp. 36-47.

Bisgano, P. et al., 2015. Ligand-Based Discovery of a New Scaffold for Allosteric Modulation of the μ-Opioid Receptor. Journal of Chemical Information and Modeling, vol. 55, pp. 1836-1843.

Burford, N. et al., 2013. Discovery of positive allosteric modulators and silent allosteric modulators of the mu-opioid receptor. Proceedings of the National Academy of Sciences: USA, 110(26), pp. 10830-10835.

Burford, N. et al., 2015. Discovery, Synthesis, and Molecular Pharmacology of Selective Positive Allosteric Modulators of the δ-Opioid Receptor. Journal of Medicinal Chemistry, vol. 58, pp. 4220-4229.

Burford, N., Traynor, J. & Alt, A., 2015. Positive allosteric modulators of the mu-opioid receptor: a novel approach for ruture pain medications. The British Pharmacological Society, vol. 172, pp. 277-286.

Bushlin, I., Gupta, A., Stockton, S. & Miller, L. D. L., 2012. Dimerization with cannabinoid receptors allosterically modulates delta opioid receptor activity during neuropathic pain. PLos One, p. e49789.

Filizola, M., 2019. Insights from molecular dynamics simulations to exploit new trends for the development of improved opioid drugs. Neuroscience Letters, vol. 700, pp. 50-55.

Gunther, T. D. P. et al., 2018. Targeting multiple opioid receptors—improved analgesics with reduced side effects?. British Journal of Pharmacology, 175(14), pp. 2857-2868.

Kathman, M. et al., 2006. Cannabidiol is an allosteric modulator at the mu- and delta-opioid receptors. Naunyn-Schmiedeberg's Arch. Pharmacol., 372(5), pp. 354-361.

Livingston, K. & Traynor, J., 2014. Disruption of the Na+ ion binding site as a mechanism for positive allosteric modulation of the mu-opioid receptor. Proceedings of the National Academy of Sciences, 111(51), pp. 18369-18374.

Livingston, K. & Traynor, J., 2018. Allostery at the opioid receptors: Modulation with small molecule ligands. British Journal of Pharmacology, 175(14), pp. 2846-2856.

(Continued)

*Primary Examiner* — Jeffrey H Murray

(74) *Attorney, Agent, or Firm* — Brennan IP Services

(57) ABSTRACT

Disclosed herein are compounds, of the class of amine-bearing heterocycles, which act as positive allosteric modulators and silent allosteric modulators of the mu opioid receptor. These compounds are useful for the treatment of pain, drug addiction, and other CNS derived maladies that are controlled directly or indirectly by activation of the mu opioid receptor. Methods for making and using the allosteric modulators disclosed herein are also provided.

20 Claims, 20 Drawing Sheets

(56) References Cited

OTHER PUBLICATIONS

Livingston, K. et al., 2018. Measuring ligand efficacy at the mu-opioid receptor using a conformational biosensor. Elife, p. e32499.

Livingston, K. et al., 2018. Pharmacologic evidence for a putative conserved allosteric site on opioid receptors. Molecular Pharmacology, 93(2), pp. 157-167.

Munro, T. et al., 2013. Studies toward bivalent k-opioids derived from salvinorin A: Heteromethylation of the furan ring reduces affinity. Beilstein Journal of Organic Chemistry, vol. 9, pp. 2916-2924.

Nickols, H. & Conn, P., 2014. Development of allosteric modulators of GPCRs for treatment of CNS disorders. Neurobiology of Disease, vol. 61, pp. 55-71.

Noble, F., Lenoir, M. & Marie, N., 2015. The Opioid receptors as targets for drug abuse medication. British Journal of Pharmacology, 172(16), pp. 3964-3979.

Ohbuchi, K M. C. S. Y. et al., 2016. Ignavine: A novel allosteric modulator of the mu-opioid receptor. Scientific Reports, vol. 6, p. 31748.

Remesic, M., Hruby, V., Porreca, F. & Lee, Y., 2017. Recent Advances in the Realm of Allosteric Modulators for Opioid Receptors for Future Therapeutics. ACS Chemical Neuroscience, vol. 8, pp. 1147-1158.

Rockwell, K. & Alt, A., 2017. Positive Allosteric Modulators of Opioid Receptors. In: Allosterism in Drug Discovery. London: Royal Society of Chemistry, pp. 194-219.

Rothman, R. et al., 2007. Salvinorin A: Allosteric interactions at the mu-opioid receptor. Journal of Pharmacology and Experimental Therapeutics, 320(2), pp. 801-810.

Shang, Y. & Filizola, M., 2015. Opioid receptors: Structural and mechanistic insights into pharmacology and signaling. European Journal of Pharmacology, 763(B), pp. 206-213.

Shang, Y. et al., 2016. Proposed mode of binding and action of positive allosteric modulators at the opioid receptors. ACS Chemical Biology, 11(5), pp. 1220-1229.

Shim, J., Coop, A. & MacKerell, A., 2011. Consensus 3D model of the mu-opioid receptor ligand efficacy based on a quantitative conformationally sampled pharmacophore. Journal of Physical Chemistry B, 115(22), pp. 7487-7496.

ISA/US, International Search Report and Written Opinion for PCT/US18/061866, dated Mar. 18, 2019, 17 pages.

* cited by examiner

ALLOSTERIC MODULATORS OF THE MU OPIOID RECEPTOR

CROSS REFERENCE TO RELATED APPLICATIONS

This application claims the benefit, under 35 U.S.C. § 119(e)(1), of U.S. Provisional Application No. 62/605,106 filed on Jul. 31, 2017; the disclosure of which is hereby incorporated by reference, in its entirety, for all purposes.

FIELD

The present application is in the field of receptor biology; in particular, opioid receptors and allosteric modulators thereof.

BACKGROUND

The superfamily of G protein-coupled receptors (GPCRs) comprises plasma membrane spanning proteins that transduce signals via heterotrimeric G proteins on the inner surface of the plasma membrane, leading to intracellular signaling cascades. Jacoby et al. (2006) *ChemMedChem* 1:761-782. The cell surface location, tissue distribution, and diversity of these GPCRs make them ideal targets for drug intervention. It is widely reported that roughly 30% of marketed drugs target specific GPCR activity. Jacoby, E. B. (2006), supra; Overington et al. (2006) *Nature Reviews Drug. Disc.* 5:993-996.

The Opioid Receptors (ORs) are members of the Class A family of GPCRs. As such, ORs mediate the actions of endogenous opioids (e.g., endorphins) as well as the action of exogenous opioids such as morphine and morphine-like opiates, including most clinical analgesics. Four OR types are known to exist: the mu OR, the delta OR, the kappa OR and the L1OR; respectively abbreviated as MOR, DOR, KOR, ORL1. These OR subtypes appear to have overlapping functional mechanisms at a cellular level, share roughly 60% amino acid identity, and signal through the Gi/o family of heterotrimeric G proteins. The signaling pathways of opioid receptors are well characterized. Stein & Machelska (2011) *Pharmacological Reviews* 63:860-881.

After binding of an orthosteric ligand, conformational changes in the receptor allow intracellular coupling of heterotrimeric Gi/o proteins to the C terminus of the receptor. At the Gα subunit, GTP replaces GDP and dissociation of the trimeric G protein complex into Gα and Gβγ subunits ensues. Subsequently, these subunits can inhibit adenylyl cyclases and thereby reduce cAMP production and/or directly interact with different ion channels in the membrane.

The different OR types appear to share many functional mechanisms at the cellular level. The activation and/or inactivation of the ORs by endogenous or exogenous orthosteric opioids results in inhibition of adenylyl cyclase, modulation of ion channel activity, and transcriptional changes in the cell. Waldhoer et al. (2004) *Annual Review of Biochemistry* 73:953-990. For example, activation of the mu opioid receptors causes inhibition of adenylate cyclase (resulting in lower intracellular cAMP levels), and recruits β-arrestin to the receptor. β-arrestin recruitment is a non-G-protein mediated signaling pathway through which many GPCRs (including the ORs) signal. Evidence exists that β-arrestin is involved in receptor desensitization and internalization/recycling. Whalen, E. R. (2011) *Trends in Molecular Medicine* 17:126-139; Shukla et al. (2011) *Trends in Biomedical Sciences* 36:457-469.

ORs are key targets in the management of pain, with morphine and its derivatives inducing pain relief by acting as full or partial receptor agonists. Pain relief (analgesia) is attributed to the actions of opiates and opioids specifically at MOR. Matthes et al. (1996) *Nature* 383:819-823; Manglik et al. (2012) *Nature* 485:321-326. When therapeutic doses of morphine are given to patients with pain, the patients report that the pain is less intense, less discomforting, or entirely absent. However, in addition to providing relief of distress, the narrow therapeutic window for morphine also clinically manifests a variety of adverse side effects. Moreover, when a pain-relieving dose of morphine is administered to a pain-free individual, the experience is not always pleasant; nausea is common, and vomiting may also occur. In addition, drowsiness, inability to concentrate, difficulty in mentation, apathy, lessened physical activity, reduced visual acuity, and lethargy may ensue.

Two highly selective MOR agonists, endomorphin-1 (EM1) and endomorphin-2 (EM2), have been isolated from bovine as well as human brains in large quantities and are believed to be the endogenous ligands for the MOR. Zadina et al. (1997) *Nature* 386:499-502; Hackler et al. (1993) *Neuropeptides* 24:159-164; Erchegyi et al. (1992) *Peptides* 13:623-631. Relative to other orthosteric agonists, EM1 and EM2 display an exceptionally high level of binding affinity and selectivity for MOR over KOR and DOR. Zadina et al. (1994) *Life Sciences* 55:461-466. The differential distribution of these peptides in various tissues has been widely studied with results indicating that EM1 is more densely distributed throughout the brain; whereas EM2 is more prevalent in the spinal cord. Martin-Schild et al. (1999) *J Comp. Neurol.* 405:450-471. Additionally, the presence of the endomorphins (EMs) and MOR has been confirmed in animal and human models of inflammatory and neuropathic pain. Troung et al. (2003) *Ann. Neurol.* 53:366-375; Straub et al. (2008) *Arthritis and Rheumatism* 58:456-466; Yang et al. (2014) *PLOS ONE* 9(2):e89583; Stein et al. (1993) *Lancet* 342:321-324; Mousa et al. (2002) *J. Neuroimmunol.* 126:5-15; McDougall et al. (2004) *Am. J. Physiol. Regul. Integr. Comp. Physiol.* 286:R634-R641; Obara et al. (2004) *Neuroscience Letters* 360:85-89. The antinociceptive actions of exogenously administered EM1 and EM2 have been studied in a variety of animal models, as well as in humans. Soigner et al. (2000) *Life Sciences* 67:907-912; Horvath et al. (1999) *Life Sciences* 65:2635-2641; Macdougall et al. (2004) *J. Molec. Neurosci.* 22:125-137; Horvath (2000) *Pharmacology & Therapeutics* 88:437-463; Przewlocka et al. (1999a) *Eur. J Pharmacol.* 367:189-196; Przewlocka et al. (1999b) *Ann NY Acad. Sci.* 897:154-164.

Opioid receptors have been extensively studied because of the needs for (1) better pain control and (2) reduction or elimination of adverse side effects. The side effects common to orthosteric ligands for the opioid receptors include, in addition to those mentioned above, tolerance, respiratory suppression, constipation, allodynia, and dependence. Waldhoer et al., supra; McNicol et al. (2003) *J. Pain* 4:231-256. Indeed, recent determinations of the therapeutic indices for commonly used opioids led to the conclusion that systemic side effects are to be expected for all of them (Kuo et al. (2015) *British J. Pharmacol.* 172:532-548), leading some to conclude that the side effects are mechanism-based. Alternatively, the side effects of opioid use could be attributed to the signal bias that these orthosteric ligands induce and/or to the presence of receptors and/or their ligands in tissues that are not experiencing pain. Kenakin (2015a) *Trends Pharmacol. Sci.* 36:705-706; Stein & Machelska, supra.

To overcome the side effects associated with traditional OR orthosteric agonists and partial agonists, drug discovery efforts have focused on (1) developing selective orthosteric ligands which display OR subtype selectivity either as full agonists, partial agonists or when used in combination therapy (Davis (2012) *Exp. Opin. Drug Discov.* 7:165-178; Dietis (2009) *Br. J. Anaesth.* 103:38-49); (2) physiological compartmentalization of orthosteric ligands (Spahn et al. (2017) *Science* 355:966-969); and (3) inducing selective signal bias of orthosteric ligands (Soergel et al. (2014) *Pain* 155:1829-1835; Chen et al. (2013) *J. Medicinal Chem.* 56:8019-8031). These diverse approaches have in common a strategy in which the orthosteric ligand binding domain is the only entity being probed and/or modified. Given the current national epidemic of orthosteric opioid agonist abuse, a novel approach to pain mitigation would provide a welcome benefit to society. Lauren & Rossen (2016) Drug Poisoning Mortality: United States, 2002-2014. Atlanta: National Center for Health Statistics, Centers for Disease Control and Prevention.

Allosteric modulators of opioid receptors provide an alternative strategy for pain mitigation. An allosteric modulator has no intrinsic agonist or antagonist activity toward a receptor but, in the presence of an orthosteric agonist, can further increase the activity of the receptor beyond that induced by the orthosteric agonist (a positive allosteric modulator, or PAM) or decrease receptor activity below that which would normally be induced by the orthosteric agonist (a negative allosteric modulator, or NAM). Thus, the use of positive allosteric modulators of the μ-opioid receptor (MOR PAMS or MOR-PAMs), when used in conjunction with exogenous opioids, would allow lower doses of opioid to be administered, thereby lessening side effects and potential for abuse.

In addition, because endogenous MOR agonists are not distributed throughout the entire body, but tend to be released in areas experiencing pain, the use of a MOR PAM as an analgesic (in the absence of an exogenous opioid) also has the advantage that the body of the subject is not being flooded with an exogenous opioid. Rather, the MOR-PAM activates the receptor only in the regions of the body that already contain endogenous receptor agonists; thereby potentiating the activity of the agonist and activating the receptor only in the regions where necessary for pain reduction.

The naturally-occurring hallucinogen Salvinorin A has been observed to behave, in vitro, as an allosteric modulator of the MOR. Rothman (2007) *J. Pharmacol. Exp. Therapeutics* 320:801-810. However, further use of this compound for in vivo mechanistic testing and/or therapeutic use is unlikely due to its inherent polypharmacology.

Thiazolidine-based allosteric modulators of the MOR have also been described and tested in vitro. WO 2014/107344; Burford et al. (2011) *Biochemical Pharmacol.* 81:691-702; Burford et al. (2013) *Proc. Natl. Acad. Sci. USA* 110:10830-10835; Burford et al. (2015) *Br. J. Pharmacol.* 172:277-286; Livingston et al. (2014) *Proc. Natl. Acad. Sci. USA* 111:18369-18374. However, in vitro analyses of these compounds have revealed that they are unlikely to be useful for in vivo studies and routine therapeutic use, because of the difficulty of their synthesis, poor potency and metabolic instability. Some of these compounds also possess pure agonist activity in addition to PAM activity in certain assays (i.e., they act as "ago-PAMs") and therefore lack the benefit of being able to amplify endogenous analgesic mechanisms in a temporally- and spatially-limited fashion. (Bisignano et al. (2015) *J. Chem. Inf. Model* 55:1836-1843; Rockwell & Alt (2017) "Positive Allosteric Modulators of Opioid Receptors" in *RSC Drug Discovery Series No. 56: Allosterism in Drug Discovery*, ed. D. Doller, Royal Society of Chemistry, Chapter 9, pp. 194-219; Livingston et al., supra.

Modification of these thiazolidine-based MOR PAMs, guided by structure/activity relationship (SAR)-based lead optimization, and attendant pharmacophore modeling, have been conducted. (Bisignano et al. (2015) *J. Chem. Inf. Model* 55:1836-1843; Bartuzi et al. (2016) *J. Chem. Inf. Model* 56:563-570. These efforts have also not yielded potent or selective compounds viable for in vivo testing. In addition, the SAR-based derivatives are somewhat non-specific, showing some PAM activity at the delta opioid receptor as well. Rockwell & Alt, supra.

For all of the foregoing reasons, there is a need for new compounds that induce OR signaling and analgesia, but have reduced side effects, and that are suitable for in vivo testing and administration. There is a continuing need for new analgesics that can incorporate the profound beneficial effects of opioids without the concomitant side effects; and for compounds that can potentiate the temporally- and spatially-restricted activity of endogenous opioids.

SUMMARY

Disclosed herein are compositions that act as positive allosteric modulators (PAMs) of mu opioid receptor-mediated signal transduction, methods for their synthesis, and methods for their use in providing analgesia with minimal side effects. For inducing analgesia, PAMs can be administered by themselves to augment the activity of endogenous opioids such as the endomorphins. Alternatively, PAMs can be administered in combination with an exogenous opioid such as, for example, morphine, oxycodone or fentanyl. In these embodiments, a MOR PAM can be administered at the same time (i.e., together with) an exogenous opioid, or the MOR PAM and the exogenous opioid can be administered at different times. If administered at different times, administration or the MOR PAM can precede administration of the exogenous opioid, or administration of the exogenous opioid can precede administration of the MOR PAM.

In certain embodiments, compounds disclosed herein act as positive allosteric modulators (PAMs) of the mu opioid receptor (MOR). By itself, a PAM bound to the receptor has no effect on receptor activity. However, when the MOR is bound by both a PAM as disclosed herein and an orthosteric ligand (endogenous or exogenous); the signaling activity of the MOR is greater than when it is bound by an orthosteric ligand alone. Endogenous orthosteric MOR ligands include endomorphin-1 (EM1); endomorphin-2 (EM2), the enkephalins (e.g., Leu-Enk and Met-Enk, which also bind the delta- and kappa-opioid receptors) and β-endorphin (which also bind the delta- and kappa-opioid receptors). Exogenous orthosteric MOR ligands include, for example, morphine, morphine-6-glucuronide, fentanyl, oxycontin, oxycodone, hydrocodone, DAMGO, herkinorn, loperamide, buprenorphine, etorphine, methadone, naloxone, Oxymorphone hydrazine, [D-penicillamine 2,5]-enkephalin (DPDE), Hydromorphone, Dihydromorphine, Codeine, Oxymorphol, and Oxymorphone.

In certain embodiments, the compounds disclosed herein potentiate the activity of endomorphin-1 (EM1) on the mu opioid receptor. In additional embodiments, the compounds disclosed herein potentiate the activity of endomorphin-2 (EM2) on the mu opioid receptor.

MOR signaling can be measured by methods that are known in the art including, but not limited to, recruitment of beta-arrestin to the receptor, inhibition of adenylate cyclase activity (resulting in lowering of intracellular cAMP levels in the receptor cell), phosphorylation of extracellular signal-related kinases 1 and 2 (ERK1/2; also known as mitogen-activated protein kinase, MAPK) and G-protein activation (which involves a conformational change in the receptor that allows exchange of bound GDP for GTP).

Thus, in certain embodiments, MOR PAMs as disclosed herein augment one or more of beta-arrestin-1/2 recruitment, inhibition of adenylate cyclase activity, phosphorylation of ERK1/2 and G-protein activation.

In certain embodiments, MOR PAMs as disclosed herein selectively modulate the activity of the mu opioid receptor, as compared to the delta, kappa, or ORL1 opioid receptors. In additional embodiments, MOR-PAMs as disclosed herein specifically potentiate the activity of endomorphin-1 on the MOR, compared to other orthosteric ligands of the MOR. In additional embodiments, MOR-PAMs as disclosed herein specifically potentiate the activity of endomorphin-2 on the MOR, compared to other orthosteric ligands of the MOR.

Certain of the PAMs disclosed herein exhibit selective signal bias on G-protein-mediated downstream signaling activities; i.e., they affect a particular downstream process (e.g., cAMP signaling) more strongly than other downstream processes (e.g., β-arrestin recruitment, GTP/GDP exchange, ERK phosphorylation). Selective signal bias is beneficial, for example, for cases in which a particular downstream signaling system contributes to the side effects of an opioid rather than to its analgesic effect (e.g., β-arrestin recruitment).

Also provided are compositions that act as silent allosteric modulators (SAMs) of mu opioid receptor-mediated signal transduction, methods for their synthesis, and methods for their use. Thus, in certain embodiments, compounds disclosed herein act as silent allosteric modulators (SAMs) of the mu opioid receptor (MOR). A SAM binds to a site on the receptor that is identical to, or overlapping with, the site bound by a PAM; however, binding of the SAM has no effect on the activity (agonistic or antagonistic) of the orthosteric ligand. Although a SAM cannot directly affect the activity of an orthosteric ligand, it can modulate the effect of a PAM on the orthosteric ligand, by competing with the PAM for binding to the receptor. Thus, for example, a SAM can be used, in combination with a PAM, to fine-tune the modulatory effect of the PAM.

Accordingly, in additional embodiments for the use of MOR PAMs, the MOR PAM is administered together with a MOR SAM and optionally an exogenous opioid. Administration of the MOR PAM and the MOR SAM can be conducted at the same time or at different times. If administered at different times, administration of the MOR PAM can precede administration of the MOR SAM, or administration of the MOR SAM can precede administration of the MOR PAM. Administration of the MOR PAM and/or the MOR SAM can either precede or follow administration of the exogenous opioid, or administration of the MOR PAM and/or the MOR SAM can occur simultaneously with the administration of the exogenous opioid.

Also provided are methods of treating pain in a subject in need thereof by administering to the subject a MOR PAM as disclosed herein. In additional embodiments, methods of treating pain in a subject comprise administering to the subject a MOR PAM as disclosed herein in conjunction with a MOR SAM as disclosed herein. The MOR PAM and/or MOR PAM/MOR SAM combination can be administered before or during the onset of pain and, upon the release of endogenous opioids (e.g., EM1), the presence of the MOR PAM in the subject increases the intensity and/or duration of the native pain-relieving mechanism.

In additional embodiments, methods of treating pain in a subject comprise administering to the subject an orthosteric ligand of an opioid receptor in conjunction with a MOR PAM as disclosed herein. In further embodiments, methods of treating pain in a subject comprise administering to the subject an orthosteric ligand of an opioid receptor in conjunction with both a PAM as disclosed herein and a SAM as disclosed herein. In certain embodiments, the opioid receptor is the MOR. In additional embodiments, the orthosteric agonist is, for example, morphine, oxycodone or fentanyl.

Also provided are methods for inducing analgesia in a subject in need thereof, by administering to the subject a MOR PAM as disclosed herein. In additional embodiments, methods of inducing analgesia in a subject comprise administering to the subject a MOR PAM as disclosed herein in conjunction with a MOR SAM as disclosed herein. The MOR PAM and/or MOR PAM/MOR SAM combination can be administered before or during the onset of pain and, upon the release of endogenous opioids (e.g., EM1), the presence of the MOR PAM in the subject increases the intensity and/or duration of native analgesic mechanisms.

In additional embodiments, methods of inducing analgesia in a subject comprise administering to the subject an orthosteric ligand of an opioid receptor in conjunction with a MOR PAM as disclosed herein. In further embodiments, methods of inducing analgesia in a subject comprise administering to the subject an orthosteric ligand of an opioid receptor in conjunction with both a PAM as disclosed herein and a SAM as disclosed herein. In certain embodiments, the opioid receptor is the MOR. In additional embodiments, the orthosteric agonist is, for example, morphine, oxycodone or fentanyl.

Also provided are methods for reducing nociception in a subject in need thereof, by administering to the subject a MOR PAM as disclosed herein. In additional embodiments, methods of reducing nociception in a subject comprise administering to the subject a MOR PAM as disclosed herein in conjunction with a MOR SAM as disclosed herein. The MOR PAM and/or MOR PAM/MOR SAM combination can be administered before or during the onset of pain and, upon the release of endogenous opioids (e.g., EM1), the presence of the MOR PAM in the subject reduces the intensity and/or duration of nociception.

In additional embodiments, methods of reducing nociception in a subject comprise administering to the subject an orthosteric ligand of an opioid receptor in conjunction with a MOR PAM as disclosed herein. In further embodiments, methods of reducing nociception in a subject comprise administering to the subject an orthosteric ligand of an opioid receptor in conjunction with both a PAM as disclosed herein and a SAM as disclosed herein. In certain embodiments, the opioid receptor is the MOR. In additional embodiments, the orthosteric agonist is, for example, morphine, oxycodone or fentanyl.

In certain embodiments for the use of a MOR-PAM (optionally in combination with a MOR-SAM) to treat pain, induce analgesia and/or reduce nociception; the MOR-PAM (optionally in combination with a MOR-SAM) is administered together with exogenously-administered (e.g., synthetic) EM1 or EM2 (e.g., Cyt-1010, Cytogel Pharma, Darien Conn.). See, for example, U.S. Pat. Nos. 5,885,958; 6,303,578 and 8,716,436.

Also provided are methods for potentiating the effect of an exogenous opioid administered to a subject by co-administering, with the exogenous opioid, a MOR PAM as disclosed herein and/or a MOR SAM as disclosed herein. In certain embodiments, a reduced dose of the exogenous opioid is co-administered with the PAM or PAM/SAM combination. The MOR PAM can be administered prior to, at the same time as, or subsequent to, administration of the exogenous opioid. The MOR SAM can be administered prior to, at the same time as, or subsequent to, administration of the exogenous opioid and/or the MOR PAM.

In additional embodiments, methods for reducing the side effects of an opioid are provided. In these methods, the opioid (e.g., morphine, oxycodone, fentantyl, etc.) is administered at a lower-than-normal dose (i.e., a sub-therapeutic dose), in combination with a MOR PAM as disclosed herein and/or a MOR PAM as disclosed herein and a MOR SAM as disclosed herein. The MOR PAM can be administered prior to, at the same time as, or subsequent to, administration of the exogenous opioid. The MOR SAM can be administered prior to, at the same time as, or subsequent to, administration of the exogenous opioid and/or the MOR PAM. In certain embodiments, the MOR PAM possesses selective signal bias; e.g., toward adenylyl cyclase inhibition and away from β-arrestin recruitment.

The MOR PAM compounds disclosed herein can be used to treat acute or chronic pain arising from any type of disorder including, but not limited to, inflammation, blunt force, cancer, neuropathy, burns, surgery, hormonal or endocrine imbalances, and viral, fungal and/or bacterial insults. A partial but not exhaustive list of therapeutic uses for such compounds includes treatment of pain, immune dysfunction, inflammation, esophageal reflux, neurological and psychiatric conditions, medicaments for drug and alcohol abuse, agents for treating gastritis and diarrhea, cardiovascular agents and/or agents for the treatment of respiratory diseases and cough.

The MOR PAM compounds disclosed herein can also be used to treat non-pain disorders arising from conditions of known and unknown etiology that have physiological connections to endogenous circulating endorphin levels. These include but are not limited to any type of hormonal or endocrine imbalances which can affect an individual. A partial but not exhaustive list of therapeutic uses for such compounds includes treatment of anxiety, depression, stress, urological and reproductive conditions, and sexual dysfunction.

In the methods of use disclosed herein, the MOR PAM compounds can be administered to a subject by any means known in the art including, for example, injection, transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, or by oral administration.

Also provided are pharmaceutical compositions comprising a MOR PAM compound as disclosed herein and a pharmaceutically acceptable excipient.

Also provided are MOR PAM compounds as disclosed herein for use in reducing pain, inducing analgesia, or reducing nociception in a subject.

Also provided are uses of MOR PAM compounds as disclosed herein in methods for reducing pain, inducing analgesia, or reducing nociception in a subject.

Also provided are uses of MOR PAM compounds as disclosed herein in the manufacture of a medicament for reducing pain, inducing analgesia, or reducing nociception in a subject.

Also provided are kits for use in reducing pain, inducing analgesia, or reducing nociception in a subject, wherein the kits comprise one or more MOR PAM compounds as disclosed herein, optionally in combination with a pharmaceutically acceptable excipient and/or packaging or container(s) and/or instruction for use.

Also provided are pharmaceutical compositions comprising a MOR SAM compound as disclosed herein and a pharmaceutically acceptable excipient.

Also provided are MOR SAM compounds as disclosed herein for use in reducing pain, inducing analgesia, or reducing nociception in a subject.

Also provided are uses of MOR SAM compounds as disclosed herein in methods for reducing pain, inducing analgesia, or reducing nociception in a subject.

Also provided are uses of MOR SAM compounds as disclosed herein in the manufacture of a medicament for reducing pain, inducing analgesia, or reducing nociception in a subject.

Also provided are kits for use in reducing pain, inducing analgesia, or reducing nociception in a subject, wherein the kits comprise one or more MOR SAM compounds as disclosed herein, optionally in combination with a pharmaceutically acceptable excipient and/or packaging or container(s) and/or instruction for use.

Also provided are methods for making positive allosteric modulators and silent allosteric modulators of opioid receptors. These methods are described elsewhere in this specification.

(15 mg/kg, + symbol, and 30 mg/kg, circles) on the antinociceptive effect of a sub-effecaceous dose of intrathecally administered exogenous EM1 (1 µg, diamonds) in the tail-flick assay. Effects of administration of an equal volume of saline, and of administration of 3 µg (triangles) and 10 µg (squares) of EM1 are shown for comparison.

Figure 13:
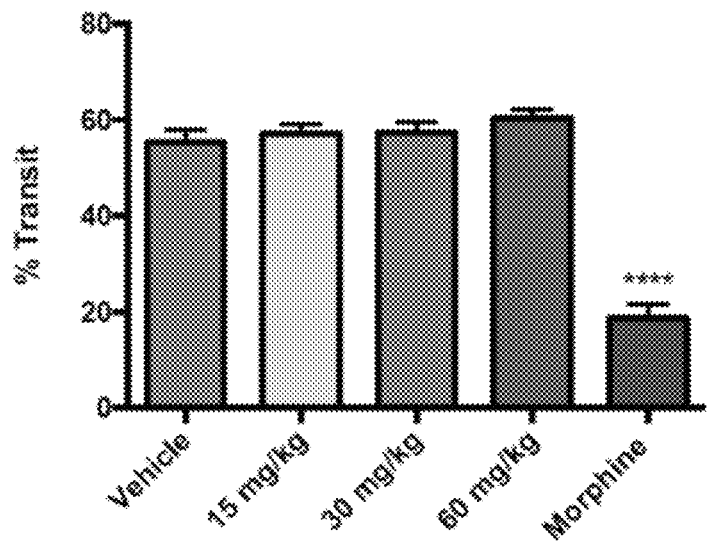

FIG. 13 shows effects of compound 9 (at 15, 30 and 60 mg/kg body weight) on gastrointestinal transit of charcoal through rat small intestine. Effects of no compound (vehicle) and morphine were also determined.

Figure 14:
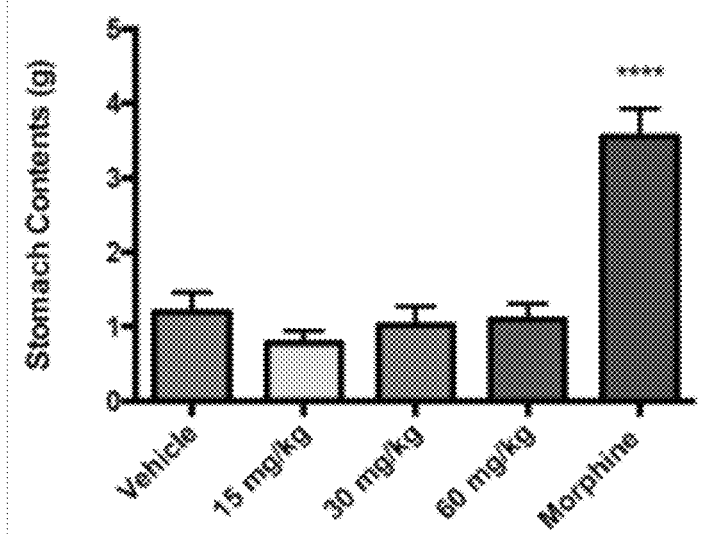

FIG. 14 shows effects of compound 9 (at 15, 30 and 60 mg/kg body weight) on amount of charcoal remaining in rat stomach 20 minutes after administration by lavage. Effects of no compound (vehicle) and morphine were also determined.

Figure 15:
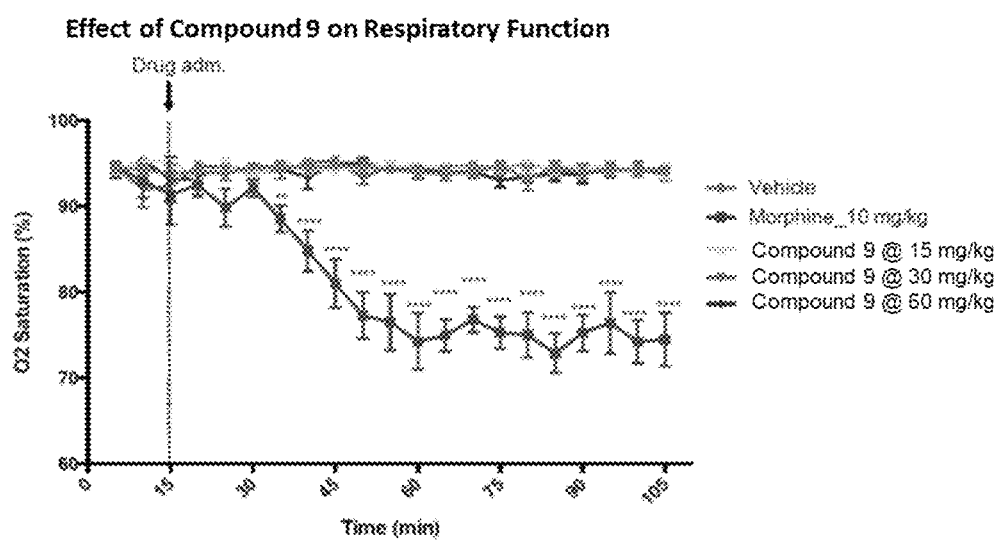

FIG. 15 shows oxygen saturation, measured by pulse oximetry, in rats treated with compound 9 (at 15, 30 and 60 mg/kg body weight). Also shown are effects of morphine and vehicle.

DETAILED DESCRIPTION

Practice of the present disclosure employs, unless otherwise indicated, standard methods and conventional techniques in the fields of organic chemistry, synthetic chemistry, biochemistry, pharmacology, cell biology, toxicology, molecular biology, cell culture, recombinant DNA and related fields as are within the skill of the art. Such techniques are described in the literature and thereby available to those of skill in the art.

Unless otherwise defined, all technical and scientific terms used herein have the same meaning as commonly understood by one of ordinary skill in the art. Although methods and materials similar or equivalent to those described herein can be used in the practice or testing of the compositions and compounds described herein, suitable methods and materials are described herein.

All publications, patent applications, patents, and other references mentioned herein are incorporated by reference in their entireties. In addition, the materials, methods, and examples are illustrative only, and not intended to be limiting. Other features and advantages of the compositions and compounds described herein will be apparent from the following detailed description and claims.

Disclosed herein are compounds that act as of MOR PAMs and MOR SAMs. The MOR PAMs and MOR SAMs disclosed herein function with respect to both endogenous MOR ligands (e.g., EM-1 and EM-2) and a variety of non-endogenous orthosteric ligands (e.g., morphine, oxycodone, fentanyl, loperamide). Certain of the MOR PAMs and MOR SAMs disclosed herein exhibit selective signal bias; that is, they influence certain ligand-induced MOR downstream signaling activities more strongly than others. For example, certain MOR PAMs have a stronger effect on adenylyl cyclase inhibition than on β-arrestin recruitment. Since β-arrestin recruitment is believed to contribute more strongly to the side effects experienced with the use of non-endogenous opioids, MOR PAMs with selective signal bias toward adenylyl cyclase inhibition (and away from β-arrestin recruitment) provide improved therapeutics for use in analgesia and pain management.

In the absence of EM1 (an endogenous MOR ligand), the MOR PAMs disclosed herein show neither agonist nor antagonist activity in assays for MOR activation (described elsewhere herein), thus demonstrating a pure PAM mechanism. MOR PAMs, as disclosed herein, demonstrated a left shift in a Schild-regression analysis of EM1, demonstrating that they have an impact on alpha, beta and tau-B values for the endogenous ligand endomorphin-1 Kenakin & Willilams (2014) *Biochem. Pharmacol.* 87:40-63. Certain of the MOR PAMs disclosed herein were demonstrated to have no PAM activity against DOR and KOR subtypes, thus demonstrating a level of selectivity difficult to achieve with orthosteric ligands.

The MOR PAMs disclosed herein are selective for the endogenous orthosteric ligands EM1 and EM2, but some also retain activity for non-natural orthosteric ligands such as oxycodone. For example, certain of the MOR PAMS disclosed herein demonstrated a left shift in a Schild-regression analysis for the non-endogenous ligand oxycodone, demonstrating that they are having an impact on alpha, beta and tau-B values. This unexpected result demonstrates the versatility of the MOR PAM approach for identifying therapeutically relevant compounds. Unlike previously identified MOR PAMs, compounds described herein show animal pharmacokinetic properties that demonstrate suitability for in vivo testing. Finally, the compounds described herein affect the efficacy and duration of analgesic effect in an animal model of acute pain.

Use of the MOR PAMs described herein for pain management combines the concepts of allosteric ligands and selective signal bias. Allosteric ligands for a GPCR bind to a site on the receptor that is distinct from the orthosteric site to which endogenous ligands bind. Burford et al. (2011) supra; Kenakin (2009) *Trends Pharmacol Sci.* 30:460-469. An allosteric modulator (AM) can exhibit a range of activities at the target protein by affecting a multitude of processes; such as, but not limited to, the binding affinity of ligands at the orthosteric site, the dissociative off rate of ligands that bind to the orthosteric site, the form of the 7 transmembrane domain (7TM) protein available for binding orthosteric ligands, and/or the form of the 7TM protein which transfers signals from the extracellular to the intracellular compartment. Positive allosteric modulators (PAMs) can increase the affinity ($\beta$) and/or the efficacy ($\alpha$) of agonists and there are therapeutic settings in which it is advantageous to distinguish between these mechanisms of action. For instance, in cases in which a failing physiological system must be revitalized, only efficacy effects ($\alpha>1$) will be beneficial; however, for cases in which enhancement of a normally functioning system is required, either $\alpha$ or $\beta$ effects will suffice and, in general, molecules can be characterized with the $\alpha\beta$ product parameter. The positive allosteric modulators (PAMs) described herein have no intrinsic agonist activity, but when bound to the receptor in concert with an orthosteric ligand (endogenous or otherwise), they enhance the binding affinity or efficacy (or both) of an orthosteric agonist or partial agonist. The silent allosteric modulators (SAMs) described have no intrinsic agonist activity, but when they bind to the receptor in concert with an orthosteric ligand (endogenous or otherwise) they can interfere with the binding of PAMS; thereby acting as competitive antagonists by blocking the activity of the PAM.

Allosteric ligands have the potential to exhibit greater selectivity, compared with orthosteric ligands, between subtypes of GPCRs in the same family. This has been demonstrated for some GPCRs including metabotropic glutamate receptors, adenosine receptors, and muscarinic receptors. Birdsall (2005) *Mini Reviews in Medicinal Chemistry* 5:523-543; Bruns & Fergus (1990) *Mol. Pharmacol.* 38:939-949; Conn et al. (2009) *Trends Pharmacol. Sci.* 30:148-155; Gao et al. (2005) *Mini Reviews in Medicinal Chemistry* 5:545-553; Harrington et al. (2010) *Bioorganic & Medicinal Chemistry Letters* 20:5544-5547. This increased selectivity is hypothesized to be based on the evolutionary constraint placed on the orthosteric site between closely related receptor subtypes that bind the same endogenous orthosteric ligand. This evolutionary constraint may not be required for allosteric sites. Positive allosteric modulators of the calcium-sensing receptor have been identified and shown to be clinically relevant in the maintenance of cellular calcium concentrations. Harrington et al., supra.

There is data that indicates that the continuous availability of endogenous opioids in inflamed tissue increases recycling and preserves signaling of MOR in sensory neurons. This is thought to counteract the development of peripheral opioid tolerance. Consequently, the use of peripherally acting opioids for the prolonged treatment of inflammatory pain (optionally in combination with MOR-PAMs and/or MOR SAMs as described herein) may not necessarily lead to opioid tolerance. Zollner et al. (2008) *J. Clin. Investig.* 118:1065-1073.

While highly selective orthosteric agonist ligands exist for the opioid receptor subtypes, the PAMs described herein provide additional advantages. PAMs, unlike allosteric agonists, may have no effect when they bind to the receptor in the absence of an orthosteric agonist. Therefore, the modulation occurs only when an orthosteric agonist is bound to the receptor. In vivo, this leads to preservation of the temporal and spatial characteristics of cell signaling and analgesic responses mediated by endogenous orthosteric agonists; which is important, especially for signaling in the complex neuronal networks in the brain and enteric nervous system. Additionally, by preserving the temporal and spatial aspects of native receptor signaling, the use of PAMs helps avoid receptor down-regulation and other compensatory mechanisms that are triggered by sustained receptor activation produced by exogenous orthosteric agonists. Zollner et al., supra.

In contrast to the use of a MOR PAM to potentiate the temporal and spatially-limited activity of endogenous orthosteric agonists as described above; exogenous orthosteric agonists have the capability to activate desired and undesired receptors in desired and undesired tissues for an extended period of time, thereby resulting in off-target effects.

In response to pain, both humans and rodents produce ORs at the site of injury with concomitant endogenous opioid ligand trafficking occurring through a number of different mechanisms. Przewlocki et al. (1992) *Neuroscience* 48:491-500; Rittner et al. (2001) *Anesthesiology* 95:500-508; Mousa et al., supra; Martin-Schild et al., supra; Li et al. (2005) *Arthritis and Rheumatism* 52: 3210-3219; Straub, et al., supra. Long-term systemic dosing with opiates is known, in some cases, to lead to the development of tolerance and dependence; as well as other acute receptor-mediated side-effects such as respiratory suppression, constipation and allodynia. Waldhoer et al., supra; McNicol et al., supra.

Thus, PAMs as disclosed herein, which have probe dependency for endogenous opioid agonists, take advantage of the body's natural pain response mechanisms, acting primarily when the body is in pain, and thus retaining the temporal benefits of endogenous pain relief. By contrast, the use of traditional agonist ligands results in receptor activation for long time periods (based on the dosing regime), often resulting in adverse effects, such as desensitization of the receptor response or receptor-mediated side-effects caused by long-term stimulation. The use of MOR PAMS, as disclosed herein, reduces this long-term receptor stimulation, by increasing the efficacy of the agonist effect of the orthosteric ligand. Consequently, opioid receptor PAMs are expected to produce less tolerance and dependence than exogenous orthosteric agonists (Zollner et al., supra); leading to reduced abuse potential of PAMs compared to that of orthosteric ligands Another advantage of the PAMs disclosed herein is their ability to increase the potency of an orthosteric agonist (as manifested by a left-shift in the concentration response curve) by a finite amount. Burford et al. (2015), supra. This finite potency shift allows the design of PAMs that cannot exceed a required level of effect; thereby improving safety.

It has been well documented in both humans (Stein et al. (1993), supra; Troung et al., supra) and non-humans (Borzsei (2008) *Neuroscience* 152:82-88) that there is a temporally-regulated production of opioid receptors in peripheral tissue in response to pain. Additionally, it is documented that endogenous ligands of the opioid receptors are released upon painful stimuli in animal models. Mousa et al., supra; Martin-Schild et al., supra; Yang et al., supra. The discovery and development of the PAMs disclosed herein which augment the efficacy, potency, duration of action, etc. of native and non-native ligands for the ORs represents a significant advance in the state of modern drug discovery and pain management.

Assays for Ligand Binding and Opioid Receptor Activity

A "natural ligand-induced activity" as used herein, refers to activation of the MOR by endomorphin-1, enodomophin-2 or other endogenously produced peptides. A "non-natural ligand-induced activity" as used herein, refers to activation of the MOR by morphine, oxycodone, fentanyl or other non-endogenously produced opiates. Activity can be assessed using any number of endpoints to measure OR activity. Generally, assays for testing compounds that modulate MOR-mediated signal transduction, either by natural or non-natural ligand-induced activity, include the determination of any parameter that is directly or indirectly under the influence of an OR, e.g., a functional, physical, or chemical effect. Examples of functional effects include GTP/GDP exchange at the receptor, phosphorylation of ERK, recruitment of β-arrestin (either or both of β-arrestin 1 or β-arrestin 2) to the receptor, inhibition of adenylyl cyclase (leading to lowering of intracellular cAMP levels), and displacement of probes (e.g., radiolabeled) already bound to the receptor. Examples of physical effects include conformational changes in the receptor, changes in the affinity and/or specificity of ligand binding, effects on receptor dimerization (homodimerizatoin or heterodimerization), effects on receptor trimerization (homotrimerizatoin or heterotrimerization), receptor degradation and receptor translocation. Examples of chemical effects include effects on availability of hydrogen-bonding networks in the active site. Samples or assays comprising ORs that are treated with a potential activator, inhibitor, or modulator are compared to control samples without the inhibitor, activator, or modulator to examine the extent of activation, inhibition or modulation.

The effects of the compounds described herein, upon the function of an OR, can be measured by examining any of the parameters described above. Any suitable physiological change that affects OR activity can be used to assess the influence of a compound on an OR and on natural or non-natural ligand-mediated OR activity. When the functional consequences are determined using intact cells or animals, it is also possible to measure a variety of effects such as changes in the levels of intracellular second messengers such as cAMP.

Modulators of OR activity are tested using OR polypeptides as described above (e.g., mu OR, kappa OR, delta OR and ORL1), either recombinant or naturally occurring. The protein can be isolated, expressed in a cell, expressed in a membrane derived from a cell, expressed in tissue or expressed in an animal. For example, neuronal cells, cells of the immune system, transformed cells, or membranes can be used to test the GPCR polypeptides described herein. Modulation is tested using an in vitro or in vivo assay, as described herein or known in the art. Signal transduction can be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Furthermore, ligand-binding domains of a protein of interest can be used in vitro in soluble or solid state reactions to assay for ligand binding.

Ligand binding to an OR, an OR domain, or a chimeric protein can be tested in a number of formats. Binding can be performed in solution, in a bilayer membrane, attached to a solid phase, in a lipid monolayer, or in vesicles. In certain of the assays described herein, the binding of the natural ligand to its receptor is measured in the presence of a candidate modulator. Alternatively, the binding of a candidate modulator can be measured in the presence of the natural ligand. Competitive assays that measure the ability of a compound to compete with binding of the natural ligand to the receptor can be used. Competitive assays that measure the ability of a compound to compete with the binding of a positive allosteric modulator (PAM) can also be used, e.g., to identify potential silent allosteric modulators (SAMs). Binding can be tested by measuring, e.g., changes in spectroscopic characteristics (e.g., fluorescence, absorbance, refractive index), hydrodynamic (e.g., shape) changes, or changes in chromatographic or solubility properties.

Modulators can also be identified using assays involving beta-arrestin recruitment. β-arrestin is a protein that is distributed throughout the cytoplasm in unactivated cells. Ligand binding to an appropriate OR results in redistribution of β-arrestin from the cytoplasm to the cell surface, where it associates with the OR. Thus, receptor activation and the effect of candidate modulators on ligand-induced receptor activation, can be assessed by monitoring β-arrestin recruitment to the cell surface.

Other assays for MOR activation are known in the art. See, for example, WO 2012/129495.

Compounds

The MOR PAMs and MOR SAMs provided herein are compounds having the structure:

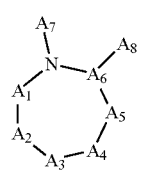

Formula 1

Wherein

A1 is null, $CH_2$, $CHR_1$, $CR_2R_3$, CH, $CR_4$, CO, O, S, SO, $SO_2$, NH or $NR_5$;

A2 is null, $CH_2$, $CHR_6$, $CR_7R_8$, CH, $CR_9$, CO, O, S, SO, $SO_2$, NH or $NR_{10}$;

A3 is null, $CH_2$, $CHR_{11}$, $CR_{12}R_{13}$, CH, $CR_{14}$, CO, O, S, SO, $SO_2$, NH, $NR_{15}$;

A4 is null, $CH_2$, $CHR_{16}$, $CR_{17}R_{18}$, CH, $CR_{19}$, CO, O, S, SO, $SO_2$, NH, $NR_{20}$;

A5 is null, $CH_2$, $CHR_{21}$, $CR_{22}R_{23}$, CH, $CR_{24}$, CO, O, SO, $SO_2$, NH, $NR_{25}$;

A6 is CH or $CR_{26}$;

A7 is $SO_2R_{27}$, $SOR_{28}$, $CHR_{29}$, $R_{30}$, $CH_2R_{31}$, $COR_{32}$, $CONHR_{33}$, $CONR_{34}R_{35}$, alkyl, branched alkyl, substituted alkyl, aryl, substituted aryl, cyclic, substituted cyclic, heterocyclic, substituted heterocyclic, heteroaryl, substituted heteroaryl or a small substitution group;

A8 is alkyl, branched alkyl, substituted alkyl, aryl, substituted aryl, cyclic, substituted cyclic, heterocyclic, substituted heterocyclic, heteroaryl, substituted heteroaryl, biaryl, substituted biaryl, heterobiaryl, substituted heterobiaryl or a small substitution group; and R1 through R35 are independently alkyl, branched alkyl, halogenated alkyl, branched halogenated alkyl, branched alkylcarbonyl, halogenated alkylcarbonyl, branched halogenated alkylcarbonyl, arylcarbonyl alkenyl, substituted alkenyl, alkynyl, ether or a small substitution group; further wherein no more than 4 of A1-A5 are null.

In certain embodiments, one or more of the hydrogen atoms attached to A1, A2, A3, A4, A5 or A6 can be replaced with a deuterium (D) atom.

No more than two heteroatoms (e.g., O, N, S) can be present within A1-A4; and O—O, S—O, S—S and S—N bonds within A1 through A6 are excluded.

In certain embodiments, any one or more of A7, A8 or R1-R35 are a small substitution group, selected from cyano, halogen, lower alkyl (e.g., C1-C3 alkyl), branched lower alkyl (e.g., isopropyl), halogenated alkyl, hydroxyl, oxyalkyl, alkyloxy, amino, alkylamino, dialkylamino, mercaptanyl, alkylmercaptanyl, alkylsulfonyl, aminosulfonyl, alkylaminosulfonyl, alkylcarbonyl, alkoxycarbonyl, aminocarbonyl, alkylaminocarbonyl, dialkylaminocarbonyl, aryl, arylalkyl, carbocycle, carbocycle-alkyl, F, Cl, Br, $CH_3$, $CH_2CH_3$, $CH_2F$, $CHF_2$, $CF_3$, n-Pr, n-Bu, i-Bu, sec-Bu, iPr, t-Bu, CN, OH, OMe, OEt, O-iPr, $OCF_2H$, $OCF_3$, $NH_2$, NHMe, $NMe_2$, methoxycarbonyl, methanesulfonyl, phenyl, benzyl, $MeSO_2$, formyl or acetyl.

Any one or more of the bonds between N and A1, A1 and A2, A2 and A3, A3 and A4, A4 and A5, A5 and A6, and A6 and N can be a double bond, provided that the distribution of double bonds in the molecule results in a stable structure.

In certain embodiments, the compound of Formula I is a six-membered, nitrogen-containing ring (i.e., a piperidine ring) with substituents A7 and A8.

In certain embodiments, the compound of Formula I is a four, five, six or seven-membered ring that is fused to a second ring, forming a spirocycle, a bridged bicycle or a fused bicycle.

In certain of the bicyclic compounds provided herein a spirocyclic bicycle is formed. For spirocyclic bicycles, the point of attachment of the second ring can be at any of A1-A5. The second ring can be any carbocycle, substituted carbocycle, heterocarbocycle or substituted heterocarbocylcle of ring size 3, 4, 5, or 6. A nonlimiting list of appropriate carbocyles is provided in Table 2. Exemplary spirocyclic bicycles of Formula 1 are shown below:

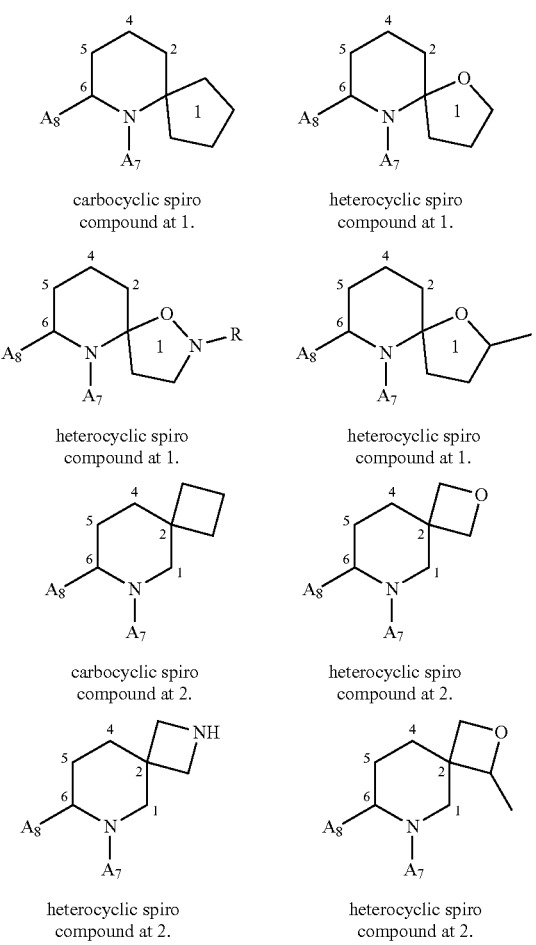

In certain of the bicyclic compounds provided herein a bridged bicycle is formed, in which A1 can be connected to any of A4, A5 or A6 by a carbon bridge, or A6 can be connected to A4 or A2 by a carbon bridge. The carbon bridge can be, for example a methylene (—$CH_2$—), ethylene (—$CH_2CH_2$—) or propylene (—$CH_2CH_2CH_2$—) bridge, or a substituted version thereof. For bridges terminating in either A1 or A6, a heteroatom cannot be present in the bridge.

In additional bicyclic compounds provided herein, A2 is connected to A5 by a carbon, oxygen or nitrogen bridge. The carbon bridge can be, for example, a methylene, ethylene, or propylene bridge or a substituted version thereof. The oxygen bridge can be, for example, an ether (—O—) bridge; and the nitrogen bridge can be, for example, an amine bridge (e.g., —NH— or —$NR_{36}$—).

In the amine bridge, R36 can be one of cyano, halogen, hydroxyl, alkyloxy, alkyl, branched alkyl, halogenated alkyl, branched halogenated alkyl, aryl, arylalkyl, carbocycle, carbocycle-alkyl, alkylcarbonyl, branched alkylcarbonyl, halogenated alkylcarbonyl, branched halogenated alkylcarbonyl, arylcarbonyl alkenyl, substituted alkenyl, alkynyl, alkoxycarbonyl, ether or a small substitution group. The small substitution group is selected from cyano, halogen, alkyl, branched alkyl, halogenated alkyl, hydroxyl, alkyloxy, amino, alkylamino, dialkylamino, mercaptanyl, alkylmercaptanyl, alkylsulfonyl, aminosulfonyl, alkylaminosulfonyl, alkylcarbonyl, alkoxycarbonyl, aminocarbonyl, alkylaminocarbonyl, dialkylaminocarbonyl, aryl, arylalkyl, carbocycle, carbocycle-alkyl, F, Cl, Br, $CH_3$, $CH_2CH_3$, $CH_2F$, $CHF_2$, $CF_3$, n-Pr, n-Bu, i-Bu, sec-bu, i-Pr, t-Bu, CN, OH, OMe, OEt, O-iPr, $OCF_2H$, $OCF_3$, $NH_2$, NHMe, $NMe_2$, methoxycarbonyl, methanesuflonyl, phenyl, benzyl, $MeSO_2$, formyl, and acetyl.

Exemplary bridged bicycles of Formula 1 are shown below:

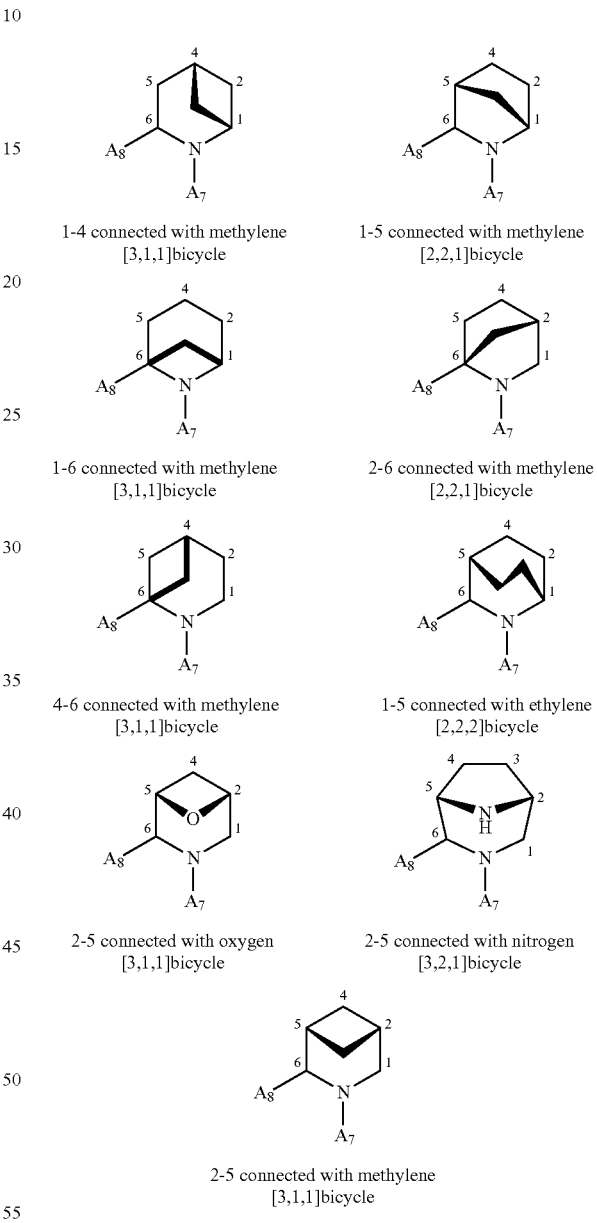

In certain of the bicyclic compounds provided herein a fused bicycle is formed. The point of attachment of the second ring can be at any of A1-A2, A2-A3, A3-A4, A2-A4 (when A3 is null), or A4-A5. The second ring can be any carbocycle, substituted carbocycle, heterocarbocycle or substituted heterocarbocylcle of ring size 3, 4, 5, or 6. A non-limiting list of appropriate carbocyles is provided in Table 2. The second ring can also be any aryl, substituted aryl, heteroaryl, or substituted heteroaryl. A non-limiting list of examples of the second ring is provided in Table 1. Exemplary fused bicycles of Formula 1 are shown below:

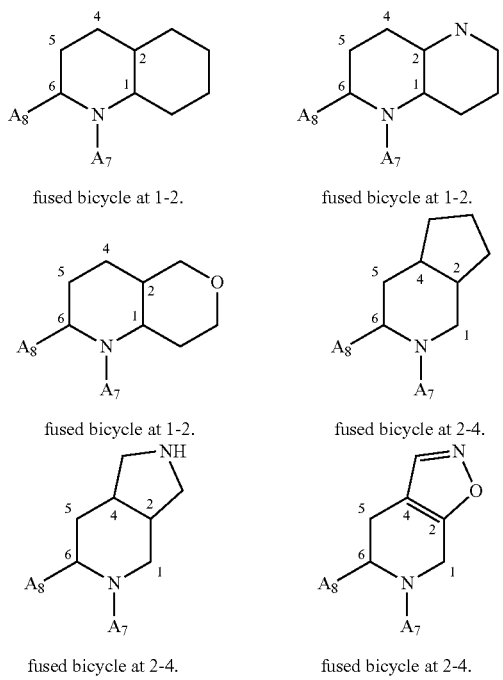

fused bicycle at 1-2.   fused bicycle at 1-2.

fused bicycle at 1-2.   fused bicycle at 2-4.

fused bicycle at 2-4.   fused bicycle at 2-4.

For spirocyclic and fused bicyclic compounds, the second ring can be, for example, aryl, phenyl, cycloalkyl (e.g., cyclohexyl), pyridine, pyrimidine, furan, thiophene or pyridazine.

In the spirocyclic and fused bicyclic compounds disclosed herein, either or both of the rings can be substituted with, for example, one or more of cyano, halogen, alkyl, branched alkyl, halogenated alkyl, hydroxyl, alkyloxy, formyl, acetyl, amino, alkylamino, dialkylamino, mercaptanyl, alkylmercaptanyl, or a small substitution group. The small substitution group is selected from cyano, halogen, alkyl, branched alkyl, halogenated alkyl, hydroxyl, alkyloxy, oxyalkyl, amino, alkylamino, dialkylamino, mercaptanyl, alkylmercaptanyl, alkylsulfonyl, aminosulfonyl, alkylaminosulfonyl, alkylcarbonyl, alkoxycarbonyl, aminocarbonyl, alkylaminocarbonyl, dialkylaminocarbonyl, aryl, arylalkyl, carbocycle, carbocycle-alkyl, F, Cl, Br, $CH_3$, $CH_2CH_3$, $CH_2F$, $CHF_2$, $CF_3$, n-Pr, n-Bu, i-Bu, sec-Bu, iPr, t-Bu, CN, OH, OMe, OEt, O-iPr, $OCF_2H$, $OCF_3$, $NH_2$, NHMe, $NMe_2$, methoxycarbonyl, methanesulfonyl, phenyl, benzyl, $MeSO_2$, formyl or acetyl.

In certain embodiments, provided herein are compounds having the structure

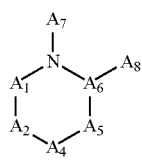

Formula 1a wherein the definitions of A1, A2, A4-A8, R1-R10, R16-R35 and "small substitution group" are as provided for Formula I above.

In the compounds of Formula Ia, any one or more of the bonds between N and A1, A1 and A2, A2 and A4, A4 and A5, A5 and A6, and A6 and N can be a double bond, provided that the distribution of double bonds in the molecule results in a stable structure.

In certain embodiments, the compound of Formula Ia is a six-membered, nitrogen-containing ring with substituents A7 and A8.

In certain embodiments, the compound of Formula I is a four, five, six or seven-membered ring that is fused to a second ring, forming a spirocycle, a bridged bicycle or a fused bicycle, as noted above with respect to Formula 1.

In additional embodiments, provided herein are compounds of Formula Ia wherein A8 is an aromatic (aryl) or heteroaromatic (heteroaryl) ring. Exemplary aryl or heteroaryl rings include phenyl, cycloalkyl (e.g., cyclohexyl, cycloheptyl), pyridine, pyridazine, pyrimidine and pyrazine.

In additional embodiments, provided herein are compounds having the structure

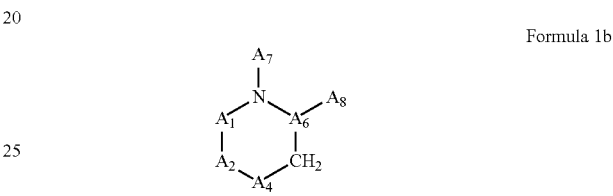

Formula 1b wherein the definitions of A1, A2, A4, A6, A7, R1-R10, R16-R20, R26-R35 and "small substitution group" are as provided for Formula I above, and A8 is an aromatic (aryl) or heteroaromatic (heteroaryl) ring. Exemplary aryl or heteroaryl rings include phenyl, cycloalkyl (e.g., cyclohexyl, cycloheptyl), pyridine, pyridazine, pyrimidine and pyrazine.

In further embodiments, provided herein are compounds having the structure

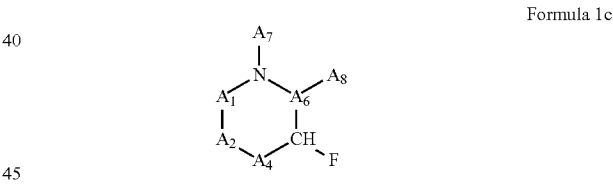

Formula 1c wherein the definitions of A1, A2, A4, A6, A7, R1-R10, R16-R20, R26-R35 and "small substitution group" are as provided for Formula I above, and A8 is an aromatic (aryl) or heteroaromatic (heteroaryl) ring. Exemplary aryl or heteroaryl rings include phenyl, cycloalkyl (e.g., cyclohexyl, cycloheptyl), pyridine, pyridazine, pyrimidine and pyrazine.

In further embodiments, provided herein are compounds of Formula 1a wherein the ring containing N, A1, A2, A4 and A6 is part of a bridged bicyclic ring system. In these bridged bicyclic compounds, A1 can be connected to any of A4, A5 or A6 by a carbon bridge, or A6 can be connected to A4 or A2 by a carbon bridge. The carbon bridge can be, for example a methylene (—$CH_2$—), ethylene (—$CH_2CH_2$—) or propylene (—$CH_2CH_2CH_2$—) bridge, or a substituted version thereof. For bridges terminating in either A1 or A6, a heteroatom cannot be present in the bridge.

In additional bridged bicyclic compounds of Formula 1a, A2 is connected to A5 by a carbon, oxygen or nitrogen bridge. The carbon bridge can be, for example, a methylene, ethylene, or propylene bridge or a substituted version thereof. The oxygen bridge can be, for example, an ether (—O—) bridge; and the nitrogen bridge can be, for example, an amine bridge (e.g., —NH— or —NR$_{36}$—).

In the amine bridge, R36 can be one of cyano, halogen, hydroxyl, alkyloxy, alkyl, branched alkyl, halogenated alkyl, branched halogenated alkyl, aryl, arylalkyl, carbocycle, carbocycle-alkyl, alkylcarbonyl, branched alkylcarbonyl, halogenated alkylcarbonyl, branched halogenated alkylcarbonyl, arylcarbonyl alkenyl, substituted alkenyl, alkynyl, alkoxycarbonyl, ether or a small substitution group. The small substitution group is selected from cyano, halogen, alkyl, branched alkyl, halogenated alkyl, hydroxyl, alkyloxy, amino, alkylamino, dialkylamino, mercaptanyl, alkylmercaptanyl, alkylsulfonyl, aminosulfonyl, alkylaminosulfonyl, alkylcarbonyl, alkoxycarbonyl, aminocarbonyl, alkylaminocarbonyl, dialkylaminocarbonyl, aryl, arylalkyl, carbocycle, carbocycle-alkyl, F, Cl, Br, $CH_3$, $CH_2CH_3$, $CH_2F$, $CHF_2$, $CF_3$, n-Pr, n-Bu, i-Bu, sec-bu, i-Pr, t-Bu, CN, OH, OMe, OEt, O-iPr, $OCF_2H$, $OCF_3$, $NH_2$, NHMe, $NMe_2$, methoxycarbonyl, methanesuflonyl, phenyl, benzyl, $MeSO_2$, formyl, and acetyl.

Exemplary bridged bicycles of Formula 1a are shown below:

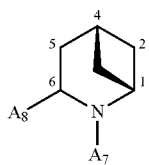
1-4 connected with methylene
[3,1,1]bicycle

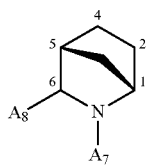
1-5 connected with methylene
[2,2,1]bicycle

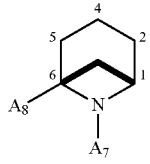
1-6 connected with methylene
[3,1,1]bicycle

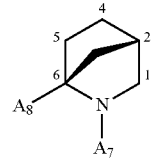
2-6 connected with methylene
[2,2,1]bicycle

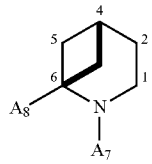
4-6 connected with methylene
[3,1,1]bicycle

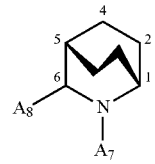
1-5 connected with ethylene
[2,2,2]bicycle

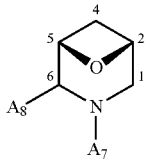
2-5 connected with oxygen
[3,1,1]bicycle

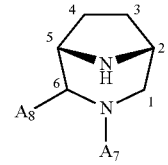
2-5 connected with nitrogen
[3,2,1]bicycle

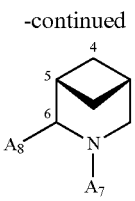
2-5 connected with methylene
[3,1,1]bicycle

In further embodiments, provided herein are compounds having the structure

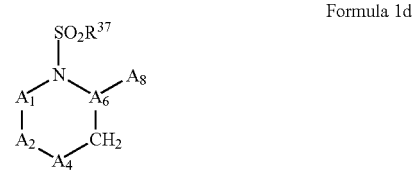

Formula 1d wherein the definitions of A1, A2, A4, A6, R1-R10, R16-R20, R26-R35 and "small substitution group" are as provided for Formula I above, and A8 is an aromatic (aryl) or heteroaromatic (heteroaryl) ring. Exemplary aryl or heteroaryl rings include phenyl, cycloalkyl (e.g., cyclohexyl, cycloheptyl), pyridine, pyridazine, pyrimidine and pyrazine.

In additional embodiments, provided herein are compounds having the structure

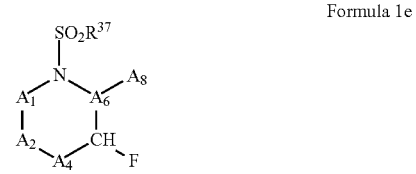

Formula 1e wherein the definitions of A1, A2, A4, A6, R1-R10, R16-R20, R26-R35 and "small substitution group" are as provided for Formula I above, and A8 is an aromatic (aryl) or heteroaromatic (heteroaryl) ring. Exemplary aryl or heteroaryl rings include phenyl, cycloalkyl (e.g., cyclohexyl, cycloheptyl), pyridine, pyridazine, pyrimidine and pyrazine.

In the compounds of Formulas 1d and 1e, R37 can be one of cyano, halogen, hydroxyl, alkyloxy, oxyalkyl, alkyl, branched alkyl, halogenated alkyl, branched halogenated alkyl, aryl, substituted aryl, arylalkyl, carbocycle, carbocycle-alkyl, alkylcarbonyl, branched alkylcarbonyl, halogenated alkylcarbonyl, branched halogenated alkylcarbonyl, arylcarbonyl alkenyl, substituted alkenyl, alkynyl, alkoxycarbonyl, ether or a small substitution group. The small substitution group is selected from cyano, halogen, alkyl, branched alkyl, halogenated alkyl, hydroxyl, alkyloxy, amino, alkylamino, dialkylamino, mercaptanyl, alkylmercaptanyl, alkylsulfonyl, aminosulfonyl, alkylaminosulfonyl, alkylcarbonyl, alkoxycarbonyl, aminocarbonyl, alkylaminocarbonyl, dialkylaminocarbonyl, aryl, arylalkyl, carbocycle, carbocycle-alkyl, F, Cl, Br, $CH_3$, $CH_2CH_3$, $CH_2F$, $CHF_2$, $CF_3$, n-Pr, n-Bu, i-Bu, sec-bu, i-Pr, t-Bu, CN, OH, OMe, OEt, O-iPr, $OCF_2H$, $OCF_3$, $NH_2$, NHMe, $NMe_2$, methoxycarbonyl, methanesuflonyl, phenyl, benzyl, $MeSO_2$, formyl, and acetyl.

In further embodiments, provided herein are compounds of Formula 1a wherein the ring containing N, A1, A2, A4 and A6 is part of a bridged bicyclic ring system; A8 is aryl or heteroaryl; and A7 is —SO$_2$R$^{37}$. Exemplary aryl or heteroaryl rings include phenyl, cycloalkyl (e.g., cyclohexyl, cycloheptyl), pyridine, pyridazine, pyrimidine and pyrazine. R37 is the same as defined above for the compounds of Formulas 1d and 1e.

In these bridged bicyclic compounds, A1 can be connected to any of A4, A5 or A6 by a carbon bridge, or A6 can be connected to A4 or A2 by a carbon bridge. The carbon bridge can be, for example a methylene (—CH$_2$—), ethylene (—CH$_2$CH$_2$—) or propylene (—CH$_2$CH$_2$CH$_2$—) bridge, or a substituted version thereof. For bridges terminating in either A1 or A6, a heteroatom cannot be present in the bridge.

In additional bridged bicyclic compounds of Formula 1a, A2 is connected to A5 by a carbon, oxygen or nitrogen bridge. The carbon bridge can be, for example, a methylene, ethylene, or propylene bridge or a substituted version thereof. The oxygen bridge can be, for example, an ether (—O—) bridge; and the nitrogen bridge can be, for example, an amine bridge (e.g., —NH— or —NR$_{36}$—).

In the amine bridge, R36 can be one of cyano, halogen, hydroxyl, alkyloxy, alkyl, branched alkyl, halogenated alkyl, branched halogenated alkyl, aryl, arylalkyl, carbocycle, carbocycle-alkyl, alkylcarbonyl, branched alkylcarbonyl, halogenated alkylcarbonyl, branched halogenated alkylcarbonyl, arylcarbonyl alkenyl, substituted alkenyl, alkynyl, alkoxycarbonyl, ether or a small substitution group. The small substitution group is selected from cyano, halogen, alkyl, branched alkyl, halogenated alkyl, hydroxyl, alkyloxy, amino, alkylamino, dialkylamino, mercaptanyl, alkylmercaptanyl, alkylsulfonyl, aminosulfonyl, alkylaminosulfonyl, alkylcarbonyl, alkoxycarbonyl, aminocarbonyl, alkylaminocarbonyl, dialkylaminocarbonyl, aryl, arylalkyl, carbocycle, carbocycle-alkyl, F, Cl, Br, CH$_3$, CH$_2$CH$_3$, CH$_2$F, CHF$_2$, CF$_3$, n-Pr, n-Bu, i-Bu, sec-bu, i-Pr, t-Bu, CN, OH, OMe, OEt, O-iPr, OCF$_2$H, OCF$_3$, NH$_2$, NHMe, NMe$_2$, methoxycarbonyl, methanesuflonyl, phenyl, benzyl, MeSO$_2$, formyl, and acetyl.

In these aforementioned bicyclic compounds, either or both of the rings can be substituted with, for example, one or more of cyano, halogen, alkyl, branched alkyl, halogenated alkyl, hydroxyl, alkyloxy, formyl, acetyl, amino, alkylamino, dialkylamino, mercaptanyl, alkylmercaptanyl, or a small substitution group. The small substitution group is selected from cyano, halogen, alkyl, branched alkyl, halogenated alkyl, hydroxyl, alkyloxy, amino, alkylamino, dialkylamino, mercaptanyl, alkylmercaptanyl, alkylsulfonyl, aminosulfonyl, alkylaminosulfonyl, alkylcarbonyl, alkoxycarbonyl, aminocarbonyl, alkylaminocarbonyl, dialkylaminocarbonyl, aryl, arylalkyl, carbocycle, carbocycle-alkyl, F, Cl, Br, CH$_3$, CH$_2$CH$_3$, CH$_2$F, CHF$_2$, CF$_3$, n-Pr, n-Bu, i-Bu, sec-Bu, iPr, t-Bu, CN, OH, OMe, OEt, O-iPr, OCF$_2$H, OCF$_3$, NH$_2$, NHMe, NMe$_2$, methoxycarbonyl, methanesulfonyl, phenyl, benzyl, MeSO$_2$, formyl or acetyl.

In further embodiments, provided herein are compounds having the structure

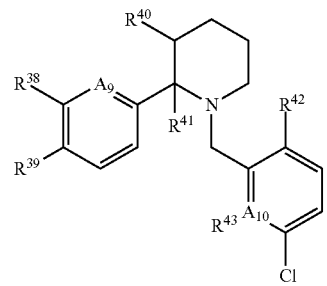

Formula 2 wherein A9 is CH or N; A10 is C or N; and R38-R43 are H, D, Cl, F, Br, CF$_3$, —OCF$_3$, CH$_3$, CH$_2$CH$_3$, CH$_2$F, CHF$_2$, n-Pr, i-Pr, n-Bu, iso-Bu, sec-Bu, t-Bu, —CN, —OH, —OCH$_3$, —OCH$_2$CH$_3$, O-iPr, OCF$_2$H, OCHF$_2$, OCF$_3$, NH$_2$, NHCH$_3$, N(CH$_3$)$_2$, methoxycarbonyl, methanesulfonyl MeSO$_2$, formyl or acetyl; or R43 is null if A10 is N.

In certain embodiments, in the compound of Formula 2 A9 is CH or N, A10 is C or N; R38 is Br, Cl, CF$_3$ or —OCF$_3$, R39 is H, Cl or F; R40 is H or F; R41 is H or D (deuterium); R42 is H or F; R43 is H or F when A10 is C; and R43 is null when A10 is N.

In additional embodiments of the compound of Formula 2, A9 is CH; A10 is N; R38 is Cl; R39 is F; R40 is H; R41 is H; R42 is H and R43 is null.

In additional embodiments of the compound of Formula 2, A9 is N; A10 is C; R38 is CF$_3$; R39 is H; R40 is H; R41 is H; R42 is F; and R43 is H.

In additional embodiments of the compound of Formula 2, A9 is N; A10 is C; R38 is —OCF$_3$; R39 is H; R40 is H; R41 is H; R42 is F; and R43 is H.

In additional embodiments of the compound of Formula 2, A9 is N; A10 is C; R38 is CF$_3$; R39 is H; R40 is H; R41 is H; R42 is H; and R43 is H.

In additional embodiments of the compound of Formula 2, A9 is N; A10 is C; R38 is CF$_3$; R39 is H; R40 is H; R41 is H; R42 is H; and R43 is F.

In additional embodiments of the compound of Formula 2, A9 is CH; A10 is C; R38 is Br; R39 is F; R40 is F; R41 is H; R42 is H; and R43 is H.

In additional embodiments of the compound of Formula 2, A9 is CH; A10 is C; R38 is Br; R39 is F; R40 is F; R41 is D; R42 is H; and R43 is H.

In additional embodiments of the compound of Formula 2, A9 is CH; A10 is C; R38 is CF$_3$; R39 is H; R40 is F; R41 is D; R42 is H; and R43 is F.

In further embodiments, provided herein are compounds having the structure

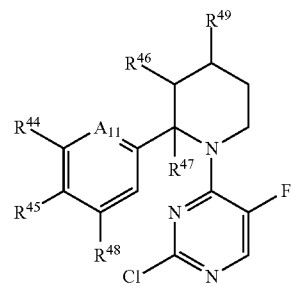

Formula 3 wherein A11 is CH or N; and R44-R49 are H, D, Cl, F, Br, CF$_3$, —OCF$_3$, CH$_3$, CH$_2$CH$_3$, CH$_2$F, CHF$_2$, n-Pr, i-Pr, n-Bu, iso-Bu, sec-Bu, t-Bu, —CN, —OH, —OCH$_3$, —OCH$_2$CH$_3$, O-iPr, OCF$_2$H, OCHF$_2$, OCF$_3$, NH$_2$, NHCH$_3$, N(CH$_3$)$_2$, methoxycarbonyl, methanesulfonyl MeSO$_2$, formyl or acetyl.

In certain embodiments, in the compound of Formula 3, A11 is CH or N; R44 is Cl, Br or CF$_3$; R45 is H, Cl, F or OCF$_3$; R46 is H or F; R47 is H or D (deuterium); R48 is H or F; and R49 is null, =CH or F.

In additional embodiments of the compound of Formula 3, A11 is CH; R44 is Cl; R45 is F; R46 is H; R47 is H; R48 is H; and R49 is null.

In additional embodiments of the compound of Formula 3, A11 is CH; R44 is Br; R45 is F; R46 is H; R47 is H; R48 is H; and R49 is null.

In additional embodiments of the compound of Formula 3, A11 is CH; R44 is F; R45 is F; R46 is H; R47 is H; R48 is H; and R49 is null.

In additional embodiments of the compound of Formula 3, A11 is N; R44 is CF$_3$; R45 is H; R46 is H; R47 is H; R48 is H; and R49 is null.

In additional embodiments of the compound of Formula 3, A11 is CH; R44 is CF$_3$; R45 is H; R46 is H; R47 is H; R48 is F; and R49 is null.

In additional embodiments of the compound of Formula 3, A11 is CH; R44 is CF$_3$; R45 is H; R46 is H; R47 is H; R48 is F; and R49 is =CH.

In additional embodiments of the compound of Formula 3, A11 is CH; R44 is CF$_3$; R45 is H; R46 is H; R47 is H; R48 is F; and R49 is F.

In additional embodiments of the compound of Formula 3, A11 is CH; R44 is CF$_3$; R45 is H; R46 is H; R47 is H; R48 is H; and R49 is null.

In additional embodiments of the compound of Formula 3, A11 is CH; R44 is CF$_3$; R45 is Cl; R46 is H; R47 is H; R48 is H; and R49 is null.

In additional embodiments of the compound of Formula 3, A11 is CH; R44 is Br; R45 is —OCF$_3$; R46 is H; R47 is H; R48 is H; and R49 is null.

In additional embodiments of the compound of Formula 3, A11 is CH; R44 is Br; R45 is Cl; R46 is H; R47 is H; R48 is H; and R49 is null.

In additional embodiments of the compound of Formula 3, A11 is CH; R44 is CF$_3$; R45 is H; R46 is F; R47 is D; R48 is H; and R49 is null.

In further embodiments, provided herein are compounds having the structure

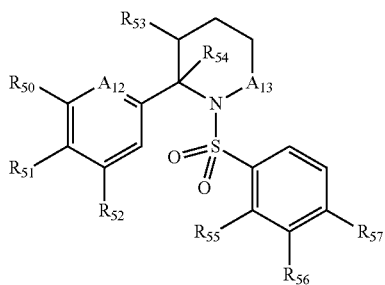

Formula 4 wherein A12 is CH or N; A13 is CH$_2$, NH or null; and R50-R57 are H, D, Cl, F, Br, CF$_3$, —OCF$_3$, CH$_3$, CH$_2$CH$_3$, CH$_2$F, CHF$_2$, n-Pr, i-Pr, n-Bu, iso-Bu, sec-Bu, t-Bu, —CN, —OH, —OCH$_3$, —OCH$_2$CH$_3$, O-iPr, OCF$_2$H, OCHF$_2$, OCF$_3$, NH$_2$, NHCH$_3$, N(CH$_3$)$_2$, methoxycarbonyl, methanesulfonyl MeSO$_2$, formyl or acetyl. In addition, R50 and R51 together can form a second ring (aryl or heteroaryl) that is fused to the A12-containing ring. In certain embodiments, in the compound of Formula 4, A12 is C or N; A13 is CH$_2$ or null; R50 is Cl, Br or CF$_3$; R51 is H, F or Cl; R52 is H or F; R53 is H, F or CH$_3$; R54 is H or D; R55 is H or F; R56 is H or Cl; and R57 is H or Cl.

In further embodiments, provided herein are compounds having the structure

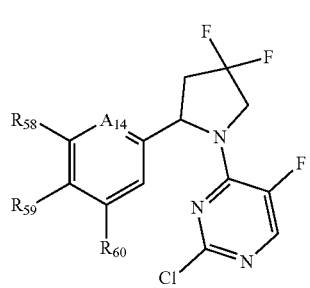

Formula 5 wherein A14 is CH or N; and R58-R60 are H, D, Cl, F, Br, CF$_3$, —OCF$_3$, CH$_3$, CH$_2$CH$_3$, CH$_2$F, CHF$_2$, n-Pr, i-Pr, n-Bu, iso-Bu, sec-Bu, t-Bu, —CN, —OH, —OCH$_3$, —OCH$_2$CH$_3$, O-iPr, OCF$_2$H, OCHF$_2$, OCF$_3$, NH$_2$, NHCH$_3$, N(CH$_3$)$_2$, methoxycarbonyl, methanesulfonyl MeSO$_2$, formyl or acetyl.

In certain embodiments, in the compound of Formula 5, A14 is CH or N; R58 is Cl, Br or CF$_3$; R59 is H, F or Cl; and R60 is H, F or CF$_3$.

In further embodiments, provided herein are compounds having the structure

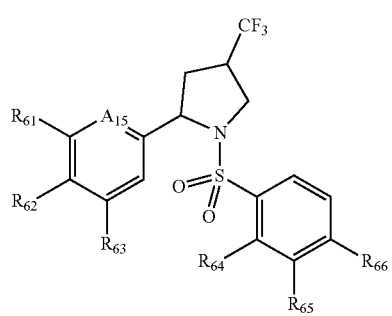

Formula 6 wherein A15 is CH or N; and R61-R66 are H, D, Cl, F, Br, CF$_3$, —OCF$_3$, CH$_3$, CH$_2$CH$_3$, CH$_2$F, CHF$_2$, n-Pr, i-Pr, n-Bu, iso-Bu, sec-Bu, t-Bu, —CN, —OH, —OCH$_3$, —OCH$_2$CH$_3$, O-iPr, OCF$_2$H, OCHF$_2$, OCF$_3$, NH$_2$, NHCH$_3$, N(CH$_3$)$_2$, methoxycarbonyl, methanesulfonyl MeSO$_2$, formyl or acetyl.

In certain embodiments, in the compound of Formula 6, A15 is CH or N; R61 is Cl, Br or CF$_3$; R62 is H, F, Cl or —OCH$_3$; R63 is H or F; R64 is H or F; R65 is H or Cl; and R66 is H or Cl.

In further embodiments, provided herein are compounds having the structure

Formula 7

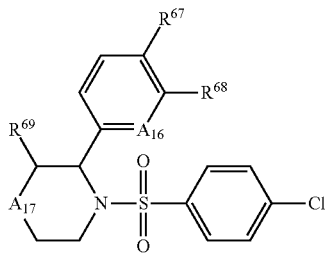

wherein A16 is CH or N; A17 is CH₂, NH or null; and R67-R69 are H, D, Cl, F, Br, CF₃, —OCF₃, CH₃, CH₂CH₃, CH₂F, CHF₂, n-Pr, i-Pr, n-Bu, iso-Bu, sec-Bu, t-Bu, —CN, —OH, —OCH₃, —OCH₂CH₃, O-iPr, OCF₂H, OCHF₂, OCF₃, NH₂, NHCH₃, N(CH₃)₂, methoxycarbonyl, methanesulfonyl MeSO₂, formyl or acetyl.

In certain embodiments, in the compound of Formula 7, A16 is CH or N; A17 is CH₂ or null; R67 is H, Cl, F, —OCH₃ or —OCF₃; R68 is Cl, Br, CH₃ or CF₃; and when A17 is null, R69 is —CH₃.

In further embodiments, provided herein are compounds having the structure

Formula 8

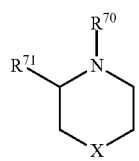

wherein X is C, O, S, SO, SO₂, N, NH, NCH₃, NAc, NCO(CMe₂OH), NSO₂Me, or NR72; wherein R72 is alkyl, aryl, heteroaryl; R70 is aryl, heteroaryl, substituted aryl and substituted heteroaryl and R71 is aryl, heteroaryl, substituted aryl and substituted heteroaryl.

An aryl group, as present in any of the compounds disclosed herein, is either a monocyclic aromatic group or a bicyclic aromatic group, and can contain heteroatoms in the aromatic group (e.g., heteroaryl). Non-limiting structures of exemplary aryl groups are provided in Table 1.

TABLE 1

Exemplary aryl groups

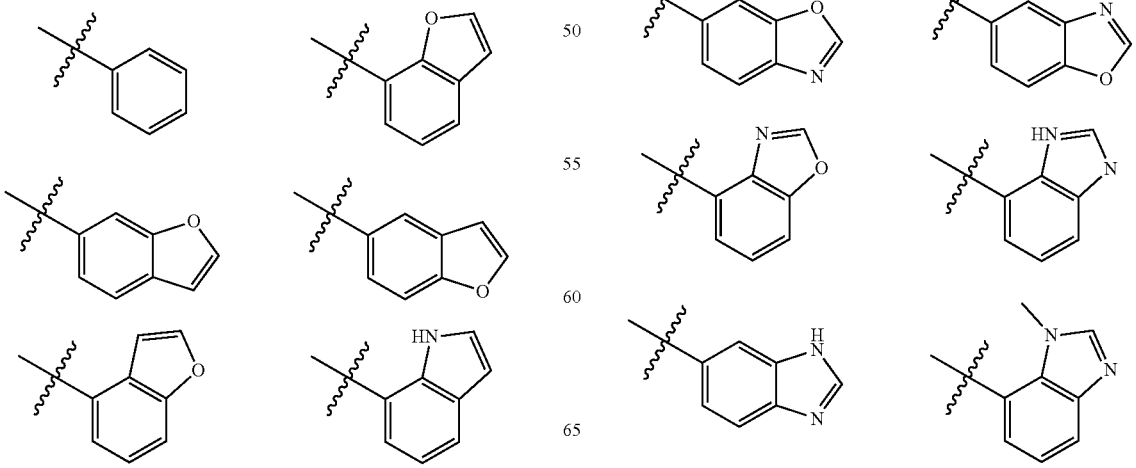

TABLE 1-continued

Exemplary aryl groups

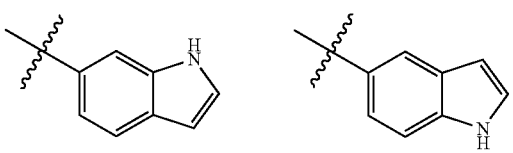

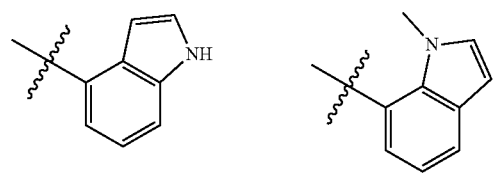

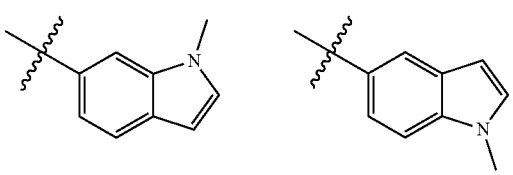

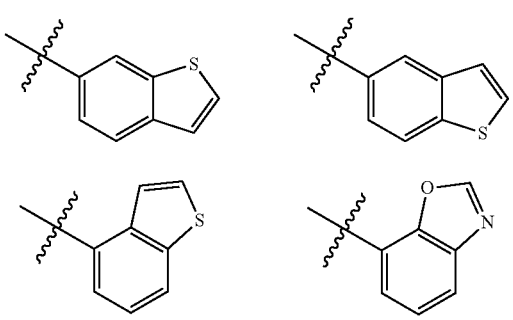

TABLE 1-continued
Exemplary aryl groups
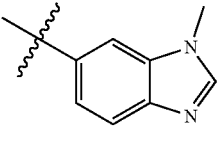 [SMILES: *c1ccc2ccn(C)c2c1] 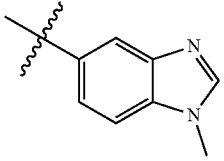 [SMILES: *c1ccc2c(c1)ncn2C] 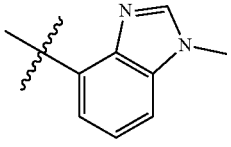 [SMILES: *c1cccc2c1ncn2C] 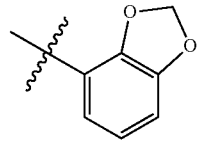 [SMILES: *c1cccc2c1OCO2]
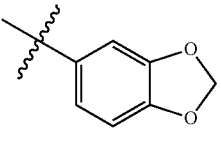 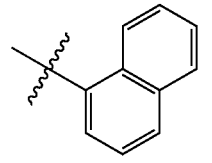 [SMILES: *c1cccc2ccccc12] 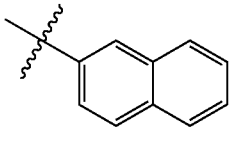 [SMILES: *c1ccc2ccccc2c1] 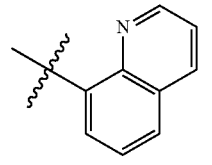 [SMILES: *c1cccc2cccnc12]
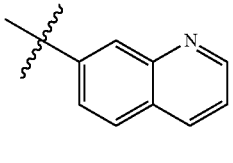 [SMILES: *c1ccc2cccnc2c1] 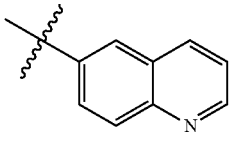 [SMILES: *c1ccc2ncccc2c1] 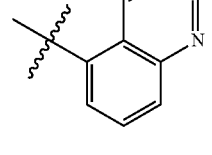 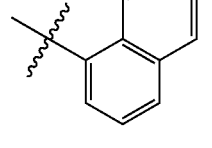
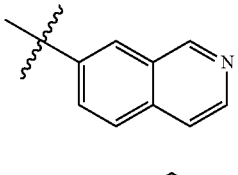 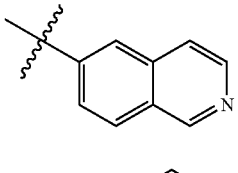 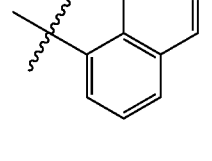 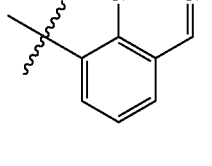
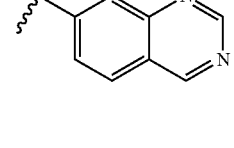 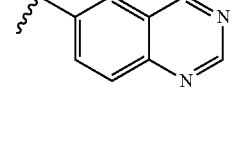 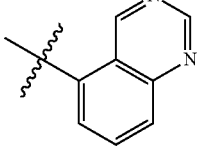 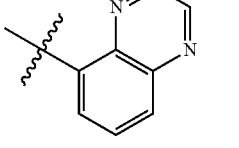
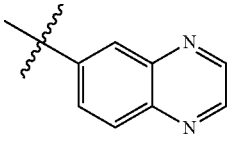 [SMILES: *c1ccc2nccnc2c1] 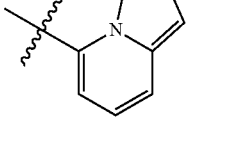 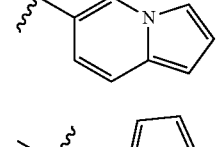 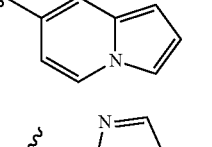
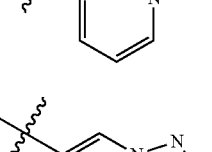 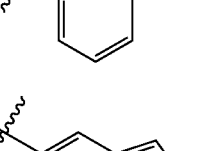 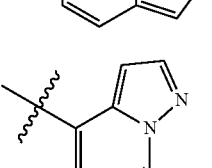 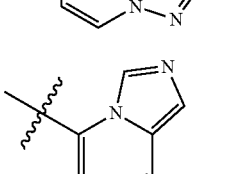
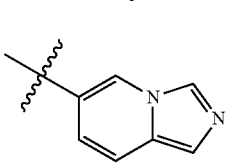 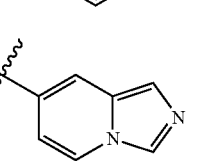 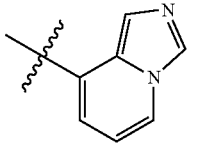 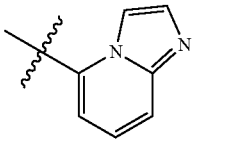 [SMILES: *c1cccc2nccn12]
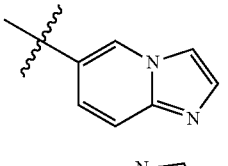 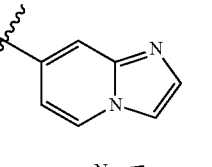 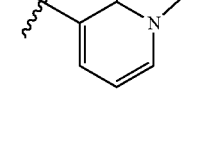 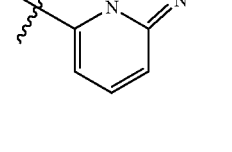
 

TABLE 1-continued
Exemplary aryl groups
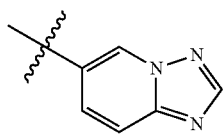 [SMILES: *c1ccc2ncnn2c1] 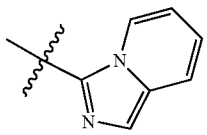 [SMILES: *c1ncc2ccccn12]
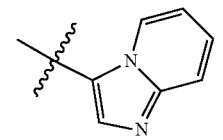 [SMILES: *c1cnc2ccccn12] 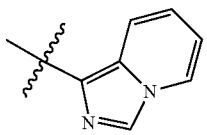 [SMILES: *c1ncn2ccccc12]
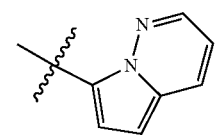 [SMILES: *c1ccc2cccnn12] 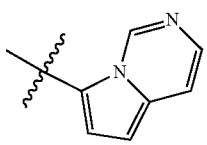 [SMILES: *c1ccc2ccncn12]
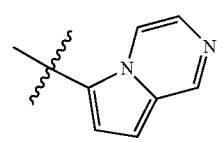 [SMILES: *c1ccc2cnccn12] 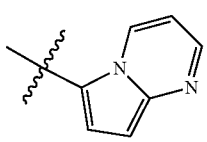 [SMILES: *c1ccc2ncccn12]
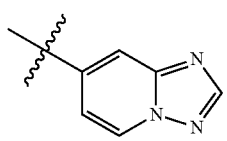 [SMILES: *c1ccn2ncnc2c1] 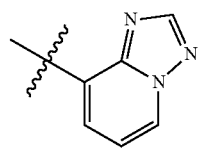 [SMILES: *c1cccn2ncnc12]
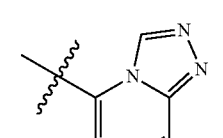 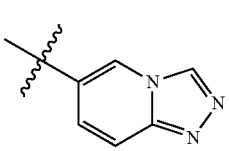 [SMILES: *c1ccc2nncn2c1]
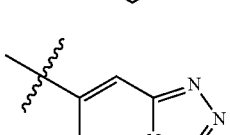 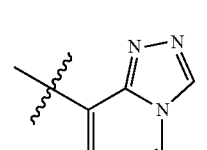
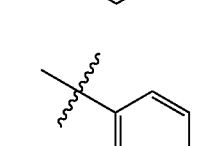 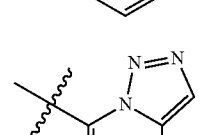
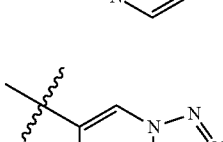 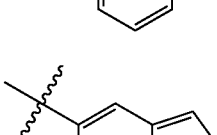
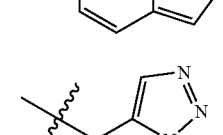 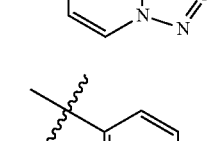
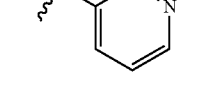
TABLE 1-continued
Exemplary aryl groups
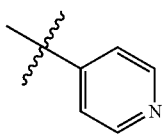 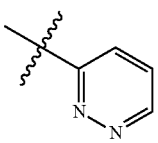 [SMILES: *c1cccnc1]
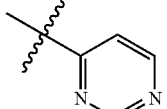
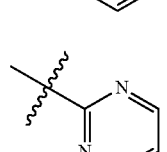
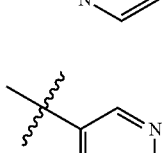
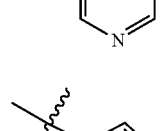
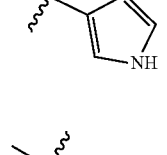
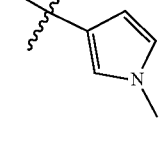
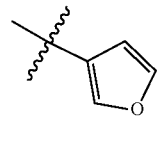 [SMILES: *c1ccoc1]
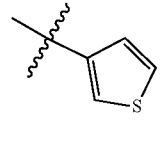 [SMILES: *c1ccsc1]
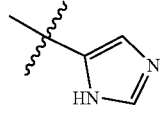 [SMILES: *c1cnc[nH]1]
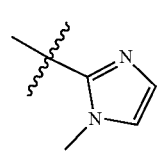 [SMILES: *c1nccn1C] 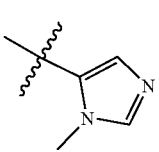 [SMILES: *c1cncn1C]

TABLE 1-continued
Exemplary aryl groups
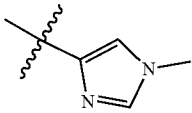 [SMILES: *c1cn(C)cn1] 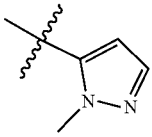 [SMILES: *c1ccnn1C]
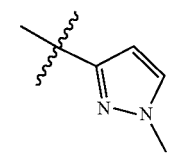 [SMILES: *c1ccn(C)n1] 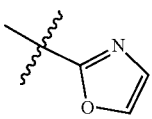
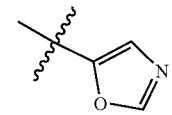 [SMILES: *c1cnco1] 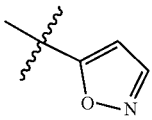 [SMILES: *c1ccno1]
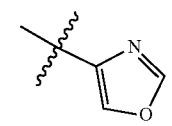 [SMILES: *c1cocn1] 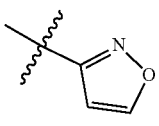 [SMILES: *c1ccon1]
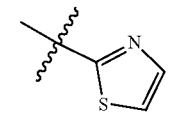 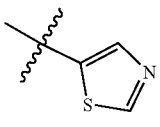 [SMILES: *c1cncs1]
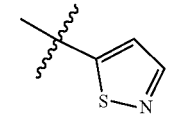 [SMILES: *c1ccns1] 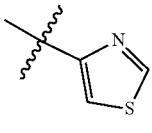 [SMILES: *c1cscn1]
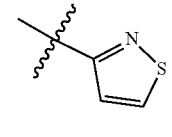 [SMILES: *c1ccsn1] 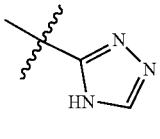
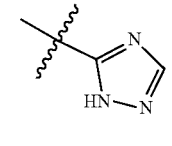 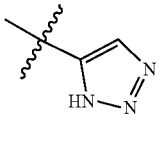
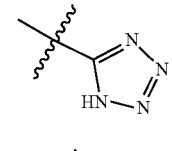 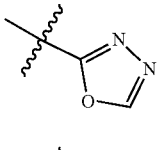
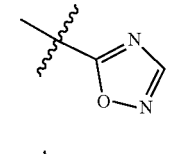 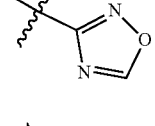
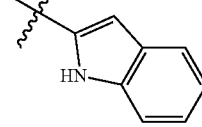 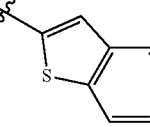
TABLE 1-continued
Exemplary aryl groups
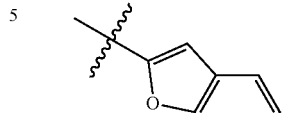 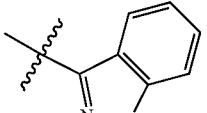
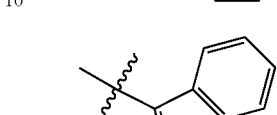 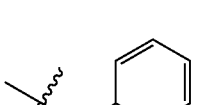
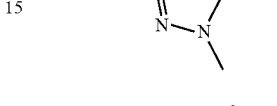 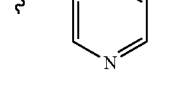
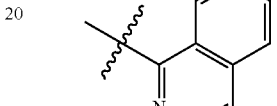 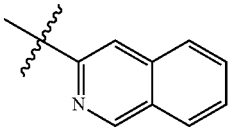 [SMILES: *c1cc2ccccc2cn1]
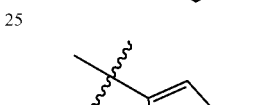 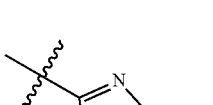
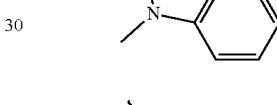 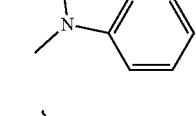
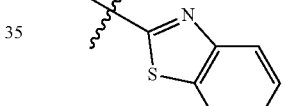 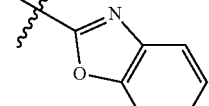
 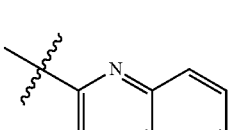
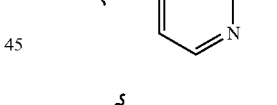 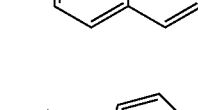
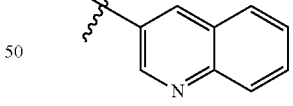 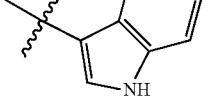
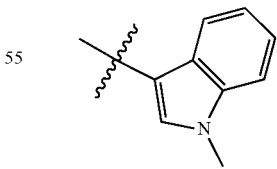 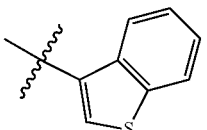
 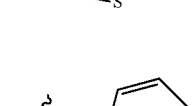
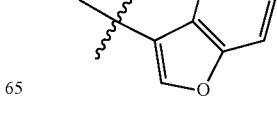 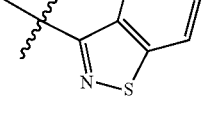

TABLE 1-continued

Exemplary aryl groups

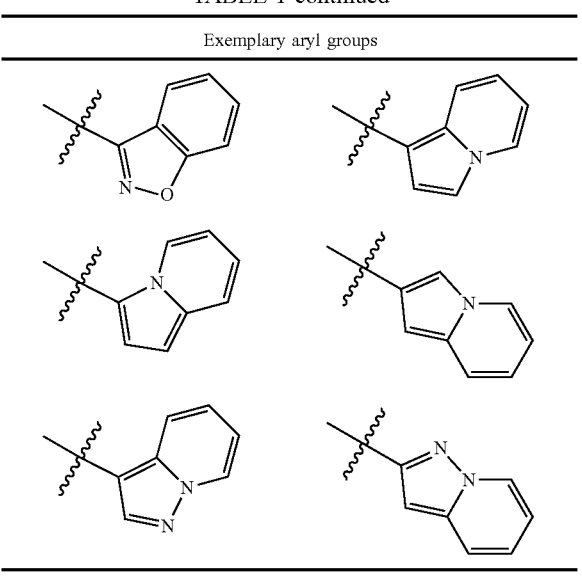

A carbocycle, as present in certain of the compounds disclosed herein, is either a monocyclic or a bicyclic non-aromatic ring system. Table 2 provides non-limiting structures of some exemplary carbocycles, wherein X1 and X2 are independently O, S, N, NH or NR70. R70 can be hydroxyl, alkyloxy, alkyl, branched alkyl, halogenated alkyl, branched halogenated alkyl, aryl, arylalkyl, carbocycle, carbocycle-alkyl, alkylcarbonyl, branched alkylcarbonyl, halogenated alkylcarbonyl, branched halogenated alkylcarbonyl, arylcarbonyl, alkoxycarbonyl or a small substitution group selected from F, Cl, Br, $CH_3$, $CH_2CH_3$, $CH_2F$, $CHF_2$, $CF_3$, n-Pr, n-Bu, i-Bu, sec-Bu, i-Pr, t-Bu, CN, OH, OMe, OEt, O-i-Pr, methoxycarbonyl, phenyl, benzyl, formyl or acetyl, providing the resulting structure is stable. Although a carbocycle can contain one or more double bond(s), the distribution of double bonds in a carbocycle does not constitute an aromatic ring system.

TABLE 2

Exemplary carbocyclic groups

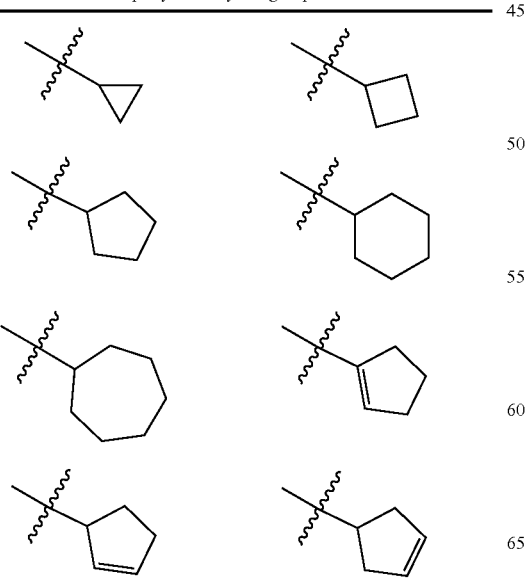

TABLE 2-continued

Exemplary carbocyclic groups

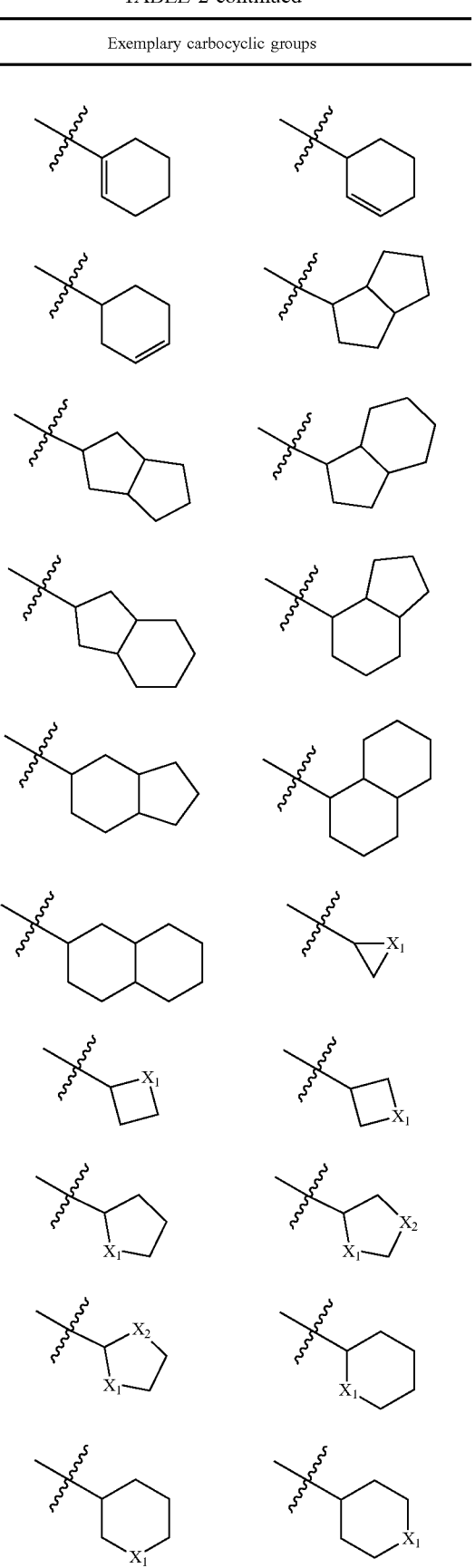

TABLE 2-continued
Exemplary carbocyclic groups
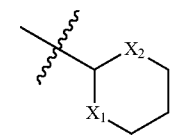 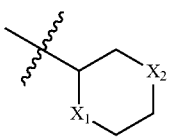
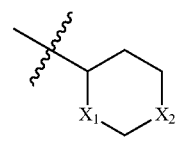 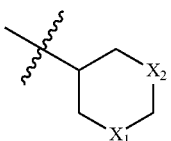
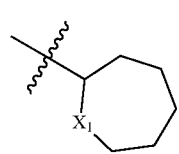 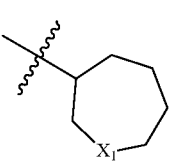
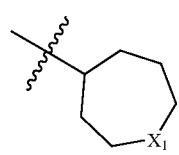 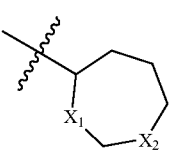
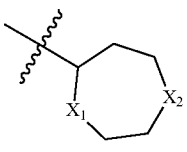 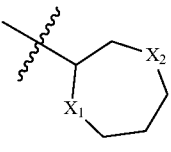
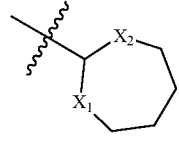 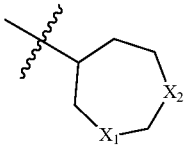
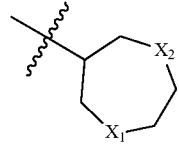 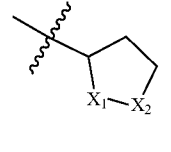
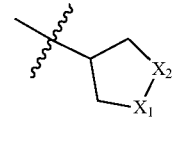 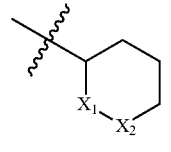
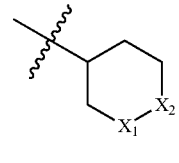 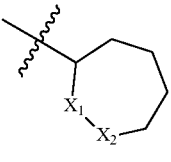
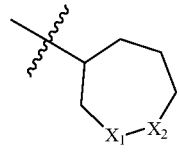 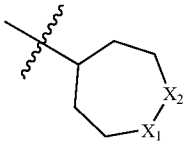
TABLE 2-continued
Exemplary carbocyclic groups
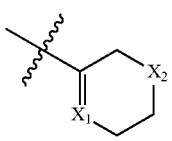 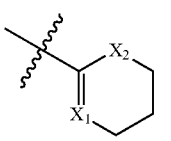
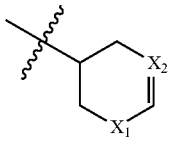 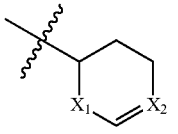
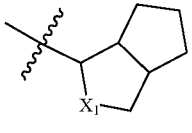 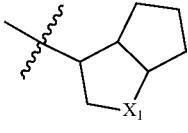
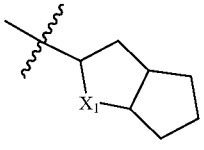 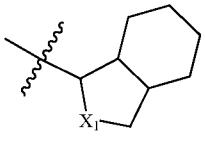
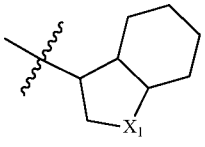 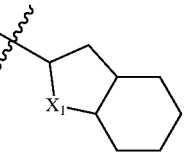
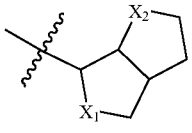 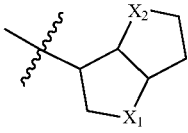
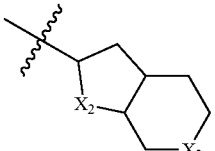 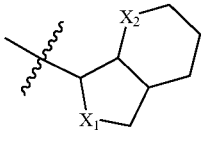
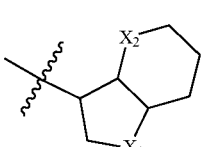 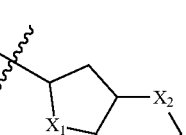
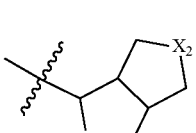 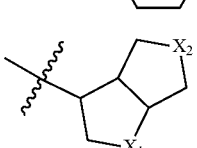
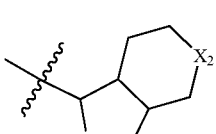 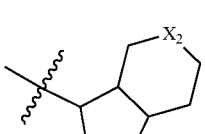
 

TABLE 2-continued

Exemplary carbocyclic groups

Signal Bias

Activation of the G-protein-coupled MOR results in a number of downstream effects, including GDP/GTP exchange, ERK phosphorylation, recruitment of β-arrestins (i.e., β-arrestin 1, β-arrestin 2 and β-arrestin 3) and inhibition of cAMP production. A number of studies have shown that signaling events downstream of GPCR activation have significant effects on physiologic processes. Kenakin, T. (2015b) *British Pharmacological Society* 173:4238-4235. For example, animal knockout studies (Soergel et al., supra and references therein) have demonstrated the benefits of ligands that inhibit adenylyl cyclase activity more strongly than they stimulate β-arrestin recruitment. It is believed that activation of the β-arrestin pathway not only negatively impacts pain amelioration, but is directly contributory to gastrointestinal side effects of opiates. Raehal et al., (2005) *J. Pharmacol. Exp. Therapeutics* 314:1195-1201; Thompson et al. (2015) *Molecular Pharmacology* 88:335-346; Rivero et al. (2012) *Molecular Pharmacology*, (2012) 82:178-188; Pradham et al. (2012) *British Journal of Pharmacology* 167(5):960-969. In fact, it has been clinically demonstrated that the therapeutic index for an orthosteric partial agonist of the MOR is increased by biasing the signal toward adenylate cyclase inhibition and away from β-arrestin signaling. Thus, one approach to improving the therapeutic efficacy of opiates and opioids has been to modify orthosteric ligands such that they exhibit selective signal bias.

Certain of the MOR PAMs disclosed herein also exhibit selective signal bias, in that they have differential effects on downstream processes resulting from MOR signaling. For example, Table 3 shows that certain compounds have quantitatively different $EC_{50}$ and maximal response values for β-arrestin recruitment compared to adenylyl cyclase inhibition. Table 4 shows results of similar analyses of additional compounds.

TABLE 3

Compounds showing selective signal bias

| No. | β-arr. $EC_{50}$ (nM) | β-arr. Max Resp. | cAMP $EC_{50}$ (nM) | cAMP Max Resp. |
|---|---|---|---|---|
| 1 | 572 | 138 | 186 | 63 |
| 2 | 155 | 72 | 170 | 85 |
| 14 | 13,212 | 111 | 9,608 | 43 |
| 44 | 5,670 | 99 | 3,735 | 57 |
| 100 | 522 | 76 | >25,000 | 25 |
| 207 | 1,172 | 116 | 969 | 34 |
| 224 | 11,803 | 305 | 409 | 66 |

Legend:
The first column provides the compound number (identified elsewhere herein) of the compound tested.
The second column provides $EC_{50}$ values for β-arrestin recruitment;
the third column provides maximal response values for β-arrestin recruitment;
the fourth column provides $EC_{50}$ values for adenylyl cyclase inhibition; and
the fifth column provides maximal response values for adenylyl cyclase inhibition.

TABLE 4

Activity of compounds on beta-arrestin signaling and on inhibition of cAMP formation.

| Compound No. | β-arr. $EC_{50}$ | β-arr Max. Resp. | cAMP $EC_{50}$ | cAMP Max. Resp. |
|---|---|---|---|---|
| 1 | A | F | A | F |
| 2 | A | F | A | F |
| 3 | A | F | A | F |
| 4 | C | F | | |
| 5 | C | D | C | D |
| 6 | B | F | A | F |
| 7 | A | F | A | F |
| 8 | A | F | B | F |
| 9 | A | F | A | F |
| 10 | A | F | A | E |
| 11 | A | F | A | E |
| 12 | C | F | B | E |
| 13 | C | F | C | F |
| 14 | C | F | C | E |
| 15 | C | E | C | E |
| 16 | C | D | C | D |
| 17 | C | D | C | D |
| 18 | C | F | B | D |
| 19 | G | | | |
| 20 | G | | | |
| 21 | C | F | C | F |
| 22 | C | F | C | D |
| 23 | C | F | C | D |
| 24 | C | F | C | D |
| 25 | C | F | C | D |
| 26 | C | F | C | D |
| 27 | C | F | C | E |
| 28 | B | F | B | D |
| 29 | C | F | C | E |
| 30 | G | | | |
| 31 | G | | | |
| 32 | C | F | C | D |
| 33 | C | F | C | D |
| 34 | G | | | |
| 35 | G | | | |

TABLE 4-continued

Activity of compounds on beta-arrestin signaling and on inhibition of cAMP formation.

| Compound No. | β-arr. EC$_{50}$ | β-arr Max. Resp. | cAMP EC$_{50}$ | cAMP Max. Resp. |
|---|---|---|---|---|
| 36 | G | | | |
| 37 | C | F | C | D |
| 38 | C | F | C | D |
| 39 | G | | | |
| 40 | C | D | | |
| 41 | C | F | | |
| 42 | B | E | C | D |
| 43 | B | F | C | D |
| 44 | C | F | C | E |
| 45 | G | | | |
| 46 | G | | | |
| 47 | G | | | |
| 48 | C | F | C | E |
| 49 | C | F | C | F |
| 50 | C | F | B | D |
| 51 | C | F | B | F |
| 52 | A | F | A | F |
| 53 | C | F | C | F |
| 54 | C | F | C | E |
| 55 | C | F | B | E |
| 56 | C | F | B | E |
| 57 | C | F | C | E |
| 58 | C | F | C | D |
| 59 | C | F | C | F |
| 60 | A | F | A | E |
| 61 | C | F | C | E |
| 62 | C | F | C | D |
| 63 | C | F | C | E |
| 64 | B | F | B | D |
| 65 | C | F | C | E |
| 66 | C | F | C | E |
| 67 | C | F | B | E |
| 68 | C | F | B | E |
| 69 | C | F | B | D |
| 70 | C | F | C | E |
| 71 | C | F | C | D |
| 72 | B | F | A | D |
| 73 | C | F | C | D |
| 74 | C | F | C | E |
| 75 | B | F | A | E |
| 76 | C | F | C | D |
| 77 | C | F | C | D |
| 78 | B | F | A | E |
| 79 | C | F | C | D |
| 80 | C | E | C | D |
| 81 | C | E | C | D |
| 82 | C | D | C | D |
| 83 | C | D | C | D |
| 84 | C | E | C | D |
| 85 | C | D | C | D |
| 86 | C | D | C | D |
| 87 | C | F | C | D |
| 88 | C | E | C | D |
| 89 | B | F | C | D |
| 90 | C | D | C | D |
| 91 | C | F | C | D |
| 92 | B | F | C | D |
| 93 | B | E | C | D |
| 94 | A | F | A | D |
| 95 | C | F | C | D |
| 96 | C | F | C | D |
| 97 | B | F | B | D |
| 98 | C | E | C | D |
| 99 | A | E | A | D |
| 100 | A | F | C | D |
| 101 | B | F | A | D |
| 102 | C | F | B | E |
| 103 | C | F | B | D |
| 104 | B | F | B | D |
| 105 | B | F | B | D |
| 106 | B | F | A | D |
| 107 | C | F | C | D |
| 108 | C | F | C | E |
| 109 | C | F | A | E |
| 110 | C | F | C | F |
| 111 | C | F | | |
| 112 | G | | | |
| 113 | C | F | | |
| 114 | C | D | | |
| 115 | C | E | | |
| 116 | C | F | | |
| 117 | C | F | | |
| 118 | B | E | C | D |
| 119 | C | E | C | D |
| 120 | C | F | C | F |
| 121 | A | F | A | E |
| 122 | A | F | A | F |
| 123 | B | F | A | E |
| 124 | A | F | A | E |
| 125 | A | F | A | F |
| 126 | A | F | A | E |
| 127 | A | F | B | E |
| 128 | A | F | B | E |
| 129 | A | F | B | E |
| 130 | A | F | B | E |
| 131 | B | F | B | D |
| 132 | C | F | B | D |
| 133 | C | F | C | E |
| 134 | C | F | C | D |
| 135 | B | F | A | D |
| 136 | C | F | C | D |
| 137 | C | D | C | D |
| 138 | C | D | C | D |
| 139 | C | F | C | E |
| 140 | G | | | |
| 141 | C | D | C | D |
| 142 | C | D | C | D |
| 143 | C | D | C | D |
| 144 | C | E | C | D |
| 145 | C | F | B | E |
| 146 | C | F | C | D |
| 147 | C | F | C | D |
| 148 | B | F | C | E |
| 149 | C | F | C | E |
| 150 | A | F | A | E |
| 151 | C | F | C | D |
| 152 | C | F | B | E |
| 153 | C | F | C | D |
| 154 | A | F | A | E |
| 155 | B | F | B | D |
| 156 | C | F | C | E |
| 157 | C | F | C | E |
| 158 | B | F | A | D |
| 159 | B | F | B | E |
| 160 | B | F | B | F |
| 161 | B | F | B | E |
| 162 | C | F | C | E |
| 163 | B | F | A | E |
| 164 | B | F | A | E |
| 165 | C | F | B | F |
| 166 | C | F | C | E |
| 167 | A | F | B | F |
| 168 | C | F | C | F |
| 169 | A | F | A | F |
| 170 | B | F | A | E |
| 171 | B | F | B | E |
| 172 | B | F | A | E |
| 173 | A | F | A | F |
| 174 | B | F | B | E |
| 175 | C | F | C | E |
| 176 | B | F | B | F |
| 177 | C | F | C | E |
| 178 | A | F | B | D |
| 179 | B | F | A | D |
| 180 | C | F | C | E |
| 181 | C | E | C | D |
| 182 | C | E | C | D |
| 183 | C | E | C | D |

TABLE 4-continued

Activity of compounds on beta-arrestin signaling and on inhibition of cAMP formation.

| Compound No. | β-arr. EC$_{50}$ | β-arr Max. Resp. | cAMP EC$_{50}$ | cAMP Max. Resp. |
|---|---|---|---|---|
| 184 | C | F | C | D |
| 185 | B | F | C | D |
| 186 | C | E | C | D |
| 187 | C | F | C | E |
| 188 | C | F | B | E |
| 189 | B | F | B | F |
| 190 | B | F | A | F |
| 191 | B | F | B | E |
| 192 | C | F | C | D |
| 193 | B | F | C | F |
| 194 | B | F | B | D |
| 195 | B | F | C | D |
| 196 | A | F | A | F |
| 197 | B | F | B | F |
| 198 | B | F | B | F |
| 199 | A | F | B | E |
| 200 | A | F | A | E |
| 201 | C | F | C | F |
| 202 | C | F | C | E |
| 203 | C | F | A | D |
| 204 | B | F | B | F |
| 205 | B | F | A | F |
| 206 | B | F | B | E |
| 207 | B | F | B | D |
| 208 | C | F | B | F |
| 209 | B | F | B | D |
| 210 | C | F | B | E |
| 211 | C | F | C | E |
| 212 | C | F | C | E |
| 213 | C | F | C | D |
| 214 | C | F | B | E |
| 215 | B | F | C | D |
| 216 | A | F | C | D |
| 217 | B | F | C | D |
| 218 | B | E | C | D |
| 219 | B | F | A | F |
| 220 | C | F | B | D |
| 222 | C | F | B | D |
| 223 | C | F | B | E |
| 224 | C | F | A | F |
| 225 | C | F | C | F |
| 226 | C | F | C | F |
| 227 | C | F | C | F |
| 228 | C | F | C | F |
| 229 | C | F | C | F |
| 230 | C | F | C | F |
| 231 | C | E | C | E |
| 232 | C | F | C | F |
| 233 | C | F | C | F |
| 234 | C | F | C | F |
| 235 | C | F | C | F |
| 236 | C | F | C | F |
| 221 | C | D | C | D |
| 237 | C | E | C | D |
| 238 | C | E | C | D |
| 239 | C | E | C | D |
| 240 | C | D | C | E |
| 241 | C | F | C | E |
| 242 | C | D | C | D |
| 243 | C | F | C | E |
| 244 | A | F | A | D |
| 245 | C | D | C | D |
| 246 | B | F | B | D |
| 247 | C | F | C | E |
| 248 | C | F | C | E |
| 249 | C | F | C | E |
| 250 | C | F | C | D |
| 251 | C | F | C | D |
| 252 | C | F | C | E |
| 253 | C | F | C | E |
| 254 | C | D | C | E |
| 255 | C | D | C | F |
| 256 | C | D | C | D |
| 257 | C | F | C | D |
| 258 | C | E | C | F |
| 259 | C | D | C | D |
| 260 | C | D | C | D |
| 261 | B | F | C | D |
| 262 | C | E | C | D |
| 263 | B | F | B | D |
| 264 | C | E | B | F |
| 265 | C | F | C | E |
| 266 | C | E | C | D |
| 267 | C | D | C | E |
| 268 | C | D | C | F |
| 269 | C | F | C | D |
| 270 | C | D | C | D |
| 271 | C | F | B | E |
| 272 | C | D | C | F |
| 273 | C | D | C | D |
| 274 | C | F | B | D |
| 275 | C | D | C | D |
| 276 | C | E | B | D |
| 277 | C | E | C | D |
| 278 | C | F | B | F |
| 279 | C | D | C | F |
| 280 | C | F | C | E |
| 281 | B | F | A | D |
| 282 | B | F | B | D |
| 283 | C | D | C | F |
| 284 | C | D | C | E |
| 285 | B | F | C | E |
| 286 | C | D | C | D |
| 287 | B | F | A | D |
| 288 | C | F | C | E |
| 289 | B | F | C | D |
| 290 | A | F | A | D |
| 291 | C | D | C | F |
| 292 | C | D | C | E |
| 293 | C | F | B | F |
| 294 | C | D | C | F |
| 295 | C | D | C | D |
| 296 | C | D | C | D |
| 297 | C | E | C | E |
| 298 | C | F | A | F |
| 299 | B | F | A | F |
| 300 | C | E | C | F |
| 301 | B | F | A | E |
| 302 | C | E | C | D |
| 303 | C | D | C | E |
| 304 | C | D | C | D |
| 305 | B | F | B | F |
| 306 | C | D | C | F |
| 307 | C | D | C | F |
| 308 | C | E | C | F |
| 309 | C | E | C | D |
| 310 | C | F | B | F |
| 311 | C | F | B | F |
| 312 | A | F | A | F |
| 313 | C | F | B | E |
| 326 | A | D | A | D |
| 327 | A | D | A | D |
| 328 | A | D | A | D |
| 329 | A | D | A | D |
| 330 | A | D | A | D |
| 331 | A | D | A | D |
| 332 | A | D | A | D |
| 333 | A | D | A | D |
| 334 | A | D | A | D |
| 335 | A | D | A | D |
| 336 | A | D | A | D |
| 337 | A | D | A | D |
| 338 | A | D | A | D |
| 339 | A | D | A | D |
| 340 | A | D | A | D |
| 341 | A | D | A | D |
| 343 | A | D | A | D |
| 344 | A | D | A | D |

TABLE 4-continued

Activity of compounds on beta-arrestin signaling and on inhibition of cAMP formation.

| Compound No. | β-arr. $EC_{50}$ | β-arr Max. Resp. | cAMP $EC_{50}$ | cAMP Max. Resp. |
|---|---|---|---|---|
| 345 | A | D | A | D |
| 346 | A | D | A | D |
| 347 | A | D | A | D |
| 348 | A | D | A | D |
| 349 | A | D | A | D |
| 350 | A | D | A | D |
| 351 | A | D | A | D |
| 352 | A | D | A | D |
| 353 | A | D | A | D |
| 354 | A | D | A | D |
| 355 | A | D | A | D |
| 356 | A | D | A | D |
| 357 | A | D | A | D |
| 358 | A | D | A | D |
| 359 | A | D | A | D |
| 360 | A | D | A | D |
| 361 | A | D | A | D |
| 362 | A | D | A | D |
| 363 | A | D | A | D |
| 364 | A | D | A | D |
| 365 | A | D | A | D |
| 366 | A | D | A | D |
| 368 | A | D | A | D |
| 369 | A | D | A | D |
| 370 | A | D | A | D |
| 371 | A | D | A | D |
| 372 | A | D | A | D |
| 373 | A | D | A | D |
| 374 | A | D | A | D |
| 375 | A | D | A | D |
| 376 | A | D | A | D |
| 377 | A | D | A | D |
| 378 | A | D | A | D |
| 379 | A | D | A | D |
| 380 | A | D | A | D |
| 381 | A | D | A | D |
| 382 | A | D | A | D |
| 388 | A | D | A | D |
| 389 | A | D | A | D |
| 390 | A | D | A | D |
| 391 | A | D | A | D |
| 392 | A | D | A | D |
| 393 | A | D | A | D |
| 395 | A | D | A | D |
| 396 | A | D | A | D |
| 400 | A | D | A | D |
| 401 | A | D | A | D |
| 402 | A | D | A | D |
| 403 | A | D | A | D |
| 404 | A | D | A | D |
| 405 | A | D | A | D |
| 406 | A | D | A | D |
| 407 | A | D | A | D |
| 408 | A | D | A | D |
| 409 | A | D | A | D |
| 410 | A | D | A | D |
| 411 | A | D | A | D |
| 412 | A | D | A | D |
| 413 | A | D | A | D |
| 414 | A | D | A | D |
| 415 | A | D | A | D |
| 417 | A | D | A | D |
| 420 | A | D | A | D |
| 421 | A | D | A | D |
| 422 | A | D | A | D |
| 423 | A | D | A | D |
| 424 | C | F | C | D |
| 425 | C | F | B | E |
| 443 | C | F | C | D |
| 444 | C | F | C | D |
| 445 | C | E | C | D |
| 446 | C | F | C | E |
| 447 | C | D | C | D |
| 448 | C | F | C | D |
| 449 | C | F | C | D |
| 450 | C | F | C | E |
| 451 | C | F | C | D |
| 452 | C | E | C | D |
| 453 | C | D | C | D |
| 454 | C | E | C | D |
| 455 | C | E | C | D |
| 456 | C | F | C | E |
| 457 | C | F | C | E |
| 458 | C | E | C | D |
| 459 | C | F | C | D |
| 460 | C | F | C | F |
| 461 | C | F | C | E |
| 462 | C | E | C | D |
| 463 | C | D | C | D |
| 464 | C | E | C | E |
| 465 | C | E | C | D |
| 466 | C | F | C | D |
| 467 | C | F | C | D |
| 468 | C | F | C | F |
| 469 | C | F | C | D |
| 470 | C | F | C | E |
| 471 | C | F | C | D |
| 473 | C | E | C | D |
| 474 | C | D | C | D |
| 475 | C | F | C | D |
| 476 | C | E | C | D |
| 477 | C | F | C | D |
| 478 | C | F | C | D |
| 479 | C | F | C | D |
| 480 | C | D | C | D |
| 481 | C | D | C | D |
| 482 | C | D | C | D |
| 483 | C | D | C | D |

Legend:
The first column provides the compound number (identified elsewhere herein) of the compound tested.
The second column provides $EC_{50}$ values for β-arrestin recruitment;
the third column provides maximal response values for β-arrestin recruitment;
the fourth column provides $EC_{50}$ values for adenylyl cyclase inhibition; and
the fifth column provides maximal response values for adenylyl cyclase inhibition.
$EC_{50}$ values are coded as follows: A represents an $EC_{50}$ <700 nM; B represents an $EC_{50}$ between 700 nM and 2.1 μM; and C represents an EC 50 >2.1 μM.
Maximal response values are coded as follows: D represents a maximal response of <40%; E represents a maximal response of 40-60%; and F represents a maximal response of >60%. G represents <50% inhibition of β-arrestin recruitment at a static concentration of 5 μM, for compounds that were not tested for adenylyl cyclase inhibition..

Thus, in addition to previous approaches in which an orthosteric ligand is modified to endow it with selective signal bias, the compositions and methods described herein provide an improved alternative which combines the benefits of allosteric modulation with the advantage of selective signal bias by the allosteric modulator.

Unless otherwise defined, all technical and scientific terms used herein have the same meaning as commonly understood by one of ordinary skill in the art. Although methods and materials similar or equivalent to those described herein can be used in the practice or testing of the compositions and compounds described herein, suitable methods and materials are described below. All publications, patent applications, patents, and other references mentioned herein are incorporated by reference in their entirety. In addition, the materials, methods, and examples are illustrative only not intended to be limiting. Other features and advantages of the compositions and compounds described herein will be apparent from the detailed description, reaction schemes, examples and claims.

Reaction Schemes

The following representative schemes illustrate how compounds described herein can be prepared. The specific solvents and reaction conditions referred to are illustrative and are not intended to be limiting. Compounds not described are either commercially available or are readily prepared by one skilled in the art using available starting materials.

Scheme 1: General Method 1 for synthesis of compounds

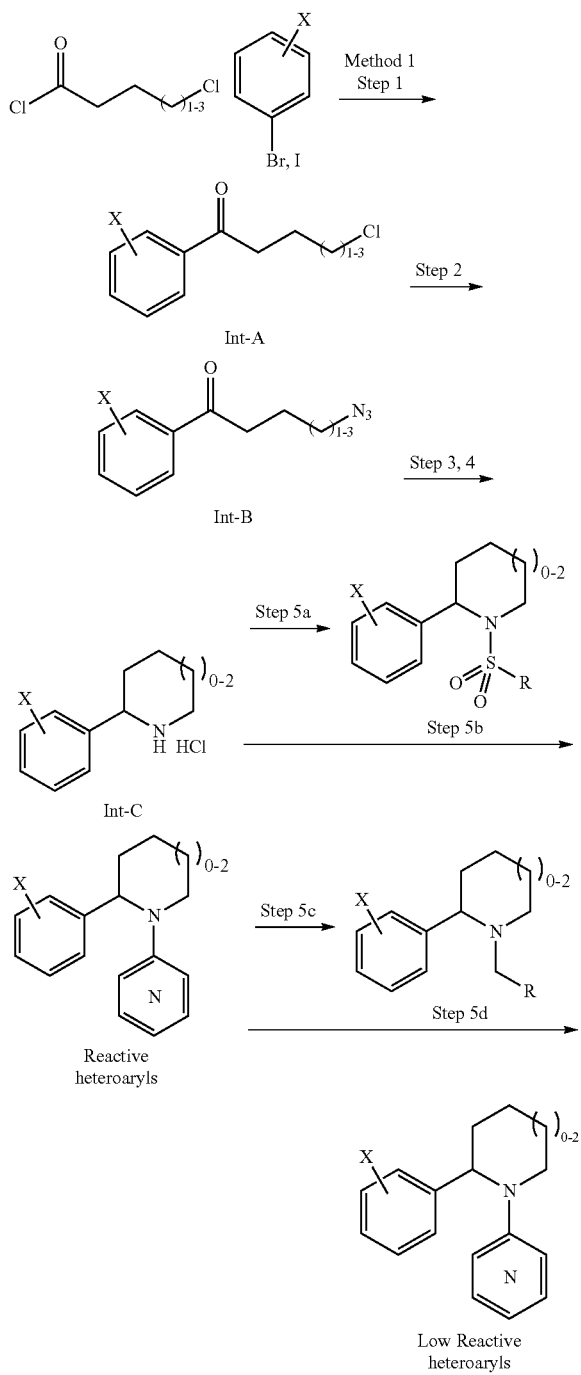

Method 1
Step 1:

Magnesium powder (1.2 eq) was added to a round-bottom flask and flame-dried under vacuum. Once cooled down to room temperature, the vessel was back-filled with nitrogen, a crystal of iodine was added and the flask was flame-dried again under vacuum to sublime the iodine. Once the flask has cooled down to room temperature, THF (1.0 M vs. aryl iodide) was added followed by the aryl iodide (1.0 eq). The resulting suspension was then refluxed for 30 min before being cooled down to room temperature and then 0° C.

A separate flask was flame-dried under vacuum and back-filled with nitrogen before being charged with CuI (1.1 eq) and 4-chlorobutyryl chloride (n=1, 1.1 eq) or 5-chlorovaleryl chloride (n=2, 1.1 eq) or 6-chlorocaproyl chloride (n=3, 1.1 eq) in THF (0.5 M vs. aryl iodide) and cooled down to 0° C. To this solution was slowly transferred via cannula under nitrogen the freshly prepared Grignard reagent. The resulting mixture was allowed to warm up to room temperature and stirred until completion (approximately 2 hours) as determined by mass spectral analysis. Upon completion, the reaction mixture was quenched with saturated aqueous $NH_4Cl$ and extracted with diethyl ether (3 times). The combined organic layers were washed with saturated aqueous NaCl, dried over $Na_2SO_4$, filtered and the volatiles were evaporated under reduced pressure. The crude residue was purified by flash chromatography on silica.

Step 2:

To an oven-dried vial equipped with a Teflon septum and magnetic stir bar was added the required alkyl chloride (1.0 eq) in N,N-dimethylacetamide (0.4 M vs. alkyl chloride) and $NaN_3$ (2.0 eq). The vial was sealed and the reaction mixture was heated to 60° C. for 2 hours. Upon completion of the reaction, the solution was cooled down to room temperature, diluted with saturated aqueous NaCl and extracted with $Et_2O$ (3 times). The combined organic layers were washed with sat. aq. NaCl, dried over $Na_2SO_4$, filtered and the volatiles were evaporated under reduced pressure. The crude residue was purified by flash chromatography on silica.

Step 3:

An oven-dried vial equipped with a Teflon septum and magnetic stir bar was charged with the appropriate azide (1.0 eq) in THF (0.2 M vs. azide). Triphenylphosphine (2.0 eq) was then added and the reaction mixture was stirred for 2 hours. Water was added to the reaction mixture (1.0 M vs. azide) and the reaction mixture was stirred for 16 hours. The reaction mixture was evaporated to dryness and the crude residue was dissolved in $Et_2O$ before being cooled down to 0° C. The precipitate was filtered out and this process was repeated two more times before the filtrate was concentrated under reduced pressure. The crude residue was used in the next step without further purification.

Step 4:

The crude amino ketone was taken up in MeOH (0.2 M vs. ketone) and cooled down to −20° C. before adding $NaBH_4$ (10.0 eq) in one portion. The resulting suspension was allowed to warm to room temperature and stirred until completion before being quenched with sat. aq. $NaHCO_3$. The reaction mixture was extracted with DCM (3 times). The combined organic layers were washed with sat. aq. NaCl, dried over $Na_2SO_4$, filtered and the volatiles were evaporated under reduced pressure. The crude residue was dissolved in $Et_2O$ (0.1 M vs. amine) and HCl was added (10.0 eq, 2.0 N in $Et_2O$) to precipitate the desired material as the hydrochloride salt.

Step 5a: Synthesis of Sulfonamides.

An oven-dried vial equipped with a Teflon septum and magnetic stir bar was charged with the amine hydrochloride salt (1.0 eq), DCE (0.1 M vs. amine) and N,N-diisopropylethylamine (3.0 eq). The reaction mixture was cooled down to 0° C. before the appropriate sulfonyl chloride (1.2 eq) was added. The reaction mixture was stirred while warming up to room temperature. Upon completion of the reaction, the reaction mixture was diluted with 0.1 N aq. HCl and extracted with DCM (3 times). The combined organic layers were washed with sat. aq. NaCl, dried over Na$_2$SO$_4$, filtered and the solvents were evaporated under reduced pressure. The crude residue was purified by preparative LC-MS.

Step 5b: Synthesis of Heteroanilines:

An oven-dried vial equipped with a Teflon septum and magnetic stir bar was charged with the amine hydrochloride salt (1.0 eq), 1-butanol (0.1 M vs. amine), N,N-diisopropylethylamine (3.0 eq) and the appropriate chloro-heteroarene (1.2 eq). The reaction mixture was stirred at 50° C. for 14 h. Upon completion of the reaction, solvents were evaporated under reduced pressure. The crude residue was purified by preparative LC-MS.

Step 5c: Synthesis of Benzylic Amines:

An oven-dried vial equipped with a Teflon septum and magnetic stir bar was charged with the amine hydrochloride salt (1.0 eq), MeCN (0.1 M vs. amine), Cs$_2$CO$_3$ (3.0 eq) and KI (0.1 eq). The appropriate benzyl bromide (1.0 eq) was added dropwise (neat or as 1 M solution in MeCN). The reaction mixture was stirred at 80° C. Upon completion of the reaction, the reaction mixture was cooled down to room temperature, diluted with sat. aq. Na$_2$CO$_3$ and extracted with EtOAc (3 times). The combined organic layers were washed with sat. aq. NaCl, dried over Na$_2$SO$_4$, filtered and the solvents were evaporated under reduced pressure. The crude residue was purified by preparative LC-MS.

Step 5d: Synthesis of Poorly Reactive Heteroanilines:

An oven-dried vial equipped with a Teflon septum and magnetic stir bar was charged with the amine hydrochloride salt (1.0 eq), anhydrous NMP (0.1 M vs. amine), N,N-diisopropylethylamine (3.0 eq), the appropriate chloro-heteroarene (5.0 eq) and potassium fluoride on alumina (5.0 eq, 40% w/w loading). The reaction mixture was stirred at 180° C. for 18 h. Upon completion of the reaction, solids were filtered off and the solvents were evaporated under reduced pressure. The crude residue was purified by preparative LC-MS.

Scheme 2: General Method 2 for synthesis of int-A

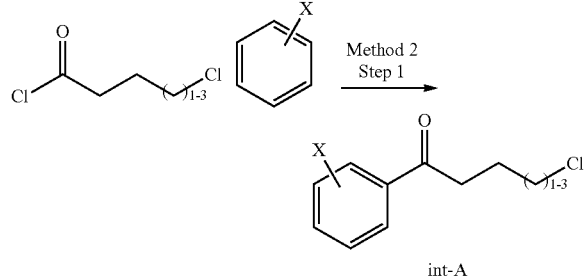

int-A

Method 2

Step 1:

Int-A can also be intercepted via the following route, with final compounds being attained by following the Method A1 Steps 2-5.

A round-bottom flask was flame-dried under vacuum and backfilled with nitrogen before being charged with the required arene (1.0 eq) in DCM (1 M vs. ketone). Aluminum trichloride (1.1 eq) was added in one portion followed by the dropwise addition of 4-chlorobutyryl chloride (n=1, 1.1 eq) or 5-chlorovaleryl chloride (n=2, 1.1 eq) or 6-chlorocaproyl chloride (n=3, 1.1 eq). The reaction mixture was heated to reflux for 2 hours. Upon completion of the reaction, the reaction mixture was poured onto cold 3N aq. HCl (2×V$_{DCM}$) and extracted with DCM (3 times). The combined organic layers were washed with sat. aq. NaHCO$_3$ (1 time) and sat. aq. NaCl (1 time), dried over Na$_2$SO$_4$, filtered and the solvents were evaporated under reduced pressure. The crude residue was purified by flash chromatography on silica.

The final product was obtained following steps 2, 3, 4, 5a, 5b, 5c or 5d from Method 1.

Scheme 3: General Method 3 for synthesis of int-C

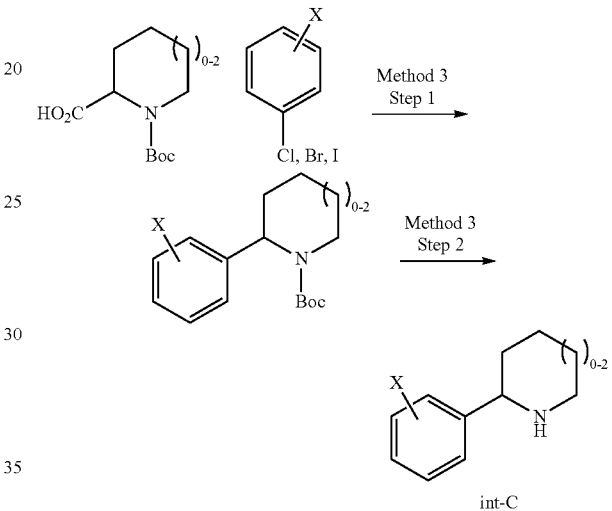

int-C

Example Acids Used in Conjunction with Scheme 3

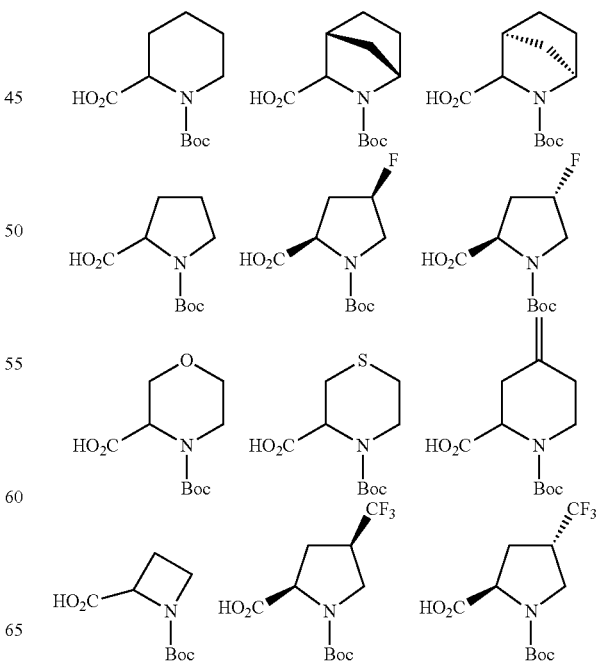

-continued

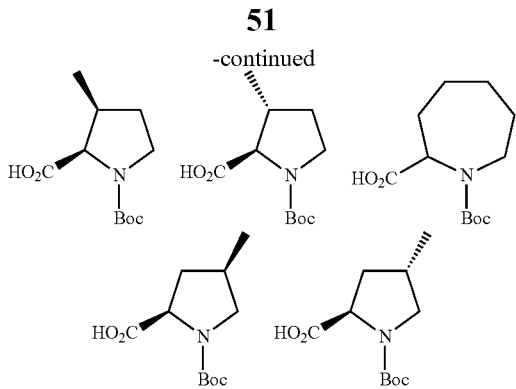

Example Aryl Bromides Used in Conjunction with Scheme 3

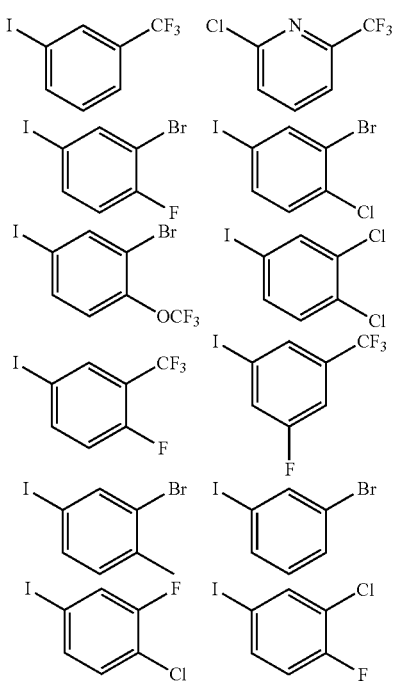

Method 3

Int-C can also be intercepted via the following route, with final compounds being attained by following Method 1, steps 5a-d.

Step 1:

An oven-dried vial equipped with a Teflon septum and magnetic stir bar was charged with Ir[dF(CF₃)ppy]₂(dtbbpy)PF₆ (0.01 eq), NiCl₂.glyme (0.1 eq), 4,4'-di-tert-butyl-2,2'-bipyridyl (0.15 eq), the desired aryl halide (1.0 eq), the appropriate Boc-protected amino acid (1.5 eq), Cs₂CO₃ (1.5 eq) and DMF (0.02 M vs. aryl bromide). The reaction mixture was degassed by bubbling with nitrogen for 20 min, then irradiated with two 26 W fluorescent lamps (at approximately 2 cm away from the light source). After 72 h, the reaction mixture was diluted with sat. aq. NaHCO₃ and extracted with Et₂O (3 times). The combined organic layers were washed with water (1 time) and sat. aq. NaCl (1 time), dried over Na₂SO₄ and concentrated under reduced pressure. The crude residue was purified by flash chromatography on silica.

Step 2:

An oven-dried vial equipped with a Teflon septum and magnetic stir bar was charged with the Boc-protected amine (1.0 eq) and dioxane (0.1 M vs. carbamate). 4.0 N HCl in dioxane (excess) was added and the reaction mixture was stirred until complete deprotection was achieved. Upon completion of the reaction, the reaction mixture was diluted with sat. aq. Na₂CO₃ and extracted with EtOAc (3 times). The combined organic layers were washed with sat. aq. NaCl, dried over Na₂SO₄, filtered and the solvents were evaporated under reduced pressure. The crude residue was dissolved in Et₂O (0.1 M vs. amine) and HCl was added (10.0 eq, 2.0 N in Et₂O) to precipitate the desired material as the hydrochloride salt.

Scheme 4: General Method 4 for synthesis of int-C2

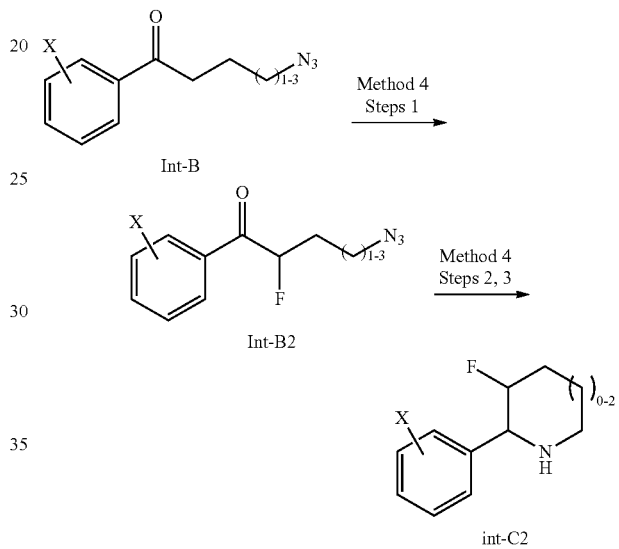

Method 4

Int-B can be attained from either Method 1 or Method 2, with final compounds deriving from Int-C2 being attained by following the procedures detailed in Step 5a, 5b (80° C. instead of 50° C.), 5c or 5d from Method 1.

Step 1:

A round-bottom flask was flame-dried under vacuum and backfilled with nitrogen before being charged with the required azido aryl ketone (1.0 eq) in DCM (0.2 M vs. ketone). Triethylamine (2.0 eq) and triethylsilyltrifluoromethanesulfonate (2.0 eq) were sequentially added. The reaction mixture was stirred until completion (approximately 2 hours) before being quenched with sat. aq. NaHCO₃. The reaction mixture was extracted with DCM and the combined organic layers were washed with sat. aq. NaCl, dried over Na₂SO₄ and quickly pushed through a short plug of silica. Volatiles were then evaporated under reduced pressure. The crude residue was then dissolved in MeCN (0.2 M vs. ketone), Selectfluor® was added (1.0 eq) and the resulting solution was stirred at room temperature. Upon completion of the reaction, water was added and the reaction mixture was extracted with EtOAc (3 times). The combined organic layers were washed with sat. aq. NaCl, dried over Na₂SO₄, filtered and the volatiles were evaporated under reduced pressure. The crude residue was purified by flash chromatography.

Step 2:

An oven-dried vial equipped with a Teflon septum and magnetic stir bar was charged with the appropriate azide (1.0 eq) in THF (0.2 M vs. azide). Triphenylphosphine (2.0 eq) was then added and the reaction mixture was stirred for 2 hours. Water was added to the reaction mixture (1.0 M vs. azide) and the reaction mixture was stirred for 16 hours. The reaction mixture was evaporated to dryness and the crude residue was dissolved in $Et_2O$ before being cooled down to 0° C. The precipitate was filtered out and this process was repeated two more times before the filtrate was concentrated under reduced pressure. The crude residue was used in the next step without further purification.

Step 3:

An oven-dried vial equipped with a Teflon septum and magnetic stir bar was charged with the amino ketone (1.0 eq) and DCE (0.1 M vs. amine). The reaction mixture was stirred for 1 hour at room temperature before STAB (2.0 eq) was added in one portion. The reaction mixture was stirred for 16 hours at room temperature. Upon completion of the reaction, the reaction mixture was diluted with sat. aq. $Na_2CO_3$ and extracted with EtOAc (3 times). The combined organic layers were washed with sat. aq. NaCl, dried over $Na_2SO_4$, filtered and the volatiles were evaporated under reduced pressure. The crude amine was purified by preparative LC-MS or salted out as the hydrochloride (see Method 1, Step 4).

Scheme 5: General Method 5 for synthesis of int-C3

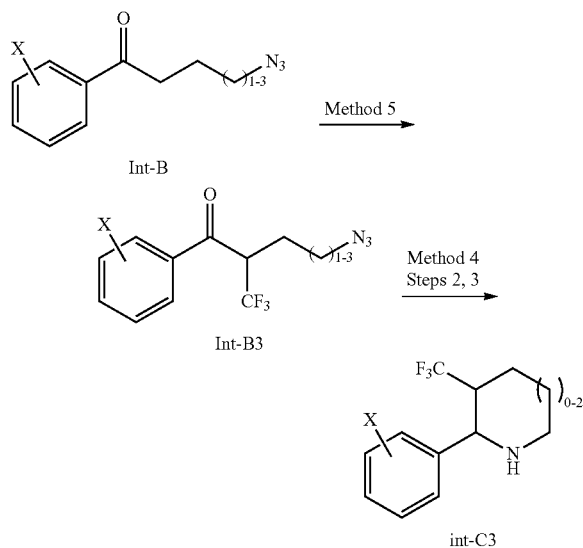

Method 5

Int-B can be attained from either Method 1 or Method 2. Int-C3 can be attained from Int-B3 by following steps 2 and 3 of Method 4. Final compounds deriving from Int-C3 are attained by following the procedures detailed in steps 5a, 5b (80° C. instead of 50° C.), 5c or 5d of Method 1.

A round-bottom flask was flame-dried under vacuum and backfilled with nitrogen before being charged with the required azido aryl ketone (1.0 eq) in DCM (0.2 M vs. ketone). Triethylamine (2.0 eq) and triethylsilyltrifluoromethanesulfonate (2.0 eq) were sequentially added. The reaction mixture was stirred until completion (approximatively 2 hours) before being quenched with sat. aq. $NaHCO_3$. The reaction mixture was extracted with DCM and the combined organic layers were washed with sat. aq. NaCl, dried over $Na_2SO_4$ and quickly pushed through a short plug of silica. Volatiles were then evaporated under reduced pressure. An oven-dried vial was charged with Togni's reagent (3,3-Dimethyl-1-(trifluoromethyl)-1,2-benziodoxole, 1.5 eq), and CuSCN (0.1 eq) under a nitrogen atmosphere. To these solids were added a solution of the silyl enol ether (1.0 eq) in DMA (0.1 M vs. silyl enol ether). The vial was sealed and stirred at 80° C. for 12 hours. Upon completion of the reaction, sat. aq. NaCl was added and the reaction mixture was extracted with $Et_2O$ (3 times). The combined organic layers were washed with sat. aq. NaCl, dried over $Na_2SO_4$, filtered and the volatiles were evaporated under reduced pressure. The crude residue was purified by flash chromatography.

Scheme 6: General Method 6 for synthesis of int-C4

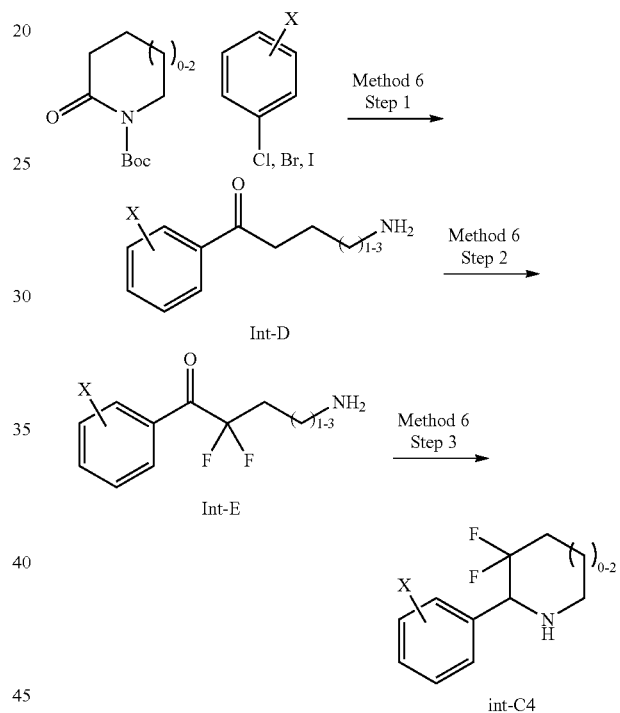

Method 6

Step 1:

A round-bottom flask was flame-dried under vacuum and backfilled with nitrogen before being charged with the required halo arene (1.3 eq) in THF (2 M vs. arene). The reaction mixture was cooled down to −15° C. (ice-acetone bath) before i-PrMgCl (1.2 eq, 2.0 M in THF) was added dropwise over 10 minutes. The reaction mixture was stirred for 3 hours while slowly warming up to 0° C. In a separate round-bottom flask, flame-dried under vacuum and backfilled with nitrogen, was added N-Boc-2-piperidone (1.0 eq) and THF (0.4 M vs. piperidone) and the reaction mixture was cooled down to −78° C. (dry ice-acetone bath). The Grignard reagent was added dropwise via cannula to the piperidone over ~20 minutes. Once the transfer was complete, the reaction mixture was stirred for an additional hour at −78° C. before 4.0 N HCl in dioxane (100.0 eq) was added. The cooling bath was removed and the reaction mixture was stirred for 18 h. Upon completion of the reaction, volatiles were evaporated to dryness under reduced pressure. The crude residue was diluted with sat. aq. Na$_2$CO$_3$ and extracted with EtOAc (3 times). The combined organic layers were washed with sat. aq. NaCl, dried over Na$_2$SO$_4$, filtered and the volatiles were evaporated under reduced pressure. The crude residue was used without further purification.

Step 2:

An oven-dried vial equipped with a Teflon septum and magnetic stir bar was charged with the appropriate amino ketone (1.0 eq) and a 1:1 MeOH:H$_2$O mixture (0.1 M vs. ketone). Selectfluor® (4.0 eq) was added and the reaction mixture was heated to 80° C. for 16 hours. Upon completion of the reaction, the reaction mixture was cooled down to room temperature and the volatiles were evaporated to dryness under reduced pressure. The crude residue was diluted with sat. aq. NaCl and extracted with Et$_2$O (3 times). The combined organic layers were washed with sat. aq. NaCl, dried over Na$_2$SO$_4$, filtered and the volatiles were evaporated under reduced pressure. The crude residue was used without further purification.

Step 3:

An oven-dried vial equipped with a Teflon septum and magnetic stir bar was charged with the amino ketone (1.0 eq) and DCE (0.1 M vs. amine) before NaBH$_3$CN (1.5 eq) was added in one portion. The reaction mixture was stirred for 3 hours at room temperature. Upon completion of the reaction, the reaction mixture was diluted with sat. aq. Na$_2$CO$_3$ and extracted with EtOAc (3 times). The combined organic layers were washed with sat. aq. NaCl, dried over Na$_2$SO$_4$, filtered and the volatiles were evaporated under reduced pressure. The crude amine was purified by preparative LC-MS or salted out as the hydrochloride (see Method 1, Step 4).

Final compounds are obtained by following the procedures detailed in steps 5a, 5b (80° C. instead of 50° C.), 5c or 5d from Method 1.

Scheme 7: General Method 7 for synthesis of int-C5

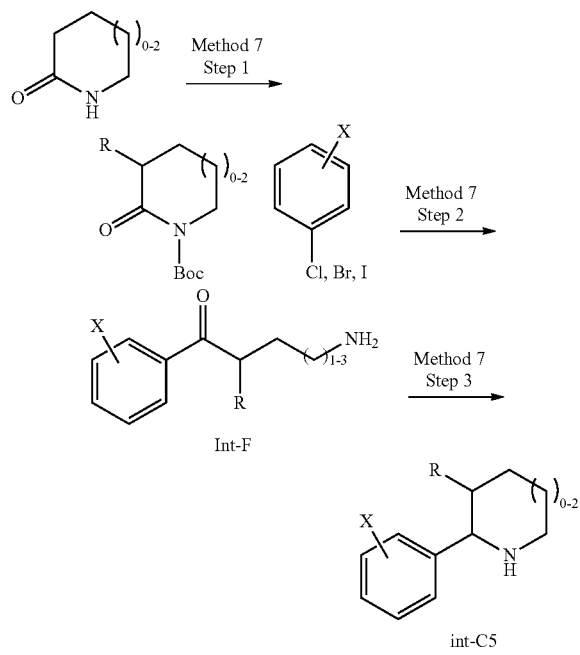

Method 7

Step 1:

A round-bottom flask was flame-dried under vacuum and backfilled with nitrogen before being charged with 2-piperidone (1.1 eq) in THF (0.5 M vs. piperidone). The reaction mixture was cooled down to –78° C. (dry ice-acetone bath) before n-BuLi (2.2 eq, 1.0 M in THF) was added dropwise over 15 minutes. The reaction mixture was stirred for 15 minutes at –78° C. then 45 minutes at 0° C. The reaction mixture was cooled down to –78° C. the desired alkyl halide (1.0 eq) was added dropwise as a 1.0 M solution in THF. The reaction mixture was stirred at –78° C. for 15 minutes (iodide) or 1 hour (bromide) before di-tert-butyl-dicarbonate (1.35 eq) was added dropwise as a 1.0 M solution in THF. The reaction mixture was stirred for 15 minutes at –78° C. before being quenched with sat. aq. NH4Cl and the aqueous layer was extracted with Et2O (3 times). The combined organic layers were washed with sat. aq. NaCl, dried over Na2SO4, filtered and the volatiles were evaporated under reduced pressure. The crude residue was purified by flash chromatography on silica gel.

Step 2:

A round-bottom flask was flame-dried under vacuum and backfilled with nitrogen before being charged with the required halo arene (1.3 eq) in THF (2.0 M vs. arene). The reaction mixture was cooled down to –15° C. (ice-acetone bath) before i-PrMgCl (1.2 eq, 2.0 M in THF) was added dropwise over 10 minutes. The reaction mixture was stirred for 3 hours while slowly warming up to 0° C. In a separate round-bottom flask, flame-dried under vacuum and backfilled with nitrogen, was added the appropriate N-Boc-3-alkyl-2-piperidone (1.0 eq) and THF (0.4 M vs. piperidone) and the reaction mixture was cooled down to –78° C. (dry ice-acetone bath). The Grignard reagent was added dropwise via cannula to the piperidone over ~20 minutes. Once the transfer was complete, the reaction mixture was stirred for an additional 2 hours at –78° C. before TFA (5.0 eq) was added. The reaction mixture was removed from the cooling bath and stirred for 1 h. Upon reaching room temperature, volatiles were evaporated to dryness under reduced pressure. The crude residue was taken up in DCM (0.5 M vs ketone) and cooled down to 0° C. before TFA (half the volume of DCM) was added dropwise. The reaction mixture was stirred at room temperature until complete deprotection has occurred. Upon completion of the reaction, the volatiles were evaporated to dryness under reduced pressure. The crude residue was diluted with sat. aq. Na2CO3 and extracted with Et2O (3 times). The combined organic layers were washed with sat. aq. NaCl, dried over Na2SO4, filtered and the volatiles were evaporated under reduced pressure. The crude residue was used without further purification.

Step 3:

An oven-dried vial equipped with a Teflon septum and magnetic stir bar was charged with the amino ketone (1.0 eq) and DCE (0.1 M vs. amine). The reaction mixture was stirred for 1 hour at room temperature before STAB (2.0 eq) was added in one portion. The reaction mixture was stirred for 16 hours at room temperature. Upon completion of the reaction, the reaction mixture was diluted with sat. aq. Na2CO3 and extracted with EtOAc (3 times). The combined organic layers were washed with sat. aq. NaCl, dried over Na2SO4, filtered and the volatiles were evaporated under reduced pressure. The crude amine was purified by preparative LC-MS or salted out as the hydrochloride (see method 1, Step 4).

The final target was obtained following step 5a, 5b, 5c or 5d from Method 1.

Scheme 8: General Method 8 for synthesis of N-aryls

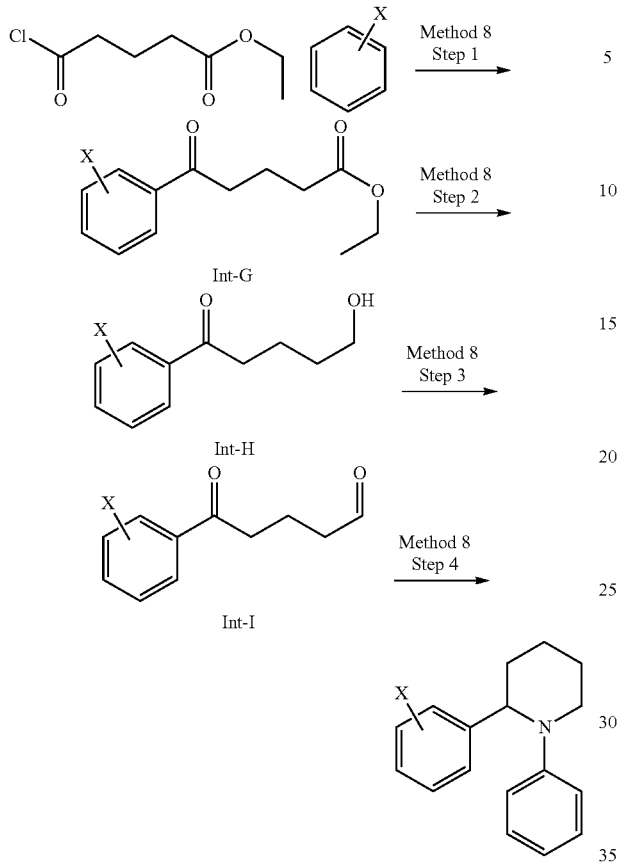

Method 8

Step 1:

A round-bottom flask was flame-dried under vacuum and backfilled with nitrogen before being charged with the required arene (1.0 eq) in 1,2-DCE (0.5 M vs. arene). Ethyl 5-chloro-5-oxopentanoate (1.1 eq) and anhydrous $AlCl_3$ (2.0 eq) were subsequently added to the reaction mixture. The resulting suspension was stirred at 70° C. for 2 hours. Upon completion of the reaction, as judged by TLC, the reaction mixture was cooled down to room temperature and poured onto ice. The layers were separated and the aqueous layer was extracted with DCM (2 times). The combined organic layers were washed with 1N aq. HCl (2 times), water and sat. aq. NaCl, dried over $Na_2SO_4$, filtered and the volatiles were evaporated under reduced pressure. The crude residue was used without further purification.

Step 2:

A round-bottom flask was flame-dried under vacuum and backfilled with nitrogen before being charged with $LiAlH_4$ (x g, 1.5 eq) in $Et_2O$ (0.4 M vs. Al). The previously obtained keto-ester (1.0 eq) in $Et_2O$ (0.5 M vs. ketone) was added dropwise over 30 minutes. Upon completion of the addition, the reaction mixture was refluxed and stirred for 5 h. After completion of the reaction, as judged by TLC, the reaction mixture was cooled down to 0° C. and worked-up following the Fieser process, slowly adding x mL of $H_2O$, x mL of 15% aq. NaOH and 2x mL of $H_2O$, followed by drying with $MgSO_4$, stirring for 1 hour, filtration and evaporation of the volatiles. The crude residue was purified by silica gel flash column chromatography.

Step 3:

A solution of the diol (1.0 eq) in DCM (0.3 M) was slowly added to a suspension of PCC (4.0 eq) in DCM (0.7 M) over 20 minutes. After stirring for 2 hours, Celite® was added followed by $Et_2O$ ($2 \times V_{DCM}$) and hexanes ($1 \times V_{DCM}$). The reaction mixture was stirred for 20 minutes before bring filtered through a plug of Celite® to remove most of the chromium-containing salts. The volatiles were evaporated and the crude residue was purified by silica gel column flash chromatography to provide the desired ketoaldehyde.

Step 4:

A round-bottom flask containing the previously synthesized ketoaldehyde (1.0 eq), aniline (1.0 eq) and acetic acid (1.2 eq) in MeOH (0.25 M) was stirred for 30 minutes at room temperature. $NaBH_3CN$ (2.0 eq) was added and the reaction mixture was heated up to 40° C. for 4 hours. Upon completion of the reaction, as judged by TLC, the reaction mixture was quenched with AcOH and evaporated to dryness. The crude residue was purified by preparative LC-MS to afford the desired piperidine product.

Separation of Enantiomers

Racemic int-C variants were provided to Lotus Separations LLC of Princeton, N.J. for chiral resolution. In general, super critical fluid chromatography was performed using an appropriate column (such as Lux Cellulose-4 (2×25 cm)). An exemplary eluent used is 10% isopropanol/$CO_2$, 100 bar pumping at 70 mL/min and monitored at 220 nm.

Example Compounds

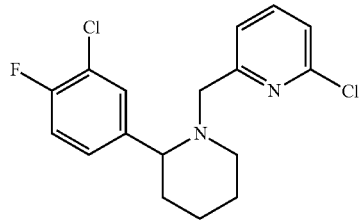 [SMILES: Fc1ccc(C2CCCCN2Cc2cccc(Cl)n2)cc1Cl]

Example Compound 1

Example compound 1 was synthesized according to Method 1 using 2-chloro-1-fluoro-4-iodobenzene as the aryl iodide and 5-chlorovaleroyl chloride in Step 1; and 2-(bromomethyl)-6-chloropyridine as the benzyl bromide in Step 5c. $^1$H NMR (500 MHz, DMSO-d6), δ (ppm): 7.82 (t, 1H, J=7.8 Hz), 7.58 (dd, 1H, J=7.4, 2.1 Hz), 7.41 (m, 2H), 7.34 (m, 2H), 3.55 (d, 1H, J=15.0 Hz), 3.28 (dd, 1H, J=11.0, 2.8 Hz), 3.07 (d, 1H, J=15.0 Hz), 2.85 (dd, 1H, J=11.7, 3.6 Hz), 2.10 (td, 1H, J=11.9, 2.8 Hz), 1.71 (ddt, 2H, J=15.3, 12.8, 3.1 Hz), 1.52 (m, 3H), 1.33 (qt, 1H, J=13.5, 3.9 Hz). $^{13}$C NMR (125 MHz, DMSO-d6), δ (ppm): 160.5, 157.1, 155.1, 149.2, 142.7 (d, J=4 Hz), 140.1, 129.2, 127.7 (d, J=7 Hz), 122.3, 121.2, 119.3 (d, J=18 Hz), 116.9 (d, J=21 Hz), 66.2, 60.0, 53.3, 36.3, 25.4, 24.4.

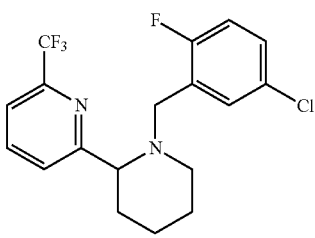 [SMILES: Fc1ccc(Cl)cc1CN1CCCCC1c1cccc(C(F)(F)F)n1]

Example Compound 2

Example compound 2 was synthesized according to Method 3 using 2-bromo-6-(trifluoromethyl)pyridine as the aryl bromide and N-Boc-pipecolic acid as the Boc-protected amino-acid. 2-(Bromomethyl)-4-chloro-1-fluorobenzene was used as the benzyl bromide in Step 5c. $^1$H NMR (500 MHz, DMSO-d6), δ (ppm): 8.06 (t, 1H, J=7.8 Hz), 7.84 (d, 1H, J=7.9 Hz), 7.77 (d, 1H, J=7.5 Hz), 7.40 (dd, 1H, J=6.3, 2.8 Hz), 7.32 (ddd, 1H, J=8.8, 4.4, 2.8 Hz), 7.15 (t, 1H, J=9.2 Hz), 3.44 (dd, 1H, J=11.1, 2.9 Hz), 3.37 (d, 1H, J=14.2 Hz), 3.17 (d, 1H, J=14.1 Hz), 2.88 (dt, 1H, J=11.5, 3.5 Hz), 2.12 (td, 1H, J=11.8, 2.8 Hz), 1.75 (m, 2H), 1.64 (dq, 1H, J=13.0, 2.9 Hz), 1.53 (m, 2H), 1.36 (m, 1H). $^{13}$C NMR (125 MHz, DMSO-d6), δ (ppm): 165.2, 160.7, 158.8, 146.1 (q, J=34 Hz), 139.6, 130.8 (d, J=5 Hz), 129.1 (d, J=9 Hz), 128.5 (d, J=3 Hz), 127.8 (d, J=16 Hz), 125.6, 122.1 (q, J=274 Hz), 119.8 (d, J=3 Hz), 117.5 (d, J=24 Hz), 69.3, 52.9, 52.2, 34.9, 25.6, 24.3.

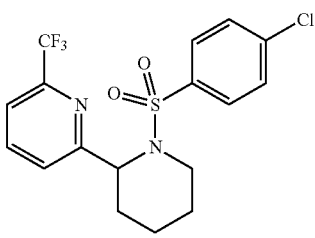 [SMILES: O=S(=O)(c1ccc(Cl)cc1)N1CCCCC1c1cccc(C(F)(F)F)n1]

Example Compound 3

Example compound 3 was synthesized according to Method 3 using 2-bromo-6-(trifluoromethyl)pyridine as the aryl bromide and N-Boc-pipecolic acid as the Boc-protected amino-acid. 4-Chlorophenylsulfonyl chloride was used as the sulfonyl chloride in Step 5a. $^1$H NMR (500 MHz, DMSO-d6), δ (ppm): 8.08 (t, 1H, J=7.8 Hz), 7.74 (dd, 2H, J=7.9, 3.6 Hz), 7.65 (m, 2H), 7.52 (m, 2H), 5.29 (dd, 1H, J=6.1, 2.1 Hz), 3.80 (ddd, 1H, J=13.4, 4.4, 2.5 Hz), 3.39 (td, 1H, J=12.7, 3.3 Hz), 2.14 (ddt, 1H, J=12.6, 4.1, 2.5 Hz), 1.68 (tdd, 1H, J=13.3, 5.8, 3.8 Hz), 1.59 (m, 1H), 1.44 (m, 1H), 1.28 (m, 2H). $^{13}$C NMR (125 MHz, DMSO-d6), δ (ppm): 160.8, 145.8 (q, J=34 Hz), 139.8, 139.0, 138.0, 129.7 (2×C), 128.9 (2×C), 126.1, 122.9 (q, J=273 Hz), 119.5 (d, J=3 Hz), 56.3, 43.1, 28.9, 24.5, 18.3.

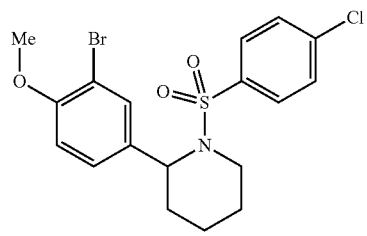 [SMILES: COc1ccc(C2CCCCN2S(=O)(=O)c2ccc(Cl)cc2)cc1Br]

Example Compound 4

Example compound 4 was synthesized according to Method 2 using 1-bromo-2-methoxybenzene as the arene and 5-chlorovaleroyl chloride in Step 1. 4-Chlorophenylsulfonyl chloride was used as the sulfonyl chloride in Step 5a. $^1$H NMR (500 MHz, DMSO-d6), δ (ppm): 7.88 (m, 2H), 7.68 (m, 2H), 7.39 (dd, 1H, J=2.3, 0.9 Hz), 7.29 (ddd, 1H, J=8.6, 2.4, 1.0 Hz), 7.10 (d, 1H, J=8.6 Hz), 5.12 (t, 1H, J=3.6 Hz), 3.84 (s, 3H), 3.75 (m, 1H), 2.92 (ddd, 1H, J=14.2, 12.7, 3.0 Hz), 2.14 (dd, 1H, J=14.4, 3.5 Hz), 1.41 (m, 3H), 1.22 (tdd, 1H, J=14.2, 10.6, 5.7 Hz), 1.08 (tdt, 1H, J=12.3, 8.2, 4.4 Hz). $^{13}$C NMR (125 MHz, DMSO-d6), δ (ppm): 154.7, 140.2, 138.1, 132.9, 131.6, 130.1 (2×C), 129.0 (2×C), 127.8, 113.1, 111.3, 56.7, 54.7, 42.1, 27.5, 24.1, 18.8.

Example compound 5 is the early eluting enantiomer version of Example compound 4 after chiral separations as described above.

Example compound 6 is the later eluting enantiomer version of Example compound 4 after chiral separations as described above.

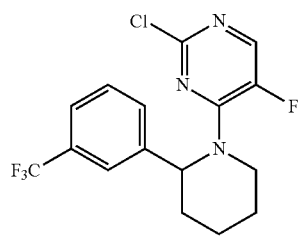 [SMILES: Fc1cnc(Cl)nc1N1CCCCC1c1cccc(C(F)(F)F)c1]

Example Compound 7

Example compound 7 was synthesized according to Method 3 using 3-trifluoromethyl-bromobenzene as the aryl bromide and N-Boc-pipecolic acid as the Boc-protected amino-acid. 2,4-Dichloro-5-fluoropyrimidine was used as the chloro-heteroarene in Step 5b. $^1$H NMR (500 MHz, DMSO-d6), δ (ppm): 8.24 (d, 1H, J=6.5 Hz), 7.66 (m, 1H), 7.63 (m, 3H), 5.78 (t, 1H, J=4.2 Hz), 4.30 (dd, 1H, J=13.7, 3.7 Hz), 3.02 (ddd, 1H, J=14.7, 10.3, 4.7 Hz), 2.45 (dd, 1H, J=14.3, 3.7 Hz), 2.01 (dddd, 1H, J=14.1, 12.5, 5.5, 3.5 Hz), 1.64 (m, 3H), 1.41 (m, 1H). $^{13}$C NMR (125 MHz, DMSO-d6), δ (ppm): 153.4 (d, J=27 Hz), 153.3 (d, J=30 Hz), 146.2 (d, J=256 Hz), 145.0 (d, J=28 Hz), 141.2, 131.2, 130.4, 130.0 (q, J=31 Hz), 124.7 (q, J=272 Hz), 124.2 (q, J=4 Hz), 123.5 (q, J=4 Hz), 55.9 (d, J=6 Hz), 42.7 (d, J=9 Hz), 28.3, 25.1, 19.3.

Example compound 8 is the early eluting enantiomer version of Example compound 7 after chiral separations as described above.

Example compound 9 is the later eluting enantiomer version of Example compound 7 after chiral separations as described above.

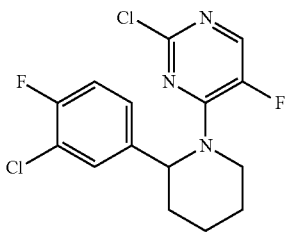 [SMILES: Fc1ccc(C2CCCCN2c2nc(Cl)ncc2F)cc1Cl]

Example Compound 121

Example compound 121 was synthesized according to Method 3 using 2-chloro-1-fluoro-4-iodobenzene as the aryl iodide and N-Boc-pipecolic acid as the Boc-protected amino-acid. 2,4-Dichloro-5-fluoropyrimidine was used as the chloro-heteroarene in Step 5b. $^1$H NMR (500 MHz, DMSO-d6), δ (ppm): 8.22 (d, 1H, J=6.6 Hz), 7.53 (ddd, 1H, J=7.1, 2.4, 1.0 Hz), 7.41 (t, 1H, J=8.9 Hz), 7.32 (dddd, 1H, J=8.4, 4.7, 2.4, 1.0 Hz), 5.70 (s, 1H), 4.27 (m, 1H), 3.02 (ddd, 1H, J=14.4, 11.1, 3.7 Hz), 2.40 (m, 1H), 1.95 (dddd, 1H, J=14.2, 12.5, 5.4, 3.5 Hz), 1.62 (m, 3H), 1.43 (m, 1H). $^{13}$C NMR (125 MHz, DMSO-d6), δ (ppm): 156.6 (d, J=246 Hz), 153.3 (d, J=39 Hz), 153.3 (d, J=40 Hz), 146.2 (d, J=256 Hz), 145.0 (d, J=28 Hz), 137.5 (d, J=4 Hz), 129.2, 127.8 (d, J=7 Hz), 120.4 (d, J=18 Hz), 117.6 (d, J=21 Hz), 55.3 (d, J=5 Hz), 42.6 (d, J=9 Hz), 28.3, 25.2, 19.3.

Example compound 10 is the early eluting enantiomer version of Example compound 121 after chiral separations as described above.

Example compound 11 is the later eluting enantiomer version of Example compound 121 after chiral separations as described above.

Additional exemplary compounds are described in Tables 5-17.

TABLE 5

Example compounds prepared via Methods 1 and 3 with given core structure A "*" indicates a chiral compound. A "*a*" indicates M + Na observed in MS as major product. A "*x*" indicates M-SO2 observed in MS as major product.

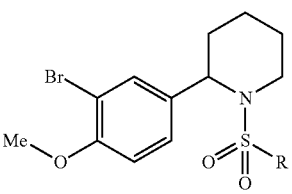

Sulfonyl derivatives of 6

| Compound No. | Expect M + H | Observed M + H | R |
|---|---|---|---|
| 4 | 444.00 | 444.00 | 4-Cl-Ph (racemate) |
| 5 | 444.00 | 444.00 | 4-Cl—Ph* |
| 6 | 444.00 | 444.00 | 4-Cl—Ph* |
| 12 | 424.06 | 424.10 | 4-Me—Ph |
| 13 | 428.03 | 428.00 | 4-F—Ph |
| 14 | 410.04 | 410.00 | Ph |
| 15 | 374.04 | 374.00 | cyclopropyl |
| 16 | 348.03 | 348.00 | Me |

TABLE 5-continued

Example compounds prepared via Methods 1 and 3 with given core structure A "*" indicates a chiral compound. A "*a*" indicates M + Na observed in MS as major product. A "*x*" indicates M-SO2 observed in MS as major product.

| Compound No. | Expect M + H | Observed M + H | R |
|---|---|---|---|
| 17 | 445.00 | 445.00 | 2-Cl-pyrid-3-yl |
| 314 | 461.99 | 461.96 | 2-F-4-Cl—Ph |
| 315 | 461.99 | 461.96 | 3-F-4-Cl—Ph |
| 316 | 444.00 | 444.00 | 3-Cl—Ph |
| 317 | 461.99 | 461.96 | 2-F-3-Cl—Ph |
| 318 | 461.99 | 462.03 | 3-Cl-4-F—Ph |
| 319 | 461.99 | 461.96 | 2-F-5-Cl—Ph |
| 320 | 479.98 | 480.02 | 2,4-DiF-5-Cl—Ph |
| 321 | 458.02 | 458.02 | 4-Cl-Bn |
| 322 | 445.00 | 445.00 | 2-Cl-pyrid-5-yl |
| 323 | 442.05 | 464.08 $^a$ | 2-F—Bn |
| 324 | 442.05 | 464.08 $^a$ | 3-F—Bn |
| 325 | 442.05 | 464.05 $^a$ | 4-F—Bn |
| 397 | 458.02 | 394.14 $^x$ | 2-Cl—Bn |
| 398 | 458.02 | 480.04 $^a$ | 3-Cl—Bn |
| 399 | 410.02 | 410.02 | 3-Cl-propan-1-yl |
| 483 | 414.05 | 414.08 | 1-Me-pyrazol-3-yl |

TABLE 6

Example compounds prepared via Methods 1 and 3 with given core structure. A "*" indicates a chiral compound. A "*a*" indicates M + Na observed in MS as major product. A "*x*" indicates M-SO2 observed in MS as major product.

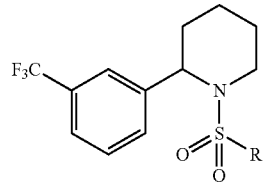

Sulfonyl derivatives of 18

| Compound No. | Expect M + H | Observed M + H | R |
|---|---|---|---|
| 18 | 404.07 | 404.05 | 4-Cl—Ph |
| 19 | 370.11 | 370.10 | Ph |
| 20 | 420.12 | 420.10 | 2-Napthyl |
| 21 | 404.07 | 404.10 | 3-Cl—Ph |
| 22 | 418.09 | 440.20 $^a$ | 4-Cl—Bn |
| 23 | 452.05 | 388.10 $^x$ | 3,4-DiCl—Bn |
| 24 | 418.09 | 354.20 $^x$ | 2-Cl—Bn |
| 25 | 422.06 | 422.10 | 4-Cl-2-F—Ph |
| 26 | 406.09 | 406.10 | 2,5-DiF—Ph |
| 27 | 384.12 | 384.10 | 3-Me—Ph |
| 28 | 422.06 | 422.10 | 3-Cl-2-F—Ph |
| 426 | 384.12 | 406.14 $^a$ | Bn |

TABLE 7

Example compounds prepared via Method 4 with the given core structure. A "*" indicates a chiral compound. A "*a*" indicates M + Na observed in MS as major product. A "*x*" indicates M-SO2 observed in MS as major product.

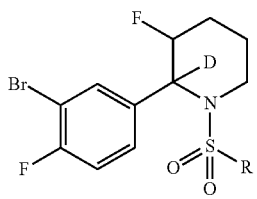

Sulfonyl derivatives of 29

| Compound No. | Expect M + H | Observed M + H | R |
|---|---|---|---|
| 29 | 450.97 | 451.00 | 4-Cl—Ph |
| 30 | 417.01 | 417.00 | Ph |
| 31 | 467.03 | 467.00 | 2-Napthyl |
| 32 | 450.97 | 451.00 | 3-Cl—Ph |
| 33 | 464.99 | 401.10 $^x$ | 4-Cl—Bn |
| 34 | 498.95 | 521.00 $^a$ | 3,4-DiCl—Bn |
| 35 | 431.03 | 367.10 $^x$ | Bn |
| 36 | 464.99 | 401.10 $^x$ | 2-Cl—Bn |
| 37 | 468.96 | 469.00 | 4-Cl-2-F—Ph |
| 38 | 452.99 | 453.00 | 2-5-DiF—Ph |
| 39 | 447.02 | 447.00 | 4-OMe—Ph |

TABLE 8

Example compounds prepared via Methods 1, 2 and 3 with given core structure. A "*" indicates a chiral compound. A "*a*" indicates M + Na observed in MS as major product. A "*x*" indicates M-SO2 observed in MS as major product.

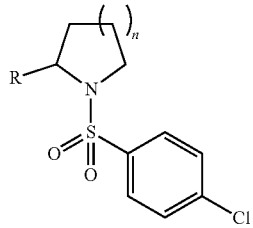

Sulfonamide aryls

| No. | n | Expect M + H | Observed M + H | R |
|---|---|---|---|---|
| 3 | 2 | 405.07 | 405.10 | 6-CF3-pyrid-2-yl |
| 4 | 2 | 444.00 | 444.00 | 3-Br-4-OMe—Ph (racemate) |
| 5 | 2 | 444.00 | 444.00 | 3-Br-4-OMe—Ph* |
| 6 | 2 | 444.00 | 444.00 | 3-Br-4-OMe—Ph* |
| 18 | 2 | 404.07 | 404.05 | 3-CF3—Ph |
| 40 | 0 | 415.97 | 416.00 | 3-Br-4-OMe—Ph |
| 41 | 1 | 429.99 | 430.00 | 3-Br-4-OMe—Ph |
| 42 | 2 | 444.00 | 466.10 $^a$ | 4-Br-3-OMe—Ph |
| 43 | 2 | 497.98 | 498.00 | 3-Br-4-OCF3—Ph |
| 44 | 2 | 380.07 | 402.10 $^a$ | benzo[d][1,3]diox-5-ole |
| 45 | 2 | 337.08 | 337.10 | pyrid-2-yl |
| 46 | 2 | 351.09 | 351.10 | 6-Me-pyrid-2-yl |
| 47 | 2 | 362.07 | 362.10 | 6-CN-pyrid-2-yl |
| 48 | 2 | 421.06 | 421.10 | 6-OCF3-pyrid-2-yl |
| 49 | 2 | 429.07 | 429.00 | 3-CF3-4-CN—Ph |
| 50 | 2 | 423.07 | 423.10 | 3-CF3-5-F—Ph |
| 51 | 2 | 400.05 | 400.05 | 3-Cl-4-OMe—Ph |
| 52 | 2 | 388.03 | 388.00 | 3-Cl-4-F—Ph |

TABLE 8-continued

Example compounds prepared via Methods 1, 2 and 3 with given core structure. A "*" indicates a chiral compound. A "*a*" indicates M + Na observed in MS as major product. A "*x*" indicates M-SO2 observed in MS as major product.

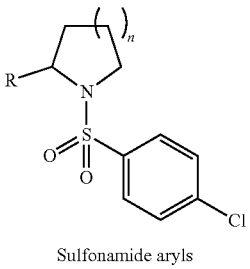

Sulfonamide aryls

| No. | n | Expect M + H | Observed M + H | R |
|---|---|---|---|---|
| 53 | 2 | 355.07 | 355.10 | 2-F-pyrid-5-yl |
| 54 | 2 | 355.07 | 355.10 | 5-F-pyrid-2-yl |
| 55 | 2 | 422.06 | 422.05 | 3-CF3-4-F—Ph |
| 56 | 2 | 431.98 | 431.95 | 3-Br-4-F—Ph* |
| 57 | 2 | 405.07 | 405.10 | 2-CF3-pyrid-4-yl |
| 58 | 2 | 379.07 | 379.10 | 3-CN-4-F—Ph |
| 59 | 2 | 355.07 | 355.10 | 2-F-pyrid-4-yl |
| 60 | 2 | 431.98 | 432.00 | 3-Br-4-F—Ph |
| 61 | 2 | 370.04 | 370.00 | 3-Cl—Ph |
| 62 | 2 | 355.07 | 355.10 | 4-F-pyrid-2-yl |
| 63 | 2 | 406.06 | 406.10 | 6-CF3-pyrazin-2-yl |
| 64 | 2 | 438.03 | 438.00 | 3-CF3-4-Cl—Ph |
| 65 | 2 | 405.07 | 405.10 | 5-CF3-pyrid-2-yl |
| 66 | 2 | 378.09 | 378.05 | 2,3-dihydrobenzo-furan-5-yl |
| 67 | 2 | 368.09 | 368.10 | 3-Me-4-F—Me—Ph |
| 68 | 2 | 380.11 | 380.10 | 3-Me-4-OMe—Ph |
| 69 | 2 | 438.03 | 438.00 | 3-CF3-4-Cl—Ph* |
| 70 | 2 | 428.01 | 428.00 | 3-Br-4-Me—Ph |
| 71 | 2 | 431.98 | 431.95 | 3-F-4-Br—Ph |
| 72 | 2 | 422.06 | 422.10 | 3-CF3-5-F—Ph |
| 73 | 2 | 406.06 | 406.10 | 4-CF3-2-pyrimid-2-yl |
| 74 | 2 | 447.95 | 470.00 | 3-Br-4-Cl—Ph |
| 75 | 2 | 372.06 | 372.10 | 3,4-DiF—Ph |
| 76 | 2 | 370.04 | 370.00 | 4-Cl—Ph |
| 77 | 2 | 351.09 | 351.10 | 2-Me-pyrid-4-yl |
| 78 | 2 | 354.07 | 354.10 | 4-F—Ph |
| 79 | 2 | 405.07 | 405.10 | 4-CF3-pyrid-2-yl |
| 80 | 2 | 362.07 | 362.10 | 2-CN-pyrid-4-yl |
| 81 | 2 | 395.08 | 395.10 | (2-(methyl Carboxylate)-pyrid-4-yl |
| 82 | 2 | 355.07 | 355.10 | 5-F-pyrid-3-yl |
| 83 | 2 | 405.07 | 405.10 | 5-CF3-pyrid-3-yl |
| 84 | 3 | 458.02 | 458.00 | 3-Br-4-OMe—Ph |
| 220 | 2 | 438.03 | 438.00 | 3-CF3-4-Cl—Ph* |
| 427 | 2 | 390.05 | 390.09 | 3,4,5-TriF—Ph |
| 446 | 2 | 431.98 | 431.98 | 3-Br-4-F—Ph* |

TABLE 9

Example compounds prepared via Methods 3, 5 and 6 with given core structure. A "*" indicates a chiral compound. A "ᵃ" indicates M + Na observed in MS as major product. A "ˣ" indicates M-SO2 observed in MS as major product.

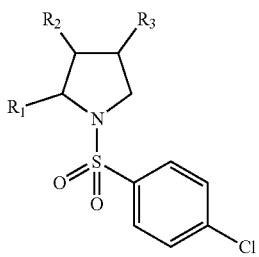

substituted sulfonyl pyrrolidines

| Compound Number | Expected M + H | Observed M + H | R1 | R2 | R3 |
| --- | --- | --- | --- | --- | --- |
| 85 | 465.97 | 465.95 | 3-Br-4-OMe—Ph | F,F | H,H |
| 86 | 497.98 | 497.95 | 3-Br-4-OMe—Ph | H,H | H,CF₃ |
| 87 | 438.03 | 438.00 | 3-CF₃-4-Cl—Ph | H,Me | H,H |
| 88 | 370.04 | 370.00 | 4-Cl—Ph | H,Me | H,H |
| 89 | 404.07 | 404.10 | 3-CF₃—Ph | H,Me | H,H |
| 90 | 497.98 | 497.95 | 3-Br-4-OMe—Ph | H,CF₃ | H,H |
| 91 | 378.09 | 378.10 | 2,3-dihydro-benzofuran-5-yl | H,Me | H,H |
| 92 | 431.98 | 432.00 | 3-F-4-Br—Ph | H,Me | H,H |
| 93 | 379.07 | 379.10 | 3-CN-4-F—Ph | H,Me | H,H |
| 94 | 497.98 | 498.00 | 3-Br-4-OCF₃—Ph | H,Me | H,H |
| 95 | 354.07 | 354.10 | 4-F-Ph | H,Me | H,H |
| 96 | 380.07 | 380.10 | benzo[d][1,3]diox-5-ole | H,Me | H,H |
| 97 | 372.06 | 372.10 | 3,4-DiF—Ph | H,Me | H,H |
| 98 | 390.05 | 390.10 | 2,3,4-DiF—Ph | H,Me | H,H |
| 99 | 447.95 | 448.00 | 3-Br-4-Cl—Ph | H,Me | H,H |
| 100 | 422.05 | 422.10 | 3-CF3-4-F—Ph | H,Me | H,H |
| 101 | 368.08 | 368.10 | 3-Me-4-F—Ph | H,Me | H,H |
| 102 | 444.00 | 444.00 | 3-Br-4-OMe—Ph | H,Me | H,H |
| 103 | 515.96 | 516.00 | 3-Br-4-OMe—Ph | F,CF₃ | H,H |
| 104 | 428.00 | 428.00 | 3-Br-4-Me—Ph | H,Me | H,H |
| 105 | 388.03 | 388.00 | 3-Cl-4-F—Ph | H,Me | H,H |
| 106 | 431.98 | 432.00 | 3-Br-4-F—Ph | H,Me | H,H |
| 107 | 370.04 | 370.00 | 3-Cl—Ph | H,Me | H,H |
| 108 | 497.98 | 497.95 | 3-Br-4-OMe—Ph* | H,CF₃ | H,H |
| 109 | 497.98 | 497.95 | 3-Br4-OMe—Ph* | H,H | H,CF₃ |
| 110 | 465.97 | 465.95 | 3-Br-4-OMe—Ph* | F,F | H,H |
| 111 | 497.97 | 497.95 | 3-Br4-OMe—Ph* | H,H | H,CF₃ |
| 112 | 447.97 | 447.95 | 3-Br4-OMe—Ph* | H,H | H,F |
| 113 | 465.96 | 487.95 | 3-Br-4-OMe—Ph | F,F | H,H |
| 41 | 429.98 | 430.00 | 3-Br-4-OMe—Ph | H,H | H,H |
| 114 | 447.97 | 470.00 | 3-Br4-OMe—Ph* | H,H | H,F |
| 115 | 447.97 | 447.95 | 3-Br4-OMe—Ph | H,F | H,H |
| 116 | 465.96 | 488.00 ᵃ | 3-Br-4-OMe—Ph* | F,F | H,H |
| 117 | 497.97 | 497.95 | 3-Br-4-OMe—Ph* | H,CF₃ | H,H |
| 118 | 444.00 | 444.00 | 3-Br-4-OMe—Ph* | H,H | H,Me |
| 119 | 497.98 | 497.95 | 3-Br-4-OMe—Ph* | H,H | H,CF₃ |
| 120 | 497.98 | 497.95 | 3-Br-4-OMe—Ph* | H,H | H,CF₃ |

TABLE 10

Example compounds prepared via Methods 1, 2 and 3 with given core structure. A "*" indicates a chiral compound.

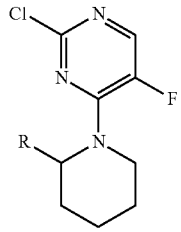

Aryl Derivatives of 7

| Compound No | Expected M + H | Observed M + H | R |
|---|---|---|---|
| 7 | 360.09 | 360.10 | 3-CF3—Ph |
| 8 | 360.09 | 360.10 | 3-CF3—Ph* |
| 9 | 360.09 | 360.05 | 3-CF3—Ph* |
| 10 | 344.05 | 344.10 | 3-Cl-4-F—Ph* |
| 11 | 344.05 | 344.05 | 3-Cl-4-F—Ph* |
| 121 | 344.05 | 344.05 | 3-Cl-4-F—Ph |
| 122 | 378.08 | 378.05 | 3-CF3-5-F—Ph |
| 123 | 361.08 | 361.05 | 6-CF3-pyrid-2-yl |
| 124 | 388.00 | 387.95 | 3-Br-4-F—Ph |
| 125 | 403.97 | 403.95 | 3-Br-4-Cl—Ph* |
| 126 | 453.99 | 453.95 | 3-Br-4-OCF3—Ph |
| 127 | 310.09 | 310.05 | 4-F—Ph |
| 128 | 394.05 | 394.00 | 3-CF3-4-Cl—Ph |
| 129 | 328.08 | 328.05 | 3,4-DiF—Ph |
| 130 | 324.11 | 324.10 | 3-Me-4-F—Ph |
| 131 | 377.08 | 377.05 | 6-OCF3-pyrid-2-yl |
| 132 | 400.02 | 400.00 | 3-Br-4-OMe—Ph |
| 133 | 311.09 | 311.05 | 6-F-pyrid-2-yl |
| 134 | 374.10 | 374.10 | 2-Me-5-CF3—Ph |
| 135 | 374.10 | 374.10 | 2-Me-3-CF3—Ph |
| 274 | 362.08 | 362.12 | 6-CF3-pyrazin-2-yl |
| 275 | 323.11 | 323.11 | 2-OMe-pyrid-4-yl |
| 276 | 327.06 | 327.09 | 6-Cl-pyrid-2-yl |
| 277 | 328.05 | 328.05 | 6-Cl-pyrazin-2-yl |
| 278 | 361.08 | 361.08 | 4-CF3-pyrid-2-yl |
| 279 | 349.09 | 349.05 | 2(3H)-benzoxazolon-6-yl |
| 280 | 327.06 | 327.06 | 5-Cl-pyrid-3-yl |
| 281 | 384.03 | 384.06 | 3-Br-4-Me—Ph |
| 283 | 343.11 | 343.08 | 4-quinoline |
| 284 | 332.11 | 332.07 | imidazo[1,2-a]pyrid-5-yl |
| 285 | 326.06 | 326.03 | 3-Cl—Ph |
| 286 | 343.11 | 343.15 | isoquinolin-8-yl |
| 287 | 438.00 | 437.96 | 3-CF3-4-Br—Ph |
| 288 | 400.02 | 400.06 | 3-OMe-4-Br—Ph |
| 289 | 390.10 | 390.10 | 3-CF3-4-OMe—Ph |
| 290 | 388.00 | 387.97 | 3-F-4-Br—Ph |
| 291 | 333.10 | 333.10 | [1,4,5]triazolo[1,2-a]pyridin-6-yl |
| 292 | 332.11 | 332.11 | imidazo[1,2-a]pyrid-4-yl |
| 294 | 352.12 | 352.09 | 3,4-DiOMe—Ph |
| 297 | 311.09 | 311.05 | 2-F-pyrid-5-yl |
| 298 | 342.10 | 342.06 | 3-DiFluoroMethyl—Ph |
| 299 | 360.09 | 360.05 | 3-DiFluoroMethyl-4-F—Ph |
| 300 | 414.11 | 414.07 | 5-CF3-1-Me-Benzimidazol-7-yl |
| 326 | 343.11 | 343.15 | 6-quinoline |
| 327 | 346.07 | 346.07 | 3,4,5-TriF—Ph |
| 328 | 327.06 | 327.07 | 2-Cl-pyrid-4-yl |
| 329 | 293.10 | 293.06 | pyrid-2-yl |
| 330 | 307.11 | 307.11 | 5-Me-pyrid-3-yl |
| 331 | 360.02 | 359.99 | 3,4,-DiCl—Ph |
| 332 | 361.08 | 361.08 | 4-CF3-pyrid-3-yl |
| 333 | 333.10 | 333.07 | [1,4,5]triazolo[1,2-a]pyridin-7-yl |
| 334 | 332.11 | 332.11 | imidazo[1,5-a]pyrid-6-yl |
| 335 | 311.09 | 311.12 | 2-F-pyrid-3-yl |
| 336 | 332.11 | 332.11 | imidazo[1,2-a]pyrid-3-yl |
| 337 | 333.10 | 333.14 | imidazo[1,2-a]pyridizin-3-yl |
| 338 | 333.10 | 333.07 | imidazo[1,2-a]pyrizin-3-yl |
| 339 | 333.10 | 333.14 | imidazo[1,2-a]pyridizin-5-yl |
| 340 | 349.07 | 349.10 | benzthiazol-2-yl |
| 341 | 349.07 | 349.07 | benzthiazol-6-yl |
| 343 | 344.05 | 344.02 | 3-Cl-4-F—Ph* |

TABLE 10-continued

Example compounds prepared via Methods 1, 2 and 3 with given core structure. A "*" indicates a chiral compound.

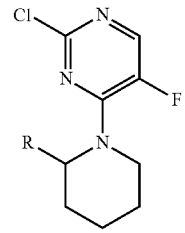

Aryl Derivatives of 7

| Compound No | Expected M + H | Observed M + H | R |
|---|---|---|---|
| 345 | 394.05 | 394.09 | 3-CF3-4-Cl—Ph* |
| 346 | 344.05 | 344.02 | 3-Cl-4-F—Ph* |
| 348 | 394.05 | 394.09 | 3-CF3-4-Cl—Ph* |
| 352 | 400.10 | 400.13 | 7-CF3-1H-Indazol-5-yl |
| 353 | 378.08 | 378.08 | 2-F-5-CF3—Ph |
| 354 | 455.99 | 455.95 | 2-Br-3-F-6-CF3—Ph |
| 355 | 378.08 | 378.08 | 2-F-3-CF3—Ph |
| 357 | 346.04 | 346.08 | 2-Cl-5-F-pyrimid-4-yl |
| 358 | 298.09 | 298.05 | 3-Me-1,2,4-oxadiazol-5-yl |
| 362 | 292.10 | 292.07 | Ph |
| 363 | 298.09 | 298.12 | 5-Me-1,3,4-oxadiazol-2-yl |
| 364 | 297.09 | 297.13 | 5-Me-oxazol-2-yl |
| 366 | 297.09 | 297.05 | 4-Me-oxazol-2-yl |
| 369 | 344.05 | 344.05 | 2-F-3-Cl—Ph |
| 370 | 311.09 | 311.05 | 5-F-pyrid-3-yl |
| 371 | 334.11 | 334.11 | 2,3-dihydrobenzofuran-5-yl |
| 372 | 311.09 | 311.05 | 5-F-pyrid-2-yl |
| 373 | 293.10 | 293.06 | pyrid-3-yl |
| 374 | 333.10 | 333.10 | [1,4,5]triazolo[1,2-a]pyridin-5-yl |
| 375 | 311.09 | 311.09 | 3-F-pyrid-4-yl |
| 376 | 361.08 | 361.08 | 5-CF3-pyrid-3-yl |
| 377 | 308.11 | 308.14 | 2-Me-pyrimid-4-yl |
| 378 | 294.09 | 294.13 | pyrimid-5-yl |
| 379 | 358.06 | 358.10 | 4-Cl-5-OMe-pyrimid-2-yl |
| 380 | 323.11 | 323.11 | 2-OMe-pyrid-3-yl |
| 388 | 345.05 | 345.08 | 3-F-6-Cl-pyrid-2-yl |
| 389 | 333.10 | 333.07 | [1,3,4]triazolo[4,5-a]pyridin-5-yl |
| 390 | 345.05 | 345.08 | 2-F-5-Cl-pyrid-3-yl |
| 391 | 294.09 | 294.13 | pyrimid-4-yl |
| 392 | 342.07 | 342.10 | 2-Me-5-Cl-pyrimid-4-yl |
| 393 | 359.11 | 359.14 | 3-Hydroxy-quinolin-6-yl |
| 400 | 344.05 | 344.09 | 2-F-5-Cl—Ph |
| 404 | 344.05 | 344.02 | 3-Cl-5-F—Ph* |
| 407 | 307.11 | 307.08 | 2-Me-Pyrid-3-yl |
| 408 | 327.06 | 327.02 | 4-Cl-pyrid-2-yl |
| 409 | 298.09 | 298.12 | 5-Me-1,2,4-oxadiazol-3-yl |
| 410 | 361.08 | 361.05 | 2-CF3-pyrid-4-yl |
| 411 | 307.11 | 307.08 | 2-Me-pyrid-5-yl |
| 412 | 311.09 | 311.09 | 4-F-pyrid-2-yl |
| 413 | 361.08 | 361.05 | 2-CF3-pyrid-5-yl |
| 414 | 307.11 | 307.15 | 6-Me-pyrid-2-yl |
| 417 | 400.10 | 400.10 | 7-CF3-1H-benzimidazol-5-yl |
| 420 | 344.05 | 344.02 | 3-Cl-5-F—Ph* |
| 421 | 332.11 | 332.07 | imidazo[1,2-a]pyrid-6-yl |
| 422 | 378.08 | 378.08 | 3-CF3-4-F—Ph* |
| 423 | 378.08 | 378.08 | 3-CF3-5-F—Ph* |
| 429 | 260.06 | 260.02 | Carboxy |

TABLE 11

Example compounds prepared via Method 3 with given core structure. A "*" indicates a chiral compound.

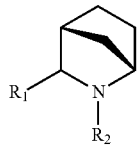

bicyclic derivatives

| No. | Expect M + H | Obs. M + H | R1 | R2 |
|---|---|---|---|---|
| 136 | 400.00 | 399.95 | 3-Br-4-F—Ph | 2-Cl-5-F-pyrimidin-4-yl |
| 137 | 373.08 | 373.05 | 6-CF$_3$-pyrid-2-yl | 2-Cl-5-F-pyrimidin-4-yl |
| 138 | 412.02 | 412.05 | 3-Br-4-OMe—Ph | 2-Cl-5-F-pyrimidin-4-yl |
| 139 | 390.08 | 390.05 | 3-CF$_3$-5-F—Ph | 2-Cl-5-F-pyrimidin-4-yl |
| 216 | 402.10 | 402.10 | 3-CF$_3$-5-F—Ph | 3-Cl-6-F—Bn |
| 217 | 368.08 | 368.05 | 3-Cl-4-F—Ph | 3-Cl-6-F—Bn |
| 430 | 372.09 | 372.05 | 3-CF$_3$—Ph | 2-Cl-5-F-pyrimidin-4-yl |
| 431 | 356.05 | 356.02 | 3-Cl-4-F—Ph | 2-Cl-5-F-pyrimidin-4-yl |
| 444 | 385.11 | 385.15 | 6-CF3-pyrid-2-yl | 3-Cl-6-F—Bn |

TABLE 12

Example compounds prepared via Methods 1, 2 and 3 with given core structure. A "*" indicates a chiral compound.

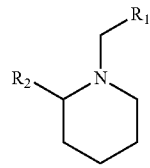

Aryl Derivatives of 1

| No. | Exp M + H | Obs M + H | R1 | R2 |
|---|---|---|---|---|
| 1 | 339.08 | 339.10 | 6-Cl-pyrid-2-yl | 3-Cl-4-F—Ph |
| 2 | 373.11 | 373.10 | 2-F-5-Cl—Ph | 6-CF3-pyrid-2-yl |
| 140 | 354.12 | 354.10 | 4-Cl—Ph | 3-CF3—Ph |
| 141 | 364.16 | 364.15 | 2-F-5-Cl—Ph | 6-(2-amino)ethan-1-ol)pyridin-2-yl) |
| 142 | 348.16 | 348.15 | 2-F-5-Cl—Ph | 6-(2-amino)ethane)pyridin-2-yl) |
| 143 | 356.11 | 356.10 | 5-Cl-pyrid-3-yl | 6-CF3-pyrid-2-yl |
| 144 | 346.12 | 346.10 | 2-F-5-Cl—Ph | 6-azido-pyrid-2-yl |
| 145 | 339.08 | 339.05 | 4-Cl-pyrid-2-yl | 3-Cl-4-F—Ph |
| 146 | 355.12 | 355.10 | 4-Cl—Ph | 6-CF3-pyrid-2-yl |
| 147 | 339.08 | 339.05 | 5-Cl-pyrid-3-yl | 3-Cl-4-F—Ph |
| 148 | 416.06 | 416.05 | 3-Br—Ph | 3-CF3-5-F—Ph |
| 149 | 348.16 | 348.15 | 2-F-5-Cl—Ph | 6-N(Me)2-pyrid-2-yl |
| 150 | 406.08 | 406.05 | 2-F-5-Cl—Ph | 3-CF3-4-Cl—Ph |
| 151 | 372.05 | 372.00 | 3,5-diCl—Ph | 3-Cl-4-F—Ph |
| 152 | 339.15 | 339.10 | 3-F—Ph | 6-CF3-pyrid-2-yl |
| 153 | 389.08 | 389.05 | 3,4-diCl—Ph | 6-CF3-pyrid-2-yl |
| 154 | 354.12 | 354.10 | 3-Cl—Ph | 3-CF3—Ph |
| 155 | 356.08 | 356.05 | 3-Cl-5-F—Ph | 3-Cl-4-F—Ph |
| 156 | 351.17 | 351.15 | 3-OMe—Ph | 6-CF3-pyrid-2-yl |
| 157 | 372.11 | 372.10 | 3-Cl—Ph | 3-CF3-5-F—Ph |
| 158 | 372.05 | 372.00 | 2,5-diCl—Ph | 3-Cl-4-F—Ph |
| 159 | 389.08 | 389.05 | 3,5-diCl—Ph | 6-CF3-pyrid-2-yl |
| 160 | 356.08 | 356.05 | 2-F-5-Cl—Ph | 3-Cl-4-F—Ph |
| 161 | 373.11 | 373.10 | 3-Cl-4-F—Ph | 6-CF3-pyrid-2-yl |
| 162 | 356.11 | 356.10 | 4-Cl-pyrid-2-yl | 6-CF3-pyrid-2-yl |
| 163 | 322.12 | 322.10 | 2-F-5-Cl—Ph | 4-F—Ph |
| 164 | 373.11 | 373.10 | 3-Cl-5-F—Ph | 6-CF3-pyrid-2-yl |
| 165 | 356.11 | 356.10 | 6-Cl-pyrid-2-yl | 6-CF3-pyrid-2-yl |
| 166 | 356.11 | 356.10 | 2-Cl-pyrid-4-yl | 6-CF3-pyrid-2-yl |

TABLE 12-continued

Example compounds prepared via Methods 1, 2 and 3 with given core structure. A "*" indicates a chiral compound.

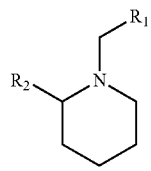

Aryl Derivatives of 1

| No. | Exp M + H | Obs M + H | R1 | R2 |
|---|---|---|---|---|
| 167 | 390.10 | 390.10 | 2-F-5-Cl—Ph | 3-CF3-5-F—Ph |
| 168 | 334.15 | 334.10 | 2-F-5-Cl—Ph | 6-NHMe-pyrid-2-yl |
| 169 | 389.10 | 389.10 | 2-F-5-Cl—Ph | 6-OCF3-pyrid-2-yl |
| 170 | 355.12 | 355.10 | 3-Cl—Ph | 6-CF3-pyrid-2-yl |
| 171 | 323.11 | 323.10 | 2-F-5-Cl—Ph | 6-F-pyrid-2-yl |
| 172 | 373.11 | 373.10 | 2-F-3-Cl—Ph | 6-CF3-pyrid-2-yl |
| 173 | 399.07 | 399.05 | 3-Br—Ph | 6-CF3-pyrid-2-yl |
| 174 | 339.08 | 339.05 | 2-Cl-pyrid-4-yl | 3-Cl-4-F—Ph |
| 175 | 389.15 | 389.10 | 3-CF3—Ph | 6-CF3-pyrid-2-yl |
| 176 | 389.08 | 389.05 | 2,5-diCl—Ph | 6-CF3-pyrid-2-yl |
| 245 | 412.05 | 412.05 | 2-F-3-Cl—Bn | 3-Br-4-OMe—Ph |
| 432 | 412.05 | 412.05 | 2-F-5-Cl—Bn | 3-Br-4-OMe—Ph |
| 433 | 400.03 | 400.06 | 2-F-5-Cl—Bn | 3-Br-4-F—Ph |
| 434 | 340.11 | 340.07 | 2-F-5-Cl—Bn | 3,4-DiF—Ph |
| 435 | 336.13 | 336.10 | 2-F-5-Cl—Bn | 3-Me-4-F—Ph |
| 436 | 466.02 | 465.98 | 2-F-5-Cl—Bn | 3-Br-4-OCF3—Ph |
| 437 | 416.00 | 416.03 | 2-F-5-Cl—Bn | 3-Br-4-Cl—Ph |
| 438 | 364.16 | 364.12 | 2-F-5-Cl—Bn | 6-(N,O-dimethylhydroxylamine)-pyridin-2-yl) |
| 439 | 402.14 | 402.17 | 2-F-5-Cl—Bn | 6-(N-(2,2,2-trifluoroethyl))-pyridin-2-yl) |

TABLE 13

Example compounds prepared via Method 3 with given core structure. Stereochemistry at bicycle is (2S,6R). If designated as *, then stereochemistry at bicycle is (2R,6S).

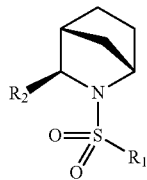

Sulfonyl bicyclic derivatives

| No. | Expect M + H | Observed M + H | R1 | R2 |
|---|---|---|---|---|
| 177 | 456.01 | 456.00 | 4-Cl—Ph | 3-Br-4-OMe—Ph |
| 178 | 443.99 | 443.95 | 4-Cl—Ph | 3-Br-4-F—Ph |
| 179 | 443.99 | 443.95 | 4-Cl—Ph | 3-Br-4-F—Ph* |
| 180 | 443.99 | 443.95 | 3-Cl—Ph | 3-Br-4-F—Ph |
| 181 | 491.96 | 514.10 | 3,4-DiCl—Bn | 3-Br-4-F—Ph |
| 182 | 424.04 | 360.10 | Bn | 3-Br-4-F—Ph |
| 183 | 458.00 | 394.10 | 2-Cl—Bn | 3-Br-4-F—Ph |
| 184 | 461.98 | 461.95 | 2-F-4-Cl—Ph | 3-Br-4-F—Ph |

TABLE 14

Example compounds prepared via Method 3 with given core structure. A "*" indicates a chiral compound.

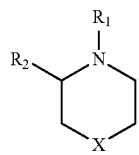

Di-Hetero derivatives

| No. | Expect M + H | Obs M + H | R1 | R2 | X |
|-----|--------------|-----------|----|----|---|
| 185 | 433.97 | 433.95 | 4-Cl—PhSO2 | 3-Br-4-F—Ph | O |
| 186 | 363.07 | 363.05 | 2-Cl-5-F-pyrimidin-4-yl | 6-CF3-pyrid-2-yl | O |
| 187 | 402.00 | 401.95 | 2-Cl-5-F-pyrimidin-4-yl | 3-Br-4-OMe—Ph | O |
| 188 | 362.07 | 362.05 | 2-Cl-5-F-pyrimidin-4-yl | 3-CF3—Ph | O |
| 189 | 346.03 | 346.00 | 2-Cl-5-F-pyrimidin-4-yl | 3-Cl-4-F—Ph | O |
| 190 | 380.06 | 380.05 | 2-Cl-5-F-pyrimidin-4-yl | 3-CF3-5-F—Ph | O |
| 191 | 375.09 | 375.05 | 2-F-5-Cl—Bn | 6-CF3-pyrid-2-yl | O |
| 192 | 414.03 | 414.00 | 2-F-5-Cl—Bn | 3-Br-4-OMe—Ph | O |
| 193 | 374.10 | 374.05 | 2-F-5-Cl—Bn | 3-CF3—Ph | O |
| 194 | 358.06 | 358.05 | 2-F-5-Cl—Bn | 3-Cl-4-F—Ph | O |
| 195 | 392.09 | 392.05 | 2-F-5-Cl—Bn | 3-CF3-5-F—Ph | O |
| 222 | 445.98 | 445.95 | 4-Cl—PhSO2 | 3-Br-4-OMe—Ph | O |
| 282 | 375.10 | 375.06 | 2-Cl-5-F-Pyrimid-4-yl | 3-CF3—Ph | NMe |
| 301 | 396.04 | 396.00 | 2-Cl-5-F-pyrimid-4-yl | 3-CF3-5-F—Ph | S |
| 302 | 412.03 | 412.07 | 2-Cl-5-F-pyrimid-4-yl | 3-CF3-5-F—Ph | SO |
| 303 | 428.03 | 427.99 | 2-Cl-5-F-pyrimid-4-yl | 3-CF3-5-F—Ph | SO2 |
| 305 | 393.09 | 393.05 | 2-Cl-5-F-pyrimid-4-yl | 3-CF3-5-F—Ph | NMe |
| 306 | 464.13 | 464.13 | 2-Cl-5-F-pyrimid-4-yl | 3-CF3-5-F—Ph | NCO(CH2N(Me)2) |
| 307 | 465.11 | 465.08 | 2-Cl-5-F-pyrimid-4-yl | 3-CF3-5-F—Ph | NCO(CMe2OH) |
| 308 | 421.09 | 421.05 | 2-Cl-5-F-pyrimid-4-yl | 3-CF3-5-F—Ph | NAc |
| 309 | 457.05 | 457.02 | 2-Cl-5-F-pyrimid-4-yl | 3-CF3-5-F—Ph | NSO2Me |
| 344 | 380.06 | 380.09 | 2-Cl-5-F-pyrimidin-4-yl | 3-CF3-5-F—Ph* | O |
| 347 | 380.06 | 380.06 | 2-Cl-5-F-pyrimidin-4-yl | 3-CF3-5-F—Ph* | O |
| 419 | 375.12 | 375.12 | 2-OMe-5-F-pyrimidin-4-yl | 3-CF3-5-F—Ph | NH |
| 456 | 378.05 | 378.05 | 2-Cl-5-F-pyrimid-4-yl | 3-CF3—Ph | S |
| 460 | 362.01 | 362.01 | 2-Cl-5-F-pyrimid-4-yl | 3-Cl-4-F—Ph | S |

TABLE 15

Example compounds prepared via Method 3 with given core structure.

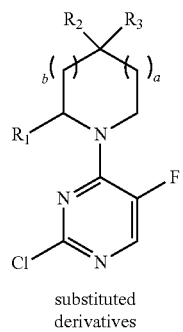

substituted derivatives

| Number | Exp M + H | Obs M + H | a | b | R1 | R2 | R3 |
|--------|-----------|-----------|---|---|----|----|----|
| 196 | 396.07 | 396.05 | 1 | 1 | 3-CF3-5-F—Ph | F | H |
| 197 | 378.08 | 378.05 | 1 | 1 | 3-CF3—Ph | F | H |
| 198 | 414.06 | 414.05 | 1 | 1 | 3-CF3-5-F—Ph | F | F |
| 199 | 396.07 | 396.05 | 1 | 1 | 3-CF3—Ph | F | F |
| 200 | 390.08 | 390.05 | 1 | 1 | 3-CF3-5-F—Ph | CH2 | null |
| 201 | 394.08 | 394.05 | 1 | 1 | 3-CF3-5-F—Ph | OH | H |
| 202 | 376.09 | 376.05 | 1 | 1 | 3-CF3—Ph | OH | H |
| 223 | 366.02 | 366.00 | 0 | 1 | 3-CF3-5-F—Ph | F | F |
| 224 | 400.05 | 400.00 | 0 | 1 | 3-Cl-4-F—Ph | F | F |
| 221 | 361.08 | 361.08 | 0 | 1 | 6-CF3-pyrid-2-yl* | Me | H |
| 237 | 400.02 | 400.06 | 0 | 1 | 3-Br-4-Ome—Ph | Me | H |

TABLE 15-continued

Example compounds prepared via Method 3 with given core structure.

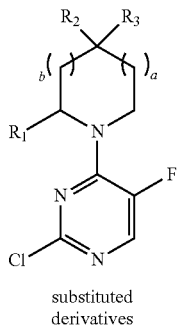

substituted derivatives

| Number | Exp M + H | Obs M + H | a | b | R1 | R2 | R3 |
|---|---|---|---|---|---|---|---|
| 238 | 392.06 | 392.06 | 1 | 1 | 3-CF3-5-F—Ph | O | null |
| 239 | 374.07 | 374.07 | 1 | 1 | 3-CF3—Ph | O | null |
| 240 | 401.98 | 401.95 | 1 | 1 | 3-Br-4-F—Ph | O | null |
| 241 | 404.00 | 404.03 | 1 | 1 | 3-Br-4-F—Ph | OH | H |
| 244 | 385.99 | 386.02 | CH | 1 | 3-Br-4-F—Ph | H | null |
| 246 | 423.98 | 423.95 | 1 | 1 | 3-Br-4-F—Ph | F | F |
| 247 | 402.14 | 402.17 | 2 | 0 | 3-CF3—Ph | Propyl | H |
| 248 | 428.05 | 428.05 | 2 | 0 | 3-Br-4-Ome—Ph | Ethyl | H |
| 249 | 414.04 | 414.00 | 2 | 0 | 3-Br-4-Ome—Ph | Methyl | H |
| 250 | 428.05 | 428.05 | 2 | 0 | 3-Br-4-Ome—Ph (syn) | Ethyl | H |
| 251 | 428.05 | 428.05 | 2 | 0 | 3-Br-4-Ome—Ph (anti) | Ethyl | H |
| 252 | 392.10 | 392.13 | 1 | 2 | 3-CF3-5-F—Ph | H | H |
| 253 | 375.10 | 375.06 | 1 | 2 | 6-CF3-pyrid-2-yl | H | H |
| 273 | 359.03 | 358.99 | CONN | 1 | 3-Cl-4-F—Ph | H | H |
| 293 | 360.05 | 360.01 | 1 | 1 | 3-Cl-4-F—Ph | OH | H |
| 304 | 507.16 | 507.12 | 0 | 2 | 3-CF3-5-F—Ph | O-Ethyl-Morpholine | H |
| 310 | 394.07 | 394.07 | 0 | 2 | 3-CF3-5-F—Ph (Anti) | H | OH |
| 311 | 394.07 | 394.07 | 0 | 2 | 3-CF3-5-F—Ph (syn) | OH | H |
| 312 | 396.07 | 396.07 | 0 | 2 | 3-CF3-5-F—Ph (Anti) | H | F |
| 313 | 396.07 | 396.07 | 0 | 2 | 3-CF3-5-F—Ph (syn) | F | H |
| 342 | 407.11 | 407.11 | 1 | 1 | 3-CF3-5-F—Ph | NHMe | H |
| 367 | 375.06 | 375.06 | 1 | CONH | 3-Cl-4-F—Ph | H | H |
| 383 | 402.10 | 402.14 | 2 | 0 | 3-CF3—Ph | CH2OCH2 | |
| 384 | 390.10 | 390.06 | 0 | 2 | 3-CF3—Ph | OMe | H |
| 385 | 418.01 | 418.05 | 0 | 2 | 3-F-4-Br—Ph | OMe | H |
| 386 | 402.10 | 402.10 | 0 | 2 | 3-CF3—Ph | CH2OCH2 | |
| 387 | 430.01 | 430.01 | 0 | 2 | 3-F-4-Br—Ph | CH2OCH2 | |
| 394 | 372.11 | 372.07 | 2 | 0 | 3-CF3—Ph (anti) | H | OMe |
| 416 | 390.10 | 390.10 | 2 | 0 | 3-CF3—Ph (syn) | OMe | H |
| 418 | 421.12 | 421.12 | 0 | 2 | 3-F-5-CF3—Ph | N,N-DiMe | H |
| 424 | 420.13 | 420.13 | 2 | 0 | 3-CF3—Ph | Propyl | F |
| 448 | 360.09 | 360.09 | 0 | 1 | 3-CF3—Ph | Me | H |
| 450 | 378.08 | 378.04 | 0 | 1 | 3-CF3-5-F—Ph | Me | H |
| 457 | 432.05 | 432.02 | 0 | 1 | 3-CF3-5-F—Ph | CF3 | H |
| 464 | 348.03 | 348.06 | 0 | 1 | 3-Cl-4-F—Ph | F | H |
| 466 | 421.99 | 421.99 | 0 | 1 | 3-Br-4-OMe—Ph | F | F |
| 467 | 382.05 | 382.05 | 0 | 1 | 3-CF3—Ph | F | F |
| 468 | 382.05 | 382.02 | 0 | 1 | 3-CF3-5-F—Ph | F | H |
| 473 | 414.06 | 414.06 | 0 | 1 | 3-CF3—Ph | CF3 | H |
| 476 | 398.03 | 397.99 | 0 | 1 | 3-Cl-4-F—Ph | CF3 | H |
| 481 | 365.06 | 365.10 | 0 | 1 | 6-CF3-pyrid-2-yl | F | H |
| 482 | 383.05 | 383.01 | 0 | 1 | 6-CF3-pyrid-2-yl | F | F |

TABLE 16

Example compounds prepared via Method 4 with given core structure. *1 indicates earlier eluting enantiomer. *2 indicates later eluting enantiomer. *3 indicates trans-diastereomeric relationship between R2 and F.

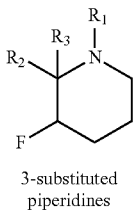

3-substituted piperidines

| Number | Exp M + H | Obs M + H | R1 | R2 | R3 |
|---|---|---|---|---|---|
| 203 | 401.04 | 401.00 | 3-Cl—Bn | 3-Br-4-F—Ph | D |
| 204 | 373.12 | 373.10 | 3-Cl—Bn | 3-CF$_3$—Ph | D |
| 205 | 391.11 | 391.10 | 2-F-3-Cl—Bn | 3-CF$_3$—Ph | D |
| 206 | 417.07 | 417.05 | 3-Br—Bn | 3-CF$_3$—Ph | D |
| 207 | 379.09 | 379.05 | 2-Cl-5-F-pyrimidin-4-yl | 3-CF$_3$—Ph | D |
| 208 | 379.05 | 379.08 | 2-Cl-5-F-pyrimidin-4-yl | 3-CF$_3$—Ph (*1) | D |
| 209 | 379.05 | 379.08 | 2-Cl-5-F-pyrimidin-4-yl | 3-CF$_3$—Ph (*2) | D |
| 210 | 406.00 | 405.95 | 2-Cl-5-F-pyrimidin-4-yl | 3-Br-4-F—Ph | D |
| 211 | 405.95 | 405.99 | 2-Cl-5-F-pyrimidin-4-yl | 3-Br-4-F—Ph (syn) | H |
| 212 | 418.00 | 418.02 | 2-Cl-5-F-pyrimidin-4-yl | 3-Br-4-OMe—Ph | H |
| 213 | 418.00 | 418.02 | 2-Cl-5-F-pyrimidin-4-yl | 3-Br-4-OMe—Ph (syn) | H |
| 214 | 406.95 | 407.00 | 2-Cl-5-F-pyrimidin-4-yl | 3-Br-4-F—Ph (syn) | D |
| 219 | 461.95 | 461.99 | 4-Cl-Ph-Sulfonyl | 3-Br-4-OMe—Ph | H |
| 440 | 391.11 | 391.11 | 2-F-5-Cl—Bn | 3-CF3—Ph | D |
| 441 | 391.11 | 391.15 | 3-Cl-5-F—Bn | 3-CF3—Ph | D |
| 442 | 407.08 | 407.05 | 2,5-diCl—Bn | 3-CF3—Ph | D |

TABLE 17

Example compounds prepared via Method 1, steps 5b-5d with given core structure. A "*" indicates a compound made via Method 8.

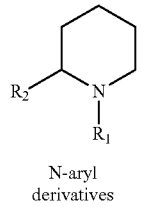

N-aryl derivatives

| Compound No. | Expect M + H | Observed M + H | R1 | R2 |
|---|---|---|---|---|
| 132 | 400.02 | 400.00 | 2-Cl-5-F-pyrimid-4-yl | 3-Br-4-OMe—Ph |
| 215 | 399.03 | 399.00 | 2-Cl-4-F-pyridin-6-yl | 3-Br-4-OMe—Ph |
| 218 | 314.11 | 314.10 | 3-CN—Ph * | 3-Cl-4-F—Ph |
| 225 | 396.08 | 396.07 | 2-OMe-5-F-pyrimidin-4-yl | 3-Br-4-OMe—Ph |
| 226 | 382.04 | 382.03 | 2-Cl-pyrimidin-4-yl | 3-Br-4-OMe—Ph |
| 227 | 415.07 | 415.06 | 2-CF3-pyridin-6-yl | 3-Br-4-OMe—Ph |
| 228 | 400.02 | 400.02 | 6-Cl-5-F-pyrimidin-4-yl | 3-Br-4-OMe—Ph |
| 229 | 382.04 | 382.03 | 6-Cl-pyrizin-2-yl | 3-Br-4-OMe—Ph |
| 230 | 416.06 | 416.06 | 6-CF3-pyrizin-2-yl | 3-Br-4-OMe—Ph |
| 231 | 424.99 | 424.99 | 5-Br-pyridin-2-yl | 3-Br-4-OMe—Ph |
| 232 | 415.07 | 415.06 | 5-CF3-pyridin-2-yl | 3-Br-4-OMe—Ph |
| 233 | 366.07 | 366.06 | 5-F-pyrimidin-4-yl | 3-Br-4-OMe—Ph |
| 234 | 396.05 | 396.05 | 2-Cl-5-Me-pyrimidin-4-yl | 3-Br-4-OMe—Ph |
| 235 | 412.05 | 412.04 | 2-Cl-5-OMe-pyrimidin-4-yl | 3-Br-4-OMe—Ph |
| 236 | 396.05 | 396.05 | 6-Cl-5-Me-pyrimidin-2-yl | 3-Br-4-OMe—Ph |
| 242 | 320.17 | 320.20 | 2-N,N-DiMe-5-F-pyrimid-4-yl | 6-F-pyrid-2-yl |
| 243 | 345.22 | 345.26 | 2-N,N-DiMe-5-F-pyrimid-4-yl | 6-N,N-DiMe-pyrid-2-yl |
| 254 | 397.20 | 397.17 | 2-N,N-DiEt-5-F-pyrimid-4-yl | 3-CF3—Ph* |
| 255 | 411.18 | 411.18 | 2-morpholino-5-F-pyrimid-4-yl | 3-CF3—Ph* |
| 256 | 397.17 | 397.20 | 2-N-(3-hydroxyazetidine)-5-F-pyrimid-4-yl | 3-CF3—Ph* |
| 257 | 342.10 | 342.13 | 2-Cl-pyrimid-4-yl | 3-CF3—Ph |
| 258 | 342.10 | 342.13 | 4-Cl-pyrimid-2-yl | 3-CF3—Ph |
| 259 | 293.10 | 293.10 | 2-Cl-pyrimid-4-yl | 6-F-pyrid-2-yl |
| 260 | 293.10 | 293.13 | 4-Cl-pyrimid-2-yl | 6-F-pyrid-2-yl |
| 261 | 359.09 | 359.06 | 2-Cl-5-F-pyrid-4-yl | 3-CF3—Ph |

TABLE 17-continued

Example compounds prepared via Method 1, steps 5b-5d with given core structure.
A "*" indicates a compound made via Method 8.

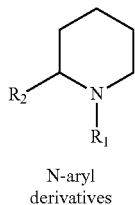

N-aryl derivatives

| Compound No. | Expect M + H | Observed M + H | R1 | R2 |
|---|---|---|---|---|
| 262 | 310.09 | 310.06 | 2-Cl-5-F-pyrid-4-yl | 6-F-pyrid-2-yl |
| 263 | 359.09 | 359.13 | 3-F-6-Cl-pyrid-2-yl | 3-CF3—Ph |
| 264 | 310.09 | 310.06 | 3-F-6-Cl-pyrid-2-yl | 6-F-pyrid-2-yl |
| 265 | 356.11 | 356.08 | 2-Cl-5-Me-pyrimidin-4-yl | 3-CF3—Ph |
| 266 | 356.11 | 356.15 | 4-Cl-5-Me-pyrimidin-2-yl | 3-CF3—Ph |
| 267 | 307.11 | 307.11 | 2-Cl-5-Me-pyrimidin-4-yl | 6-F-pyrid-2-yl |
| 268 | 307.11 | 307.15 | 4-Cl-5-Me-pyrimidin-2-yl | 6-F-pyrid-2-yl |
| 269 | 340.14 | 340.14 | 2-Me-5-F-pyrimidin-4-yl | 3-CF3—Ph |
| 270 | 291.14 | 291.11 | 2-Me-5-F-pyrimidin-4-yl | 6-F-pyrid-2-yl |
| 271 | 356.14 | 356.10 | 2-OMe-5-F-pyrimidin-4-yl | 3-CF3—Ph |
| 272 | 307.14 | 307.14 | 2-OMe-5-F-pyrimidin-4-yl | 6-F-pyrid-2-yl |
| 295 | 356.14 | 356.17 | 2-OMe-4-F-Pyrimid-5-yl | 3-CF3—Ph |
| 296 | 307.14 | 307.10 | 2-OMe-4-F-Pyrimid-5-yl | 6-F-pyrid-2-yl |
| 349 | 342.12 | 342.12 | 2-hydroxy-5-F-Pyrimid-4-yl | 3-CF3—Ph |
| 350 | 342.12 | 342.16 | 2-hydroxy-5-F-Pyrimid-4-yl | 3-CF3—Ph |
| 351 | 360.09 | 360.05 | 5-F-6-Cl-pyrimid-4-yl | 3-CF3—Ph |
| 356 | 342.12 | 342.16 | 6-hydroxy-5-F-Pyrimid-4-yl | 3-CF3—Ph |
| 359 | 341.10 | 341.07 | 2-Cl-pyrid-4-yl | 3-CF3—Ph |
| 360 | 342.10 | 342.10 | 6-Cl-pyrimid-4-yl | 3-CF3—Ph |
| 361 | 372.11 | 372.11 | 2-Cl-5-OMe-pyrimid-4-yl | 3-CF3—Ph |
| 365 | 360.09 | 360.05 | 2-Cl-pyrimid-4-yl | 2-F-3-CF3—Ph |
| 368 | 344.12 | 344.08 | 2,5-Di-F-Pyrimid-4-yl | 3-CF3—Ph |
| 381 | 307.11 | 307.08 | 3-F-6-Cl-5-Pyrid-2-yl | 2-Me-primid-4-yl |
| 382 | 293.10 | 293.10 | 3-F-6-Cl-5-Pyrid-2-yl | pyrimid-5-yl |
| 395 | 327.06 | 327.02 | 3-F-6-Cl-5-Pyrid-2-yl | 6-Cl-Pyrazin-2-yl |
| 396 | 290.12 | 290.12 | 2-Me-pyrimid-4-yl | 6-Cl-Pyrazin-2-yl |
| 401 | 324.13 | 324.13 | 2-hydroxy-pyrimid-4-yl | 3-CF3—Ph |
| 402 | 359.09 | 359.13 | 2-Cl-3-F-pyrid-4-yl | 3-CF3—Ph |
| 403 | 360.09 | 360.05 | 2-Cl-pyrimid-4-yl | 2-F-5-CF3—Ph |
| 405 | 326.06 | 326.06 | 2-Cl-pyrimid-4-yl | 2-F-3-Cl—Ph |
| 406 | 326.06 | 326.03 | 2-Cl-pyrimid-4-yl | 2-F-5-Cl—Ph |
| 415 | 360.09 | 360.09 | 6-Cl-3-F-pyrid-2-yl | 2-CF3-5-pyrid-5-yl |
| 443 | 324.07 | 324.07 | 3-Cl—Ph* | 3-Cl-4-F—Ph |
| 447 | 346.14 | 346.10 | 2,3-dihydro-1H-inden-2-ol-1-yl | 3-Cl-4-F—Ph |
| 449 | 424.02 | 424.02 | 2-Cl-3-CN-5-F-pyrid-6-yl | 3-Br-4-OMe—Ph |
| 451 | 331.14 | 331.14 | 3-ethynyl-Ph | 6-CF3-pyrid-2-yl |
| 452 | 375.13 | 375.13 | 4-CF3—Ph* | 6-CF3-pyrid-2-yl |
| 453 | 358.10 | 358.06 | 4-CF3—Ph* | 3-Cl-4-F—Ph |
| 454 | 341.10 | 341.10 | 4-Cl—Ph* | 6-CF3-pyrid-2-yl |
| 455 | 337.15 | 337.19 | 3-OMe—Ph* | 6-CF3-pyrid-2-yl |
| 458 | 304.13 | 304.09 | 4-Me—Ph* | 3-Cl-4-F—Ph |
| 459 | 341.10 | 341.10 | 3-Cl—Ph* | 6-CF3-pyrid-2-yl |
| 461 | 340.10 | 340.07 | 2-OMe-5-F-pyrimidin-4-yl | 3-Cl-4-F—Ph |
| 462 | 331.11 | 331.15 | 4-azido-Ph* | 3-Cl-4-F—Ph |
| 463 | 314.11 | 314.15 | 2-ethynyl-Ph* | 3-Cl-4-F—Ph |
| 465 | 320.12 | 320.09 | 3-OMe—Ph* | 3-Cl-4-F—Ph |
| 469 | 343.09 | 343.06 | 2-Cl-pyrimid-4-yl | 6-CF3-pyrid-2-yl |
| 470 | 326.06 | 326.03 | 2-Cl-pyrimid-4-yl | 3-Cl-4-F—Ph |
| 471 | 318.14 | 318.18 | 3,5-DiMe-Ph* | 3-Cl-4-F—Ph |
| 474 | 337.15 | 337.19 | 4-OMe—Ph* | 6-CF3-pyrid-2-yl |
| 475 | 308.10 | 308.10 | 4-F—Ph* | 3-Cl-4-F—Ph |
| 477 | 348.12 | 348.08 | methl 4-benzoate* | 3-Cl-4-F—Ph |
| 478 | 365.15 | 365.11 | methl 4-benzoate* | 6-CF3-pyrid-2-yl |
| 479 | 376.16 | 376.16 | 2-morpholino-pyrid-3-yl* | 3-Cl-4-F—Ph |
| 480 | 306.12 | 306.12 | 2-Me-pyrimid-4-yl | 3-Cl-4-F—Ph |

Methods for Providing Pain Relief by Administration of MOR PAMs

Although agonists that are highly selective with respect to the different opioid receptor types exist, they are still beset by numerous side effects. Many of the side effects of these receptor-selective agonists are not due to off-target effects, but result from indiscriminate activation all receptors throughout the body; thereby activating MORs in tissues or regions of the CNS in which receptor activation is undesirable (i.e., areas in which pain is not being experienced).

Such side effects are unlikely to be addressed by the development of more highly selective agonists.

Thus, one advantage of the disclosed methods and compositions is the capability of MOR PAMs, when administered in vivo in the absence of an exogenous orthosteric MOR ligand, to selectively increase receptor activity only in regions where endogenous agonists are present, thereby preserving the temporally- and spatially-limited nature of the endogenous opioid response. This property of MOR-PAMs will result in fewer "on-target" (i.e., MOR-mediated) side effects compared to the use of a MOR agonist.

Another advantage of the MOR PAMs disclosed herein is that their use avoids the sustained receptor activation that ensues between administration and clearance of an exogenous opioid. Thus, the use of MOR PAMs will minimize compensatory mechanisms, such as receptor downregulation and desensitization, that can lead to tolerance and/or dependence.

Because of the known basal activity of endogenous opioids (Roques et al. (2012) Nat. Rev. Drug Discov. 11:292-310; Levine et al. (1978) Nature 272:826-827), administration of a MOR PAM, in the absence of an exogenous opioid, will provide an analgesic effect, by increasing the baseline activity of the endogenous opioid. See example 9.

The MOR PAM compounds described herein are useful for treatment of clinical acute pain, inflammatory pain, and for a variety of other uses. Alternatively, in a chronic pain situation, it is known that there are temporal and spatial relationships between the physiological releases of endogenous MOR ligands in inflamed and non-inflamed tissues. Thus, the MOR PAMs disclosed herein additionally provide methods for chronic pain studies wherein the pharmacodynamic measurements are designed such that pain measurement post onset of chronic pain is decreased, and/or there is a decrease and/or delay in the intensity of the development of chronic pain and/or a delay in the onset of chronic pain.

Pharmaceutical Compositions and Formulations

Various pharmaceutical compositions and techniques for their preparation and use are known to those of skill in the art in light of the present disclosure. For a detailed listing of suitable pharmacological compositions and techniques for their administration one may refer to texts such as Remington's Pharmaceutical Sciences, 17th ed. 1985; Brunton et al., "Goodman and Gilman's The Pharmacological Basis of Therapeutics," McGraw-Hill, 2005; University of the Sciences in Philadelphia (eds.), "Remington: The Science and Practice of Pharmacy," Lippincott Williams & Wilkins, 2005; and University of the Sciences in Philadelphia (eds.), "Remington: The Principles of Pharmacy Practice," Lippincott Williams & Wilkins, 2008.

Pharmaceutical compositions can be formulated by standard techniques using one or more physiologically acceptable carriers or excipients. The formulations can contain a buffer and/or a preservative. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally in a vehicle comprising one or more pharmaceutically acceptable carriers, the proportion of which is determined by the solubility and chemical nature of the compound, chosen route of administration and standard biological and pharmacological practices.

Additional routes of administration include, but are not limited to, transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, or by oral administration.

Pharmaceutical compositions can include effective amounts of one or more compound(s) described herein together with, for example, pharmaceutically acceptable diluents, preservatives, solubilizers, emulsifiers, adjuvants and/or other carriers. Such compositions can include diluents of various buffer content (e.g., TRIS or other amines, carbonates, phosphates, amino acids, for example, glycinamide hydrochloride (especially in the physiological pH range), N-glycylglycine, sodium or potassium phosphate (dibasic, tribasic), etc., TRIS-HCl or TRIS-acetate), pH and ionic strength; additives such as detergents and solubilizing agents (e.g., surfactants such as Pluronics, Tween 20, Tween 80, Polysorbate 80, Cremophor, polyols such as polyethylene glycol, propylene glycol, etc.), anti-oxidants (e.g., ascorbic acid, sodium metabisulfite), preservatives (e.g., Thimersol, benzyl alcohol, parabens, etc.) and bulking substances (e.g., sugars such as sucrose, lactose, mannitol, polymers such as polyvinylpyrrolidones or dextran, etc.); and/or incorporation of the material into particulate preparations of polymeric compounds such as polylactic acid, polyglycolic acid, etc. or into liposomes. Hyaluronic acid may also be used.

Such compositions can be employed to influence the physical state, stability, rate of in vivo release, and rate of in vivo clearance of a compound described herein. See, e.g., Remington's Pharmaceutical Sciences, 18th Ed. (1990, Mack Publishing Co., Easton, Pa. 18042) pages 1435-1712 which are hereby incorporated herein by reference. The compositions can, for example, be prepared in liquid form, or can be in dried powder, such as lyophilized form. Particular methods of administering such compositions are described infra.

If a buffer is to be included in the formulations described herein, the buffer can be selected from sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethane, or mixtures thereof. The buffer can also be glycylglycine, sodium dihydrogen phosphate, disodium hydrogen phosphate, and sodium phosphate or mixtures thereof. If a pharmaceutically acceptable preservative is to be included in a formulation of one of the compounds described herein, the preservative can be selected from phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof. The preservative can also be phenol or m-cresol.

The terms "pharmaceutically acceptable" and "therapeutically acceptable" refer to molecular entities and compositions that are physiologically tolerable and preferably do not typically produce an allergic or similar untoward reaction, such as gastric upset, dizziness and the like, when administered to a subject (e.g., a human).

In some embodiments, the compounds described herein can be administered by any suitable route, including, but not limited to, via inhalation, topically, nasally, orally, parenterally (e.g., intravenously, intraperitoneally, intravesically or intrathecally) or rectally in a vehicle comprising one or more pharmaceutically acceptable carriers, the proportion of which is determined by the solubility and chemical nature of the compound, chosen route of administration and standard practice. Administration of the compounds described herein can be carried out using any method known in the art. For example, administration may be transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, or by oral administration. A pharmaceutical composition of the compounds described herein can be for administration for injection, or for oral, pulmonary, nasal, transdermal, or ocular administration.

Exemplary formulations include, but are not limited to, those suitable for parenteral administration, e.g., intrapulmonary, intravenous, intra-arterial, intra-ocular, intra-cranial, sub-meningial, or subcutaneous administration, including formulations encapsulated in micelles, liposomes or drug-release capsules (active agents incorporated within a biocompatible coating designed for slow-release); ingestible formulations; formulations for topical use, such as eye drops, creams, ointments and gels; and other formulations such as inhalants, aerosols and sprays. The dosage of the compositions of the disclosure will vary according to the extent and severity of the need for treatment, the activity of the administered composition, the general health of the subject, and other considerations well known to the skilled artisan.

In additional embodiments, the compositions described herein are delivered locally. Localized delivery allows for the delivery of the composition non-systemically, thereby reducing the body burden of the composition as compared to systemic delivery. Such local delivery can be achieved, for example, through the use of various medically implanted devices including, but not limited to, stents and catheters, or can be achieved by inhalation, injection or surgery. Methods for coating, implanting, embedding, and otherwise attaching desired agents to medical devices such as stents and catheters are established in the art and contemplated herein.

For oral administration, the pharmaceutical composition of the compounds described herein can be formulated in unit dosage forms such as capsules or tablets. The tablets or capsules can be prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate.

Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

The compounds described herein can also include derivatives referred to as prodrugs, which can be prepared by modifying functional groups present in the compounds in such a way that the modifications are removed (e.g., cleaved), either in routine manipulation or in vivo, to regenerate the parent compounds. Examples of prodrugs include compounds of the invention as described herein that contain one or more molecular moieties appended to a hydroxyl, amino, sulfhydryl, or carboxyl group of the compound, and that when administered to a patient, are cleaved in vivo to form the free hydroxyl, amino, sulfhydryl, or carboxyl group, respectively. Examples of prodrugs include, but are not limited to, acetate, formate and benzoate derivatives of alcohol and amine functional groups in the compounds described herein. Preparation and use of prodrugs is discussed, for example, in T. Higuchi et al., "Pro-drugs as Novel Delivery Systems," Vol. 14 of the A.C.S. Symposium Series, and in "Bioreversible Carriers in Drug Design," ed. Edward B. Roche, American Pharmaceutical Association and Pergamon Press, 1987, both of which are incorporated herein by reference in their entireties.

Dosages

The compounds described herein can be administered to a subject at therapeutically effective doses to prevent, treat, or control one or more diseases and disorders mediated, in whole or in part, by an OR-ligand interaction. The compounds can also be administered, either alone or in combination with other substances, for pain relief, induction of analgesia, reduction of nociception and/or to potentiate the effect of an endogenous or exogenous opioid. Pharmaceutical compositions comprising one or more of compounds described herein can be administered to a patient in an amount sufficient to elicit an effective protective, therapeutic or analgesic response in a subject. An amount adequate to accomplish any of these is defined as a "therapeutically effective dose." A therapeutically effective dose is determined by the efficacy of the particular compound employed and the condition of the subject, as well as the body weight or surface area of the region to be treated. The size of the dose can also be influenced by the existence, nature, and extent of any adverse effects that accompany the administration of a particular compound or vector in a particular subject.

Toxicity and therapeutic efficacy of compounds can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. In some embodiments, compounds that exhibit large therapeutic indices are used. While compounds that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. In some embodiments, the dosage of such compounds lies within a range of circulating concentrations that include the $ED_{50}$ and that exhibits little or no toxicity. The dosage can vary within this range depending upon the dosage form employed and the route of administration and other factors, including the condition of the subject. For any compound described herein, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject. In certain embodiments, the dose level is between 10 ng/kg and 1 mg/kg; in other embodiments, between 100 ng/kg and 0.1 mg/kg; in other embodiments, between 1 μg/kg and 10 μg/kg. In additional embodiments, the dose range for a compound as described herein is between 1-100 ng/kg, or 10-1,000 ng/kg, or 0.1-10 μg/kg, or 10-100 μg/kg, or 0.1-1 mg/kg, or 1-10 mg/kg.

The amount and frequency of administration of the compounds described herein and/or the pharmaceutically acceptable salts thereof is regulated according to the judgment of the attending clinician considering such factors as age, condition and size of the subject as well as severity of the symptoms being treated. An ordinarily skilled physician or veterinarian can readily determine and prescribe an effective amount of a compound suitable to prevent, counter or arrest the progress of the condition. In general, it is contemplated that an effective amount would be from 0.001 mg/kg to 10 mg/kg body weight, and in particular from 0.01 mg/kg to 1 mg/kg body weight. It may be appropriate to administer the required dose as two, three, four or more sub-doses at appropriate intervals throughout the day. Said sub-doses can be formulated as unit dosage forms, for example, containing 0.01 to 500 mg, and in particular 0.1 mg to 200 mg of active ingredient per unit dosage form.

Medical Uses

The compositions described herein are useful for treating pain or pain-associated disorders such as, for example, immune dysfunction, inflammation, esophageal reflux, neurological conditions, psychiatric conditions, urological conditions, sexual dysfunction and reproductive conditions. They are also useful as medicaments for drug and alcohol abuse, agents for treating gastritis and diarrhea, cardiovascular agents and agents for the treatment of respiratory diseases and cough.

In some embodiments, methods of treating pain are provided. In some embodiments, one or more compounds described herein are administered to a subject to treat the pain. In some embodiments, the pain can be post-operative pain. In some embodiments, the pain is caused by cancer. In additional embodiments, the pain is caused by chemotherapy (chemotherapy-induced neuropathic pain, CINP). In some embodiments, the pain is associated with inflammation (i.e., inflammatory pain). In some embodiments, the pain is neuropathic pain. In some embodiments, the pain is caused by trauma, such as but not limited to, blunt force trauma. In additional embodiments, the pain can result from endocrine imbalances, such as those resulting, e.g., from diabetes.

Kits

Another aspect of the present disclosure relates to kits for carrying out the administration of MOR PAMs to a subject. In one embodiment, a kit comprises a composition comprising one or more MOR PAM(s), formulated as appropriate (e.g., in a pharmaceutical carrier), in one or more separate pharmaceutical preparations. Kits can also contain devices for administration of the composition(s) and/or instructions for use.

EXAMPLES

Example 1: Receptor Activation Assays

The ability of compounds to stimulate OR mediated signaling can be measured using any assay known in the art to detect OR mediated signaling or OR activity, or the absence of such signaling or activity. "OR activity" refers to the ability of an OR to transduce a signal. Such activity can be measured, e.g., in a heterologous cell, by coupling an OR (or a chimeric OR) to a downstream effector such as adenylate cyclase.

The effects of MOR PAMs and MOR SAMs on receptor activity were assayed using the PathHunter enzyme complementation assay technology (DiscoveRx, CA). A description of the technology employed is as follows.

Beta-Arrestin Pathway:

The PathHunter β-arrestin assay monitors the activation of a GPCR in a homogenous, non-imaging assay format using a technology developed by DiscoveRx called Enzyme Fragment Complementation (EFC) with beta-galactosidase (β-Gal) as the functional reporter. The enzyme is split into two inactive complementary portions (EA for Enzyme Acceptor and ED for Enzyme Donor) expressed as fusion proteins in the cell. EA is fused to β-Arrestin and ED is fused to the GPCR of interest. When the GPCR is activated and β-arrestin is recruited to the receptor, ED and EA complementation occurs, restoring β-gal activity, which is measured using chemiluminescent PathHunter Detection Reagents.

cAMP Secondary Messenger Pathway:

A cell line expressing stable MOR that signals through cAMP is used to quantify the activity of ligands for this secondary pathway. Hit Hunter® cAMP assays monitor the activation of a MOR via Gi and Gs secondary messenger signaling in a homogenous, non-imaging assay format EFC with β-gal as the functional reporter.

Example 2: Allosteric Activity of Selected Compounds

Identification of positive allosteric modulators was performed in the presence of an $EC_{20}$ concentration (40 nM) of the MOR-specific orthosteric agonist endomorphin-1. In this manner an $EC_{50}$ for each test compound, and percent maximal response for each test compound, were determined for both the β-arrestin and cAMP pathways. Though the pharmacological effects of a given signal bias can be hypothesized (Raehal et al. (2011) *Pharmacol. Rev.* 63:1001-1019), it is not possible to know with certainty which bias ratio will be most advantageous in a clinical setting. Compounding this issue is evidence that clinically used mixed agonist/ partial agonist drugs for the MOR have significantly different ligand bias. Kenakin 2015a, supra. The information associated with the compounds detailed herein is the first large data set available for the prediction of ligand bias for an MOR PAM. Example concentration response curves are given in FIGS. 1A-5B.

Based on these assays, the compounds can be divided into a number of categories, for example: (A) Relative ratio of $EC_{50}$ for β-arrestin vs. cAMP (greater than, equal, or less than), (B) Maximal response of β-arrestin efficacy (silent, partial or full efficacy), (C) Maximal response of the cAMP efficacy (silent, partial or full efficacy), (D) the relative ratio of (B) to (C) and (E) the absolute values of the $EC_{50}$ values for β-arrestin vs cAMP amongst compounds (high, moderate, and low potency). Exemplary data are provided in Tables 3 and 4 above. Compound No. 14 (FIGS. 3A and 3B) is an example of a compound with dual silent allosteric modulation of MOR with respect to either β-arrestin or cAMP signaling. Compound No. 44 (Table 8) (FIGS. 1A and 1B) is an example of a moderately potent compound that would be expected to have equivalent effects on β-arrestin recruitment and cAMP signaling. Compound No. 219 (Table 16) (FIGS. 2A and 2B) is an example of a moderately potent compound that would be expected to have preferential signaling via cAMP over β-arrestin. Compound No. 216 (Table 11) (FIGS. 4A and 4B) is an example of a compound that displays high allosteric modulatory capability for β-arrestin recruitment and silent allosteric activity with respect to cAMP signaling. Compound No. 2 (Table 12) (FIGS. 5A and 5B) is an example of a potent compound that would be expected to have roughly equivalent signaling for β-arrestin and cAMP.

Example 3: Lack of Agonist Activity by Compounds

To demonstrate that the compounds detailed herein display a pure PAM mechanism and do not have residual agonist or antagonist activity toward the MOR, five compounds displaying MOR PAM activity (see FIGS. 6A-6J) were tested for both agonist and antagonist activity against the MOR, using a β-arrestin recruitment assay with the mu opioid receptor subtype OPRM1 as the assay target. Agonist activity of endomorphin-1 was used as a positive control. The results shown in Table 18 demonstrate that these five diverse compounds do not show agonist or antagonist activity toward the MOR as assayed by β-arrestin recruitment. Similar results were obtained when agonist and antagonist activity were assayed using cAMP signaling as the readout.

TABLE 18

Lack of agonist or antagonist activity of certain compounds as tested by effects on β-arrestin recruitment

| Compound | Assay format | $EC_{50}$ (µM) | $IC_{50}$ (µM) |
| --- | --- | --- | --- |
| 108 | agonist | >25 | |
| 108 | antagonist | | >25 |
| 177 | agonist | >25 | |
| 177 | antagonist | | >25 |
| 6 | agonist | >25 | |
| 6 | antagonist | | >25 |
| 110 | agonist | >25 | |
| 110 | antagonist | | >25 |
| 109 | agonist | >25 | |
| 109 | antagonist | | >25 |
| endomorphin-1 | agonist | 0.04889 | |

Example 4: Concentration Dependence

Concentration-response curves (CRCs) for EM1-mediated cAMP signaling and β-arrestin recruitment were generated in the absence or presence of varying concentrations of compound No. 9 (Table 10). The full functional allosteric model for response (Kenakin (2005) *Nature Reviews Drug Discovery* 4:919-927; Price et al. (2005) *Mol. Pharmacol.* 68:1484-1495; Ehlert (2005) *J. Pharmacol. Exp. Ther.* 315: 740-754) was applied to DR curves for EM1-mediated responses for β-arrestin and cAMP. This model estimates the equilibrium dissociation constant of the modulator ($K_B$), the cooperative effect of the modulator on agonist affinity (α) and cooperative effect of the modulator on agonist efficacy (β).

Compound 9 produced concentration-dependent and saturable leftward shifts in the potency of EM1 in both β-arrestin (FIG. 7A) and cAMP (FIG. 7B) assays. With respect to β-arrestin signaling, compound 9 increased the affinity (α) of EM1 by a factor of 9 and increased the efficacy (β) of EM1 by a factor of 3; resulting in an effective potency for PAM effect with respect to the β-arrestin signal of 70.8 nM. With respect to cAMP signaling, compound 9 increased the affinity (α) of EM1 by a factor of 2 and increased the efficacy (β) of EM1 by a factor of 1.8; resulting in an effective potency for PAM effect with respect to cAMP signaling of 44 nM.

Example 5: Receptor Specificity

Allosteric ligands have the potential to exhibit greater selectivity between subtypes of GPCRs in the same family compared with orthosteric ligands. This effect has been demonstrated for some GPCRs including metabotropic glutamate receptors, adenosine receptors and muscarinic receptors. Birdsall, supra; Conn et al., supra; Gao et al., supra; Gasparini et al. (2002) *Curr. Opin. Pharmacol.* 2:43-49. It has been hypothesized that this selectivity arises from the evolutionary constraint placed on the orthosteric site between closely related receptor subtypes that bind the same endogenous ligand. This proposed evolutionary constraint may or may not be present with respect to allosteric binding sites.

Figure 8A:
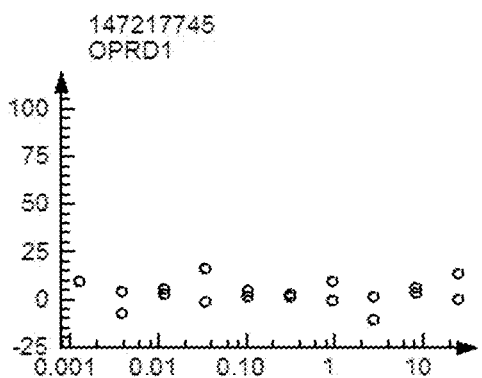
FIG. 8A shows the effect of increasing concentration of compound 60 on β-arrestin recruitment by the delta opioid receptor (DOR) induced by an $EC_{20}$ concentration of the DOR agonist d-Ala$^2$, D-Leu$^5$-enkephalin (DADLE).
Figure 8B:
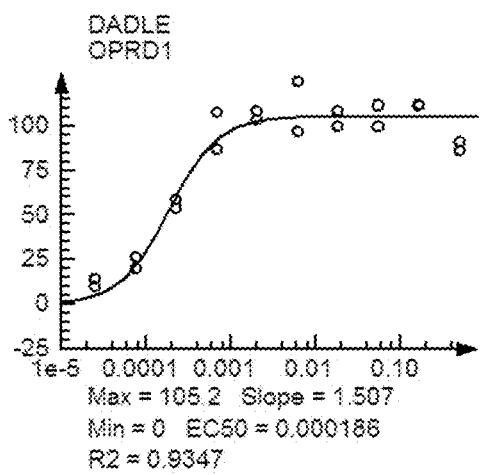
FIG. 8B shows the effect of increasing concentrations of DADLE on β-arrestin recruitment by the delta opioid receptor.

To test whether the MOR PAMs disclosed herein have effects on opioid receptors other than the MOR, compound 60 was examined in β-arrestin recruitment assays using U2OS Path Hunter® cells expressing either PK-tagged delta opioid receptors (U2OS-DOR1) or PK-tagged kappa opioid receptors (U2OS-KOR1). At concentrations up to 25 µM, compound 60 had no significant positive allosteric effect on DOR signaling in the presence of an $EC_{20}$ concentration (0.8 nM) of the delta opioid receptor agonist [D-Ala2, D-Leu5]-Enkephalin (DADLE) (FIG. 8A). The agonist activity of DADLE on the DOR is shown in FIG. 8B for comparison.

Figure 9A:
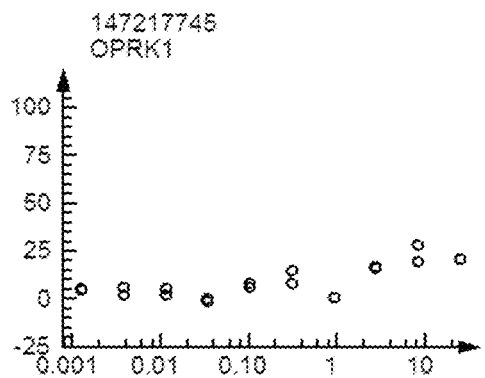
FIG. 9A shows the effect of increasing concentration of compound 60 on β-arrestin recruitment by the kappa opioid receptor (KOR) induced by an $EC_{20}$ concentration of the KOR agonist Dynorphin A.
Figure 9B:
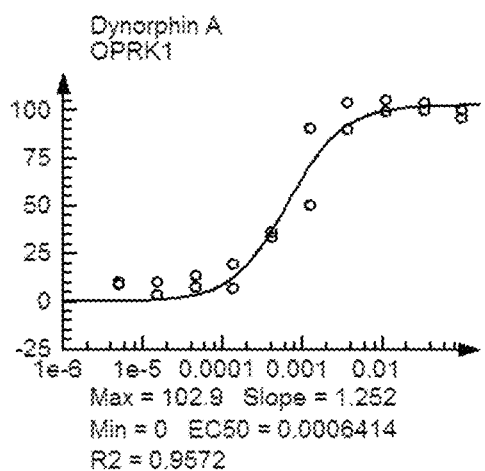
FIG. 9B shows the effect of increasing concentrations of Dynorphin A on β-arrestin recruitment by the kappa opioid receptor.

Similarly, at concentrations up to 25 µM, compound 60 had no significant positive allosteric effect on KOR signaling in the presence of an $EC_{20}$ concentration (0.8 nM) of the Kappa opioid receptor agonist Dynorphin A (FIG. 9A). The agonist activity of Dynorphin A on the KOR is shown in FIG. 9B for comparison.

These results indicate that the effects of these ligands are mediated through activation of mu-opioid receptors and that the compounds are selective for mu, over delta and kappa, opioid receptors.

Example 6: Probe Specificity

Opioid receptor tolerance, and eventual dependence, is thought to result from prolonged exposure to opiates. This results in changes in cell function leading to the requirement for increased doses of agonist to mediate the same analgesic effect. This being the case, one therapeutic utility of the allosteric modulators disclosed herein is their ability to modulate the activity of non-endogenous agonists. Using this approach, a lower dose of a given exogenous opioid (e.g., oxycodone, fentanyl), in the presence of a MOR PAM, will provide an analgesic effect that is equivalent to that obtained by the use of a higher concentration of the same probe in the absence of the MOR PAM. This allows use of a lower dose of opioid to achieve the desired therapeutic effect; thereby affording a higher therapeutic index for patients in the clinical setting. By allowing the use of lower doses of opioid; therapeutic use of an opioid/MOR PAM combination is likely to retard or eliminate the development of tolerance, as well as reducing gastrointestinal distress, respiratory depression and other undesired effects of opioid use.

To test the specificity of MOR PAMs with respect to different non-endogenous MOR ligands ("probe specificity"), concentration response curves (CRCs) to identify the maximal response and $EC_{50}$ concentrations for the β-arrestin and cAMP responses of the OPRM1 receptor to fentanyl, morphine and oxycodone were performed and compared with the responses to EM1. The results are provided in Table 19.

TABLE 19

Signal-dependent $EC_{50}$ and maximum response determinations for different MOR ligands

| Probe | Assay | $EC_{50}$ (μM) | % Max. Resp. |
|---|---|---|---|
| EM-1 | β-arrestin | 0.066471 | 95.649 |
| EM-1 | cAMP | 0.0017686 | 109.9 |
| fentanyl | β-arrestin | 0.063364 | 102.19 |
| fentanyl | cAMP | 0.0029302 | 103.15 |
| morphine | β-arrestin | 0.34612 | 104.65 |
| morphine | cAMP | 0.052858 | 109.28 |
| oxycodone | β-arrestin | 2.3956 | 102.03 |
| oxycodone | cAMP | 0.078278 | 100.62 |

The data in Table 19 was used to determine $EC_{20}$ concentration of fentanyl, morphine, oxycodone and EM1 for activation of the MOR, as measured by β-arrestin recruitment and adenylyl cyclase inhibition. CRCs for various test compounds using $EC_{20}$ concentrations of fentanyl, morphine and oxycodone as the agonists were then performed and compared to the results when EM1 was used as agonist. Representative data are shown in Tables 20-23.

TABLE 20

Allosteric effects of compounds on $EC_{20}$ morphine agonism of MOR

| Compound | Assay | $RC_{50}$ (μM) | Max. Response |
|---|---|---|---|
| 6 | β-arrestin | 8.25 | 421 |
| 6 | cAMP | 2.96 | 93 |
| 2 | β-arrestin | 9.59 | 156 |
| 2 | cAMP | >25 | 26 |
| 123 | β-arrestin | 14.09 | 59 |
| 123 | cAMP | >25 | 0 |
| 8 | β-arrestin | 7.11 | 487 |
| 8 | cAMP | 2.00 | 44 |
| 9 | β-arrestin | 10.65 | 456 |
| 9 | cAMP | 2.95 | 38 |

TABLE 21

Allosteric effects of compounds on $EC_{20}$ Fentanyl agonism of MOR

| Compound | Assay | $RC_{50}$ (μM) | Max. Response |
|---|---|---|---|
| 6 | β-arrestin | 5.79 | 179 |
| 6 | cAMP | 2.01 | 95 |
| 2 | β-arrestin | >25 | 19 |
| 2 | cAMP | >25 | 0 |
| 123 | β-arrestin | >25 | 0 |
| 123 | cAMP | >25 | 0 |
| 8 | β-arrestin | 14.25 | 146 |
| 8 | cAMP | >25 | 6 |
| 9 | β-arrestin | 13.57 | 83 |
| 9 | cAMP | >25 | 0 |

TABLE 22

Allosteric effects of compounds on $EC_{20}$ Oxycodone agonism of MOR

| Compound | Assay | $RC_{50}$ (μM) | Max. Response |
|---|---|---|---|
| 6 | β-arrestin | 4.83 | 384 |
| 6 | cAMP | 0.32 | 90 |
| 2 | β-arrestin | 13.56 | 126 |
| 2 | cAMP | >25 | 5 |
| 123 | β-arrestin | >25 | 17 |
| 123 | cAMP | >25 | 0 |
| 8 | β-arrestin | 12.94 | 343 |
| 8 | cAMP | 1.91 | 56 |
| 9 | β-arrestin | 11.09 | 296 |
| 9 | cAMP | 3.18 | 40 |

TABLE 23

Allosteric effects of compounds on $EC_{20}$ EM-1 agonism of MOR

| Compound | Assay | $RC_{50}$ (μM) | Max. Response |
|---|---|---|---|
| 6 | β-arrestin | 2.52 | 173 |
| 6 | cAMP | 0.50 | 93 |
| 2 | β-arrestin | 0.36 | 143 |
| 2 | cAMP | 0.57 | 81 |
| 123 | β-arrestin | 1.02 | 190 |
| 123 | cAMP | 0.59 | 43 |
| 8 | β-arrestin | 0.33 | 213 |
| 8 | cAMP | 0.84 | 76 |
| 9 | β-arrestin | 0.36 | 210 |
| 9 | cAMP | 0.59 | 75 |

As shown in Tables 21 and 23, most compounds displayed high selectivity for the endogenous peptide EM1 over the non-endogenous synthetic opioid fentanyl as determined by either β-arrestin or cAMP readouts. Of particular interest is the probe dependency observed when comparing the effects of identical allosteric modulators on the non-endogenous opium-based ligands morphine and oxycodone (Tables 20 and 22). These data provide support for the proposition that the PAMs disclosed herein can be used for the selective activation of the MOR using a variety of non-endogenous ligands for therapeutic use. The results provided in Tables 20-23 provide direct evidence for ligand-dependent probe specific PAM activity; and thus provide a basis for the use of lower doses of opioids, in combination with a probe-dependent PAM, to discriminate between the therapeutic analgesic properties of opioids, and their tolerance and dependence liabilities. Moreover, the high level of specificity displayed for the endogenous OR agonist EM1 over the non-endogenous probes indicates a low potential for abuse of EM1-specific MOR PAMs.

Example 7: Selective Signaling Bias

The ability of the MOR PAMs disclosed herein to provide positive allosteric modulation of the activity of exogenous opioids indicates that MOR PAMs can be used, in combination with exogenous opioids, to provide analgesia with a reduced probability of the development of tolerance. An additional benefit would be realized if MOR PAMs also had differential effects of the various downstream processes induced by receptor activation; some of which contribute to the side effects of opioid use. Therefore, MOR PAMs that are able to bias the response to an orthosteric agonist away from signaling pathways that mediate tolerance, dependence and other unwanted effects, in favor of signaling pathways that mediate a therapeutic response, would be desirable.

Figure 10A:
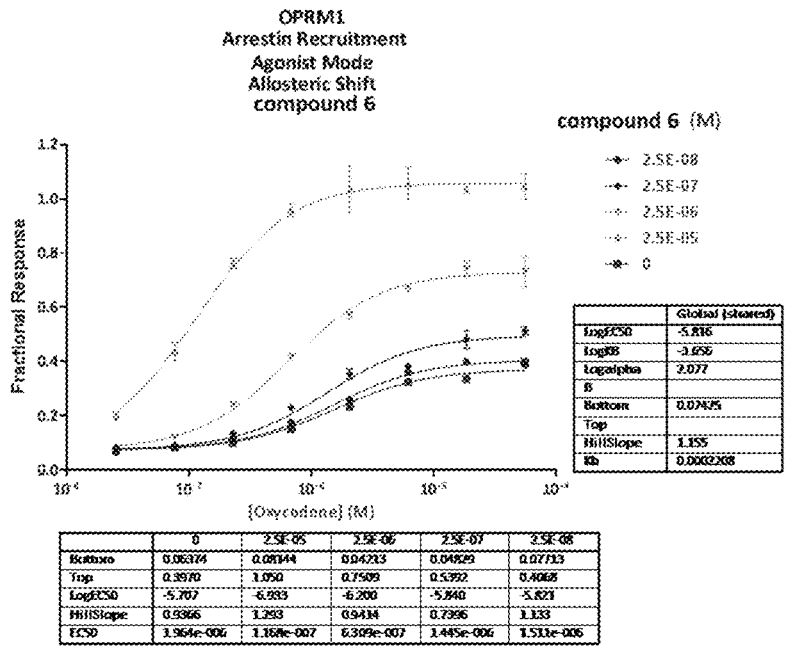
FIG. 10A is a concentration response curve showing the effect of increasing concentrations of compound 6 on oxycodone-induced β-arrestin recruitment by the MOR.
Figure 10B:
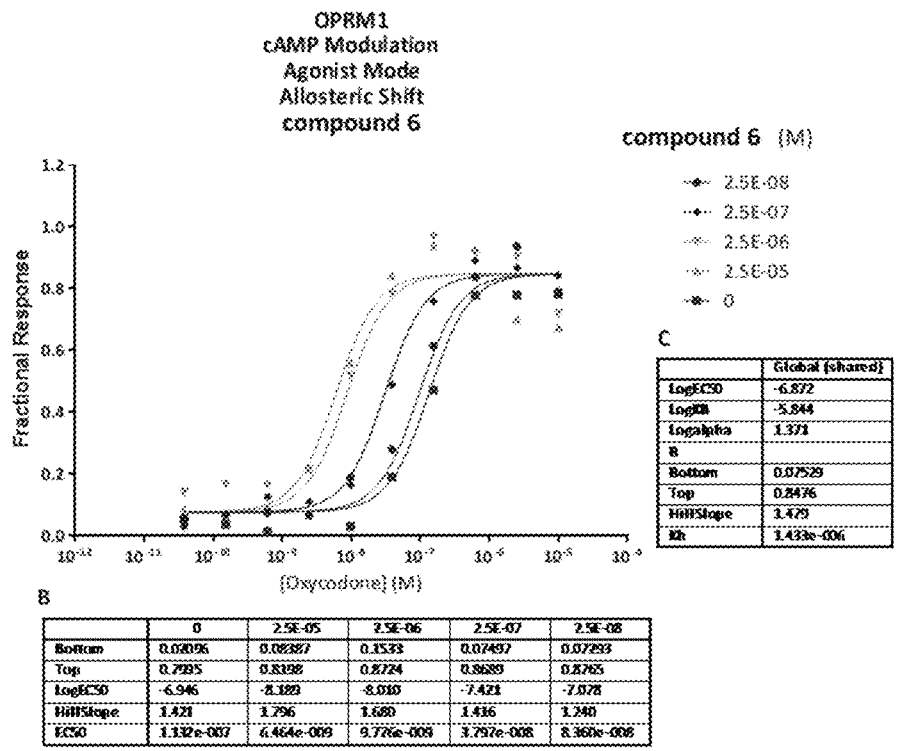
FIG. 10B is a concentration response curve showing the effect of increasing concentrations of compound 6 on oxycodone-induced adenylyl cyclase inhibition by the MOR.

Accordingly, concentration-response curves (CRCs) for oxycodone-mediated recruitment of β-arrestin and oxycodone-mediated adenylyl cyclase inhibition were generated in the absence or presence of varying concentrations of compound 6. The full functional allosteric model for response was applied to analyze the results. Kenakin (2005), supra; Price et al., supra; Ehlert, supra. This model estimates the equilibrium dissociation constant of the modulator ($K_B$), the cooperative effect of the modulator on agonist affinity ($\alpha$) and cooperative effect of the modulator on agonist efficacy ($\beta$). Compound 6 produced concentration-dependent and saturable leftward shifts in the potency of oxycodone for both β-arrestin recruitment (FIG. 10A) and adenylyl cyclase inhibition (FIG. 10B). With respect to the β-arrestin signaling bias, Compound 6 increased the affinity ($\alpha$) of oxycodone by a factor of 2 and increased the efficacy ($\beta$) of oxycodone by a factor of 80. With respect to the cAMP signaling bias, compound 6 increased the affinity ($\alpha$) of oxycodone by a factor of 4 and increased the efficacy ($\beta$) of oxycodone by a factor of 4. This results in an effective potency for PAM effect with respect to the cAMP signal of 234 nM.

Example 8: Pharmacokinetics

Figure 11A:
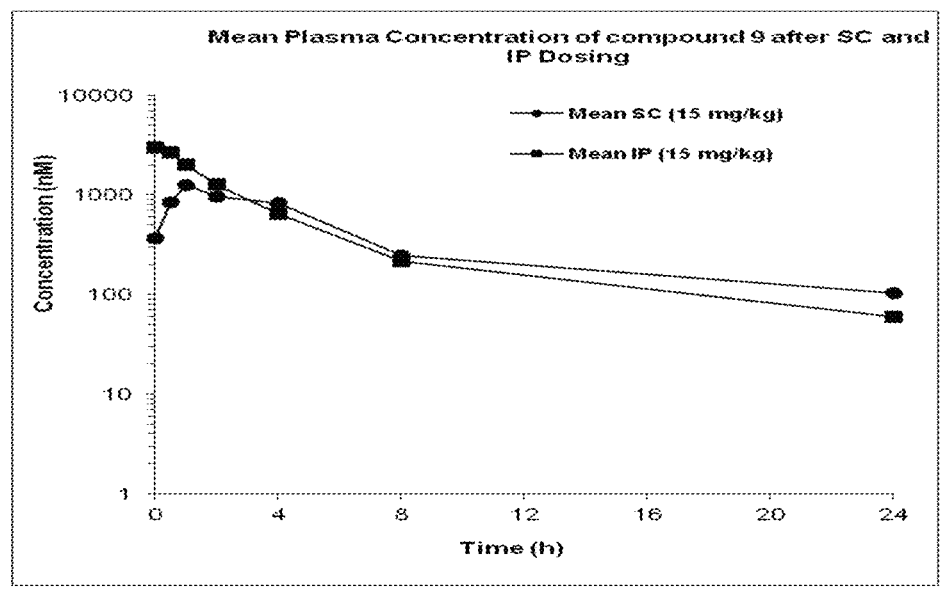
FIG. 11A shows a time-course of plasma concentration of compound 9 in CD-1 mice (n=2) after either subcutaneous (SC) or intraperitoneal (IP) administration of 15 mg/kg of compound 9.

To be useful as a therapeutic, a MOR PAM must not only be able to activate endogenous and non-endogenous orthosteric ligands of the MOR, it must also persist in the body in concentrations sufficient to exert its allosteric effect. To test intracorporeal persistence, murine models were chosen, based on the preponderance of data available linking endogenous opioids to analgesic mechanisms. Compound 9 (Table 10) was formulated for dosing in CD-1 mice. Two mice per group were tested and each group was administered 15 mg/kg of the compound. Concentrations of the compound were measured by mass spectrometry of blood samples. Compound 9 was found to have exposures and an half-life appropriate for in vivo studies using either intraparential or subcutaneous dosing (FIG. 11A).

Figure 11B:
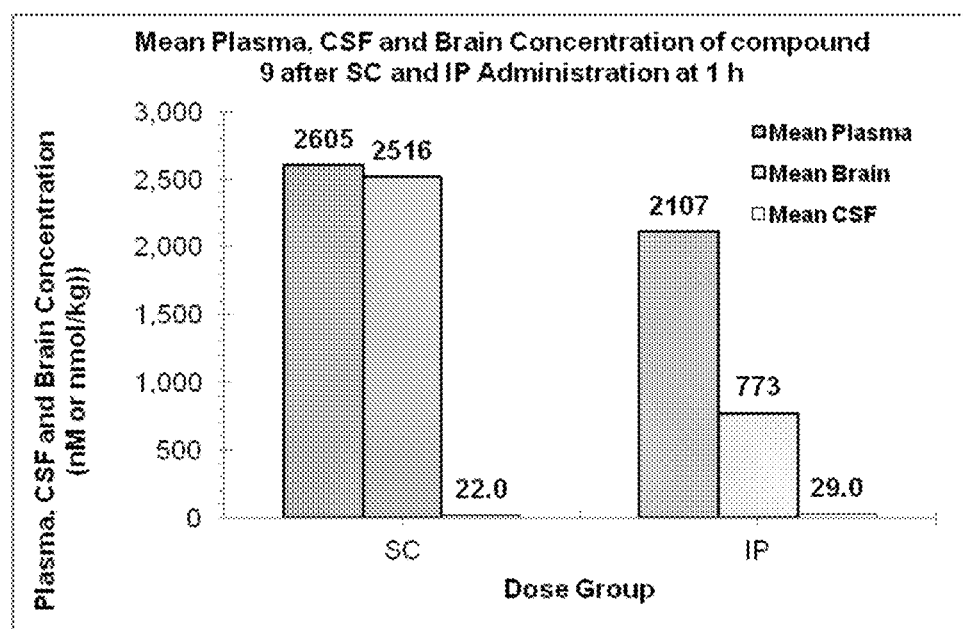
FIG. 11B shows mean (n=2) concentrations of compound 9 in plasma, brain and cerebrospinal fluid (CSF); one hour after administration of 15 mg/kg of compound 9 to CD-1 mice by subcutaneous (SC) or intraparietal (IP) injection. Concentrations of compound 9 were measured by mass spectroscopy.

Given that opioid receptors are highly concentrated in the dorsal root ganglion (DRG) and brain (Martin-Schild et al., supra), terminal pharmacokinetic studies were performed to verify the concentration in the plasma, cerebrospinal fluid and brain. FIG. 11B shows that compound 9 persists in brain and plasma, at therapeutically relevant concentrations, one hour after either subcutaneous or intraperitoneal administration. These results indicate, for the first time, that a MOR PAM can persist at $EC_{50}$ concentrations within a live animal, thereby justifying further in vivo studies. (See Table 23, which shows that, for EM1-mediated MOR agonism, the $RC_{50}$ of compound 9 for β-arrestin recruitment is 360 nM and the $RC_{50}$ of compound 9 for adenylyl cyclase inhibition is 590 nM.)

Figure 11C:
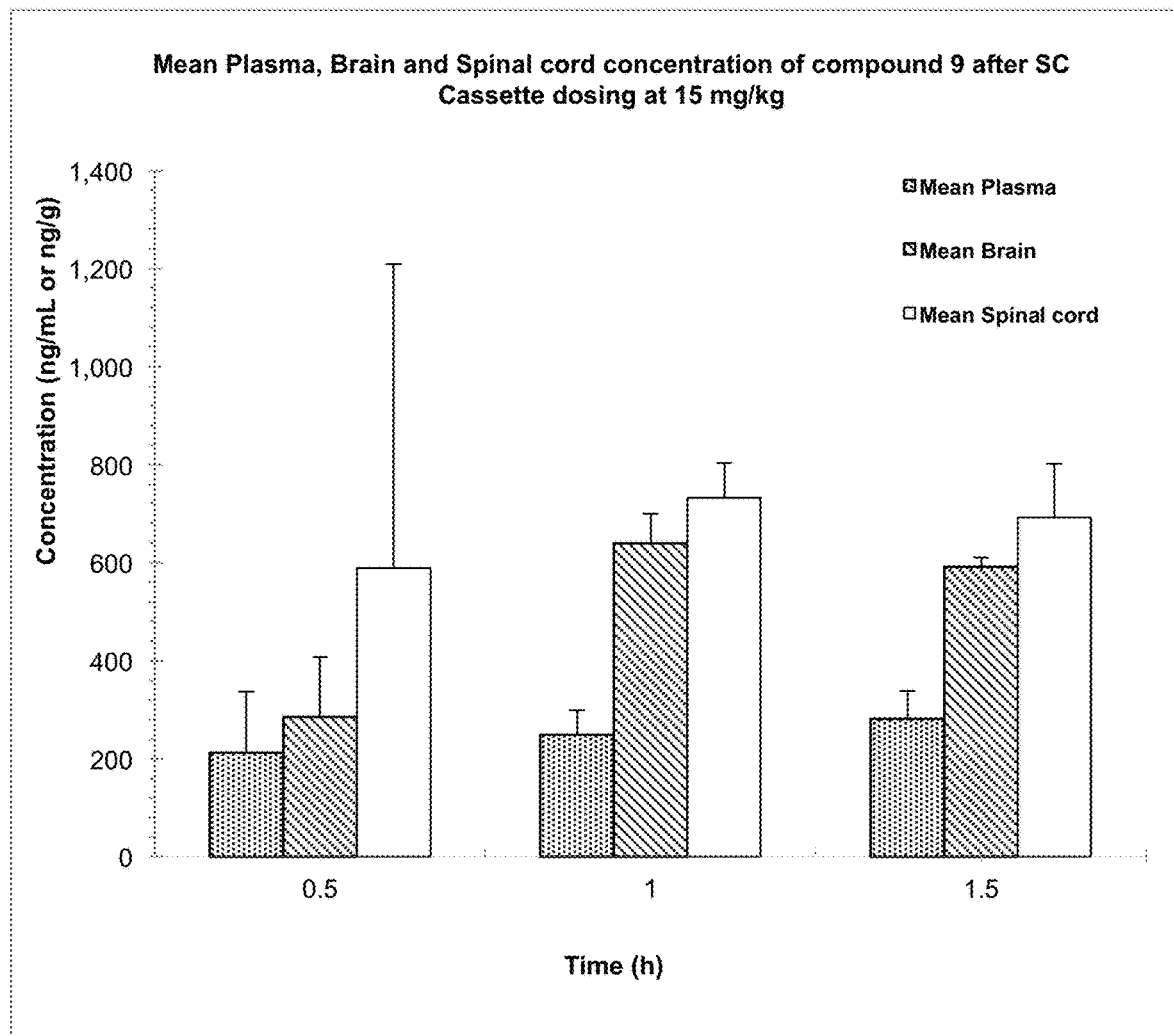
FIG. 11C shows mean (n=3) concentrations of compound 9 in plasma, brain and spinal cord of ICR rats; at different times (0.5, 1.0 and 1.5 hours) after subcutaneous injection of 15 mg/kg of the compound. Concentrations of compound 9 were measured by mass spectroscopy.

Concentrations of subcutaneously injected compound 9 in spinal tissue (where the DRG are located) were also assessed. Compound 9 was formulated for subcutaneous dosing in ICR rats and was found to exhibit good exposures in spinal tissue (which contains the DRG) and brain, indicating coverage of the $EC_{50}$ in both relevant tissues (FIG. 11C).

Example 9: Augmentation of Anti-Nociceptive Effect of EM1 by a MOR PAM

An acute pain model was used to determine the analgesic effect of a MOR PAM administered by itself (i.e., in the absence of exogenous opioid). This approach avoids the complexity of matching the pharmacokinetic profile of endomorphin release in response to a pain-inducing insult with a (1) particular MOR PAM (to account for basal endomorphin analgesis) and (2) the measurement window of the study, as would be required for a chronic pain study. Accordingly, an acute pain model, in which the pharmacodynamic measurement was performed directly after the insult, was employed. This was expected to isolate the low basal levels of EM1 analgesis that existed prior to the insult, thereby eliminating the contribution of the time course of release of endogenous opioids in response to the insult. Mousa et al., supra.

The warm water tail-flick assay was chosen as the acute pain model for the reasons described above. Exogenously applied EM1 has been shown to display potent analgesic effects in this model. Przewlocka et al., (1999), supra. First, minimum and sub-efficacious dose of EM1, applied via intrathecal injection to rats, were identified. The values obtained for the minimum (3 ug/kg) and sub-efficacious dose of EM1 (1 ug/kg) are in agreement with those found in the literature. Horvath (2000), supra. In addition, the time required for maximal response to an intrathecal injection of EM1 to be observed, as well as the time required for a return to basal levels of antinociception, were determined and likewise found to be in agreement with those found in the literature.

Figure 12A:
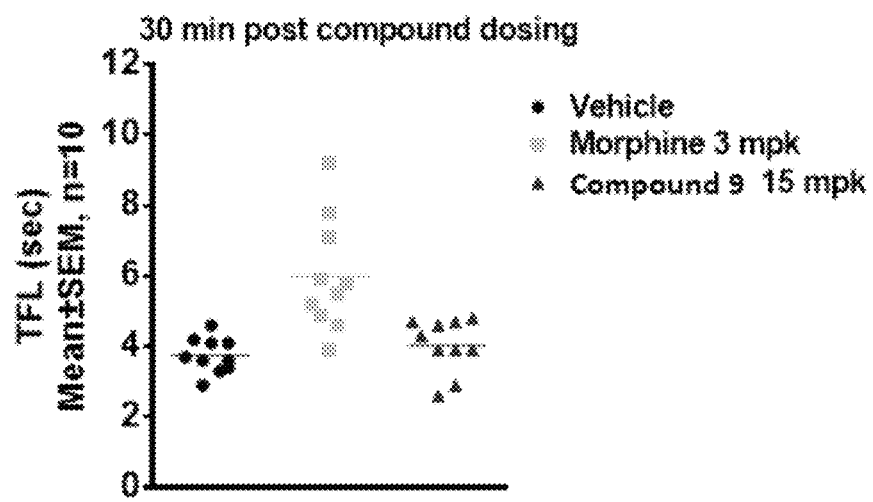
FIG. 12A shows effect of compound 9 on the tail-flick response in CD1 mice in the absence of added exogenous EM-1 (triangles). The effect of morphine is also shown (squares). Tail flick latency was measured 30 minutes after subcutaneous introduction of either compound 9 or morphine. Injection of an equal volume of vehicle was used as a negative control (circles).

To verify the lack of antinociceptive effects of compound 9 when only basal EM1 is present, subcutaneous injections (15 mg/kg) of the compound were administered to CD1 mice (n=10) and tail-flick latency (TFL) was assayed 30 minutes after dosing. No antinociceptive effects were observed 30 minutes after dosing (FIG. 12A).

Figure 12B:
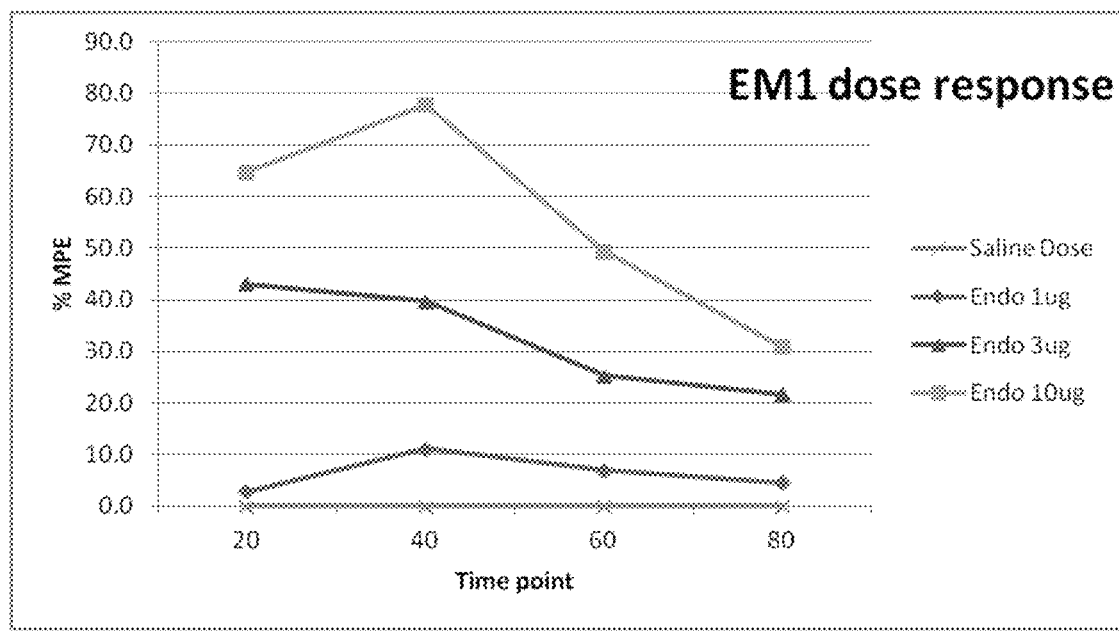
FIG. 12B shows a time-course of the effect of added exogenous endomorphin-1 (Endo) on the tail-flick response in ICR rats. Three doses of EM-1 were introduced by intrathecal injection: 1 µg (diamonds), 3 µg (triangles) and 10 µg (squares); and an equal volume of saline (x) was injected as a negative control.
Figure 12C:
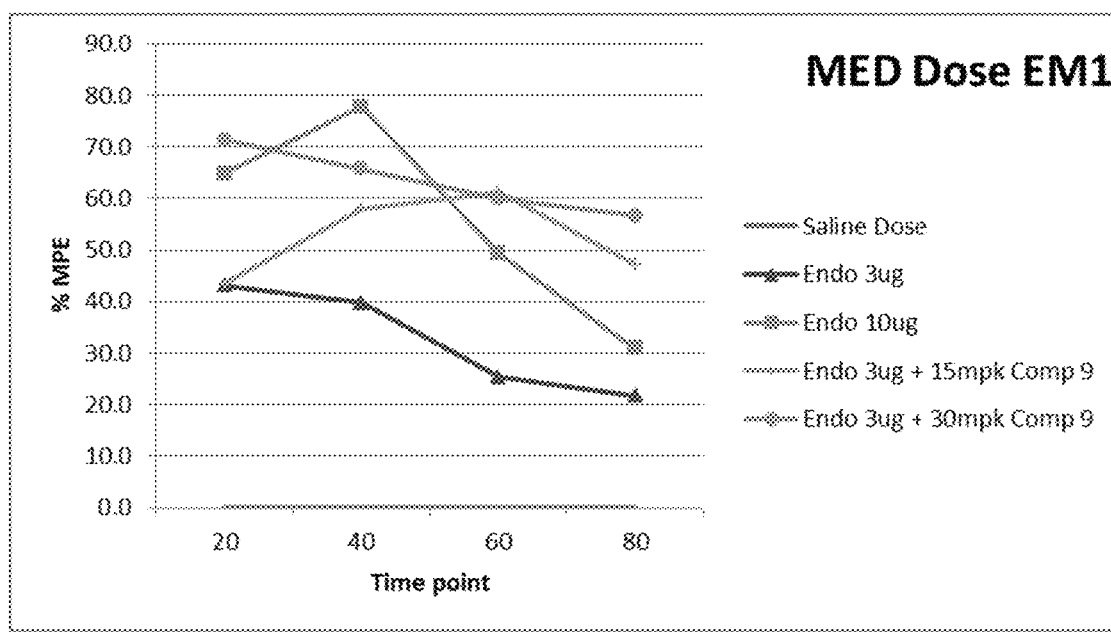
FIG. 12C shows a time course of the effect of two concentrations of subcutaneously administered compound 9 (15 and 30 mg/kg) on the antinociceptive effect of a minimally efficacious dose of intrathecally administered exogenous EM1 (3 µg, triangles) in the tail-flick assay. Concentrations of compound 9 administered were 15 mg/kg (+) and 30 mg/kg (circles). Also shown are results after administration 10 µg of EM1 (squares) and saline.

In view of its lack of antinociceptive activity on its own, compound 9 was then tested for in vivo MOR-PAM effects in conjunction with exogenously provided EM1 in ICR rats. For these experiments, the delay in tail flick induced by EM1 alone was compared to the delay in tail flick when compound 9 was dosed in ICR-rats in combination with intrathecal administration of minimum and sub-efficacious doses of EM1. Data for the time course antinociceptive effects of varying doses of intrathecally administered EM1 is shown in FIG. 12B. Data for the effects of two doses of compound 9 on the time course antinociceptive effects of a minimally efficacious dose (MED) of EM1 (3 µg) is shown in FIG. 12C. It can be seen that compound 9 potentiates the effect of suboptimal doses of EM-1 in the tail-flick assay; demonstrating that the antinociceptive effects of a minimally efficacious dose of EM1 can be modulated in a dose dependent manner by a small molecule MOR-PAM. This modulation is observed as (a) a shortening of the time required for endomorphin to demonstrate antinocicepive effects, (b) an increase in maximal response observed, and (c) a lengthening of the duration of the response. These effects might be due to any of the following: $T_{on}$[Endomorphin], $K_{Elim}$[Endomorphin], $T_{off}$[Endomorphin], $K_f$[Endomorphin], and possibly additional mechanisms.

An illuminating effect was observed at 80 min after administration, when the EM1 response was waning. Specifically, compound 9 demonstrated a β-effect on endomorphin efficacy (i.e., an increase in maximal response), as was observed in vitro (see FIGS. 7A and 7B). The in vivo effects of compound 9 can be modelled by the in vitro parameters obtained for this PAM (FIGS. 7A and 7B) with considerable similarity. Specifically, while the in vitro β-arrestin endomorphin responses modeled in FIG. 7A yielded an αβ product of 27, the in vivo effects (FIG. 12C) were fit with an αβ product of 31.5.

Figure 12D:
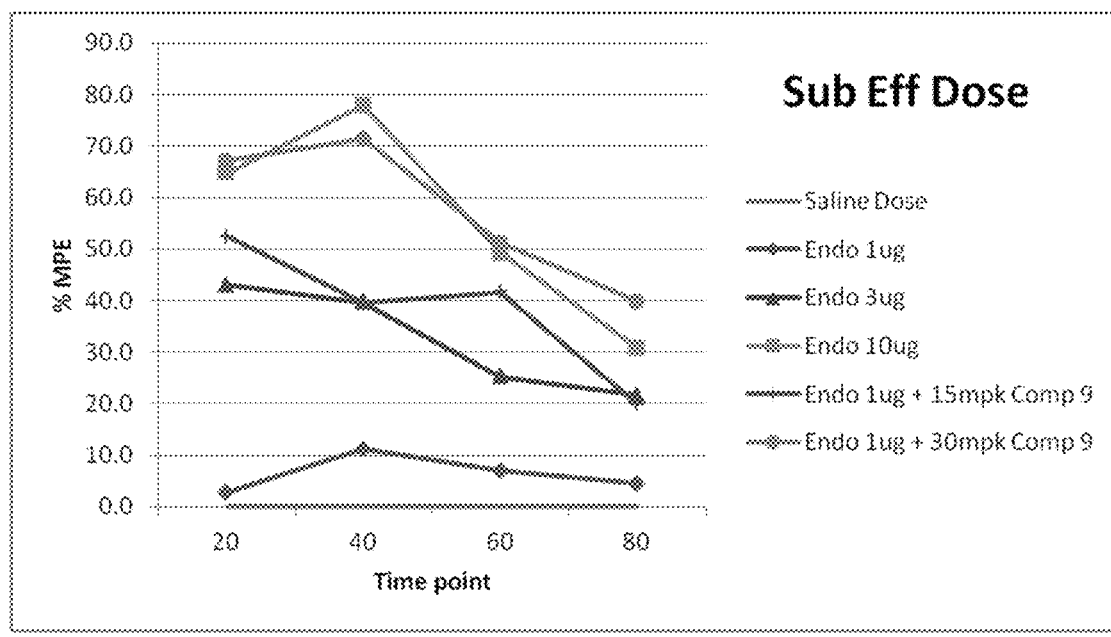
FIG. 12D shows a time course of the effect of two concentrations of subcutaneously administered compound 9

The effect of compound 9 on the antinociceptive activity of a sub-efficacious dose of EM-1 was also assessed. Data for the effects of two doses of compound 9 on the time course antinociceptive effects of a sub-efficacious dose of EM1 (1 µg) is shown in FIG. 12D. The results show that compound 9 also potentiates the effect of sub-efficacious doses of the opioid. These results demonstrate that the anti-nociceptive effects of a sub-efficacious dose of endomorphin-1 can be modulated, in a dose dependent manner, by a small molecule MOR PAM. This modulation is observed as (a) a shortening of the time required for endomorphin-1 to demonstrate its anti-nociceptive effects, (b) an increase in maximal response observed, and (c) an increase in the duration of the response. The ability to rescue a sub-therapeutic dose of the endogenous ligand in a dose- and time-dependent manner with a subtype selective MOR PAM has significant implications for the clinical viability of the use of MOR PAMs in acute and chronic pain settings.

Figure 1A:
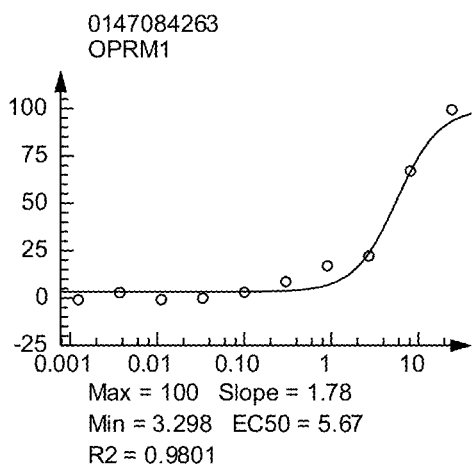
FIG. 1A shows a concentration response curve for Compound 44 in a beta-arrestin recruitment assay using the MOR and an $EC_{20}$ endomorphin-1 concentration of 4.5 nM. The compound exhibits moderate positive allosteric activity for β-arrestin recruitment.
Figure 1B:
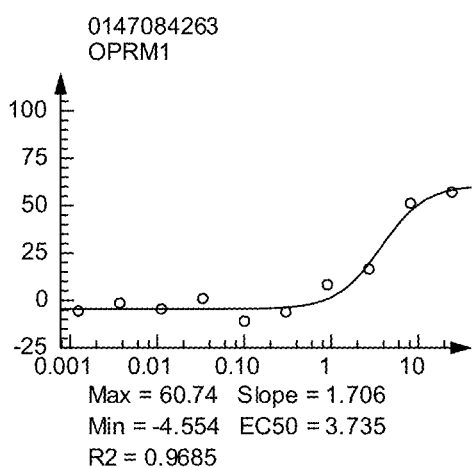
FIG. 1B shows a concentration response curve for Compound 44 in a cAMP signaling assay using the MOR and an $EC_{20}$ endomorphin-1 concentration of 0.45 nM. The compound exhibits moderate positive allosteric activity for cAMP signaling.
Figure 2A:
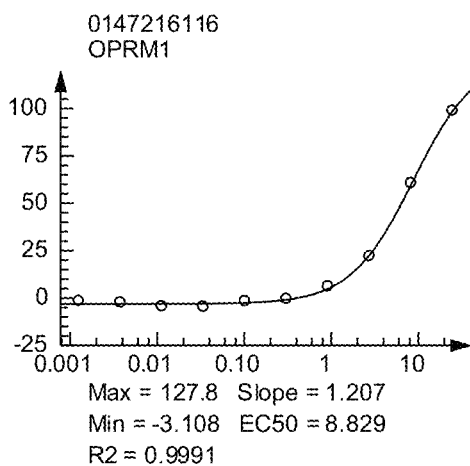
FIG. 2A shows a concentration response curve for Compound 219 in a beta-arrestin recruitment assay using the MOR and an $EC_{20}$ endomorphin-1 concentration of 4.5 nM. The compound exhibits low positive allosteric activity for β-arrestin recruitment.
Figure 2B:
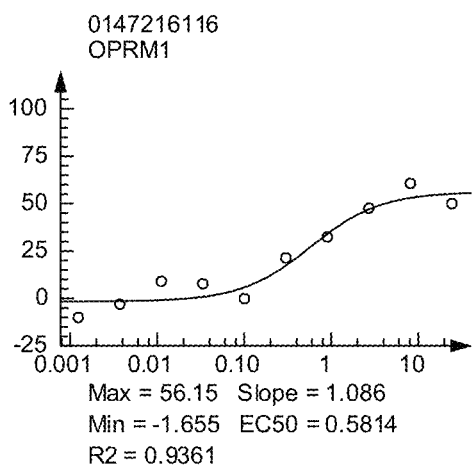
FIG. 2B shows a concentration response curve for Compound 219 in a cAMP signaling assay using the MOR and an $EC_{20}$ endomorphin-1 concentration of 0.45 nM. The compound exhibits high positive allosteric activity for cAMP signaling.
Figure 3A:
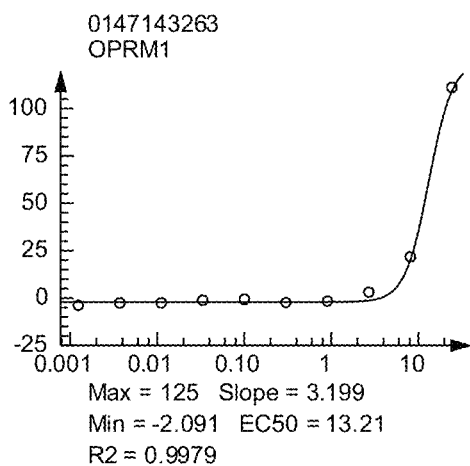
FIG. 3A shows a concentration response curve for Compound 14 in a beta-arrestin recruitment assay using the MOR and an $EC_{20}$ endomorphin-1 concentration of 4.5 nM. The compound exhibits silent allosteric activity for β-arrestin recruitment.
Figure 3B:
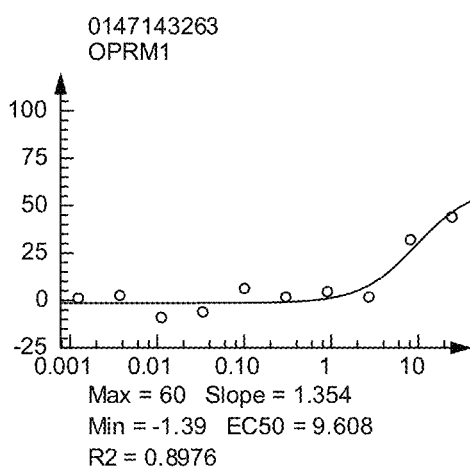
FIG. 3B shows a concentration response curve for Compound 14 in a cAMP signaling assay using the MOR and an $EC_{20}$ endomorphin-1 concentration of 0.45 nM. The compound exhibits silent allosteric activity for cAMP signaling.
Figure 4A:
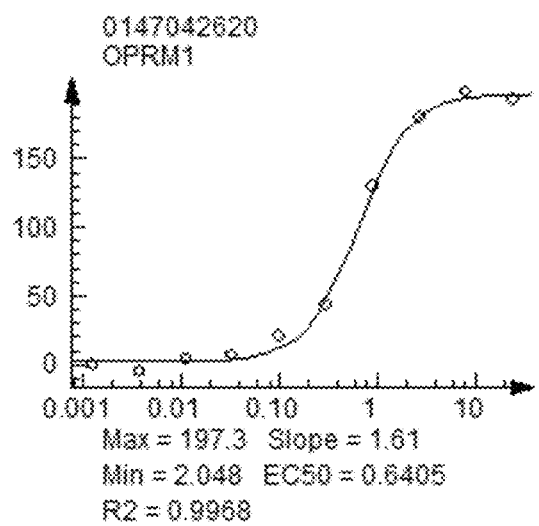
FIG. 4A shows a concentration response curve for Compound 216 in a beta-arrestin recruitment assay using the MOR and an $EC_{20}$ endomorphin-1 concentration of 4.5 nM. The compound exhibits high positive allosteric activity for β-arrestin recruitment.
Figure 4B:
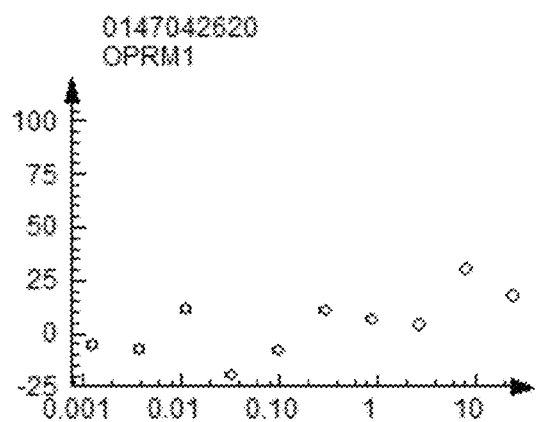
FIG. 4B shows a concentration response curve for Compound 216 in a cAMP signaling assay using the MOR and 4 an $EC_{20}$ endomorphin-1 concentration of 0.45 nM. The compound exhibits silent allosteric activity for cAMP signaling.
Figure 5A:
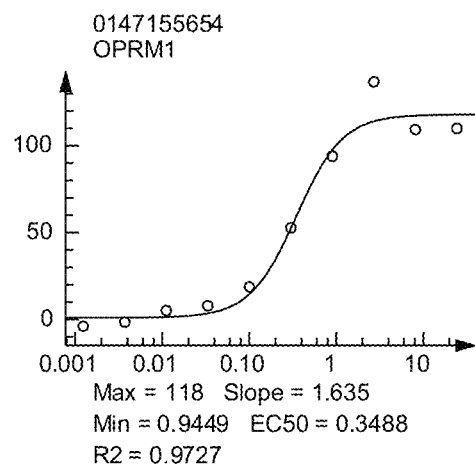
FIG. 5A shows a concentration response curve for Compound 2 in a beta-arrestin recruitment assay using the MOR and an $EC_{20}$ endomorphin-1 concentration of 4.5 nM. The compound exhibits high positive allosteric activity for β-arrestin recruitment.
Figure 5B:
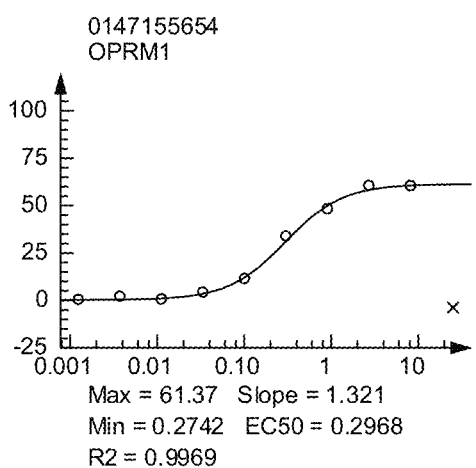
FIG. 5B shows a concentration response curve for Compound 2 in a cAMP signaling assay using the MOR and an $EC_{20}$ endomorphin-1 concentration of 0.45 nM. The compound exhibits high positive allosteric activity for cAMP signaling.
Figure 6A:
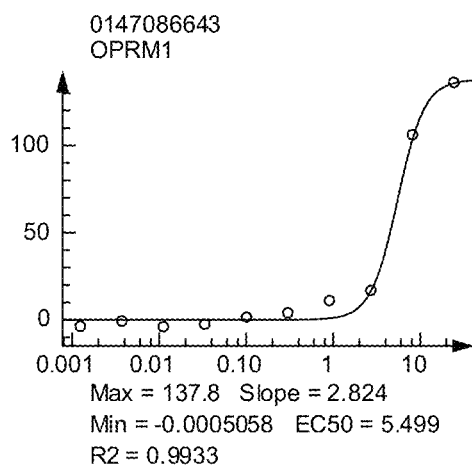
FIG. 6A is a concentration response curve for Compound 108 in a beta-arrestin recruitment assay using the MOR and an $EC_{20}$ concentration of 4.5 nM endomorphin-1. The compound exhibits a moderate positive allosteric effect on EM1 agonism of the MOR.
Figure 6B:
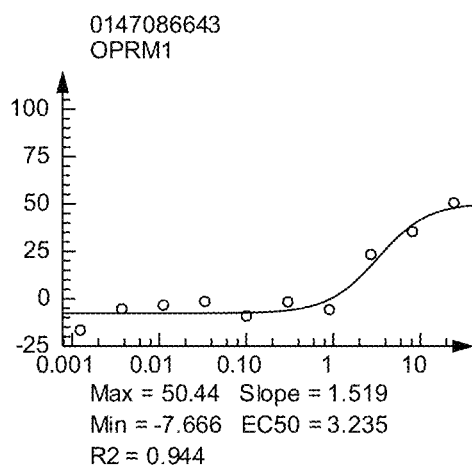
FIG. 6B is a concentration response curve for Compound 108 in a cAMP signaling assay using the MOR and an $EC_{20}$ concentration of 0.45 nM endomorphin-1. The compound exhibits a moderate positive allosteric effect on EM1 agonism of the MOR.
Figure 6C:
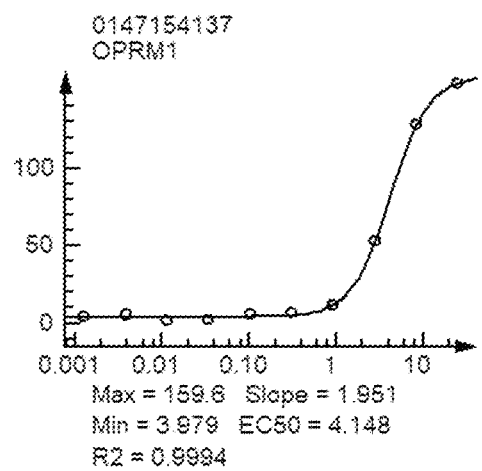
FIG. 6C is a concentration response curve for Compound 177 in a beta-arrestin recruitment assay using the MOR and an $EC_{20}$ concentration of 4.5 nM endomorphin-1. The compound exhibits a moderate positive allosteric effect on EM1 agonism of the MOR.
Figure 6D:
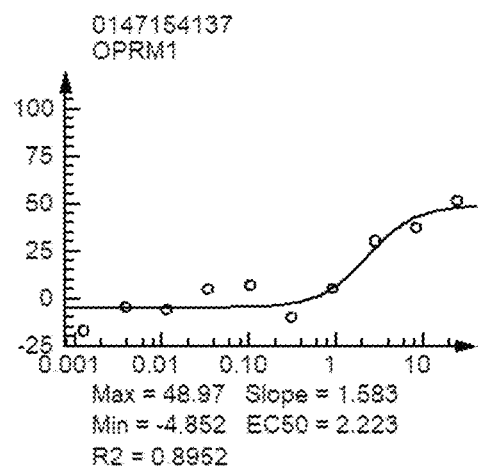
FIG. 6D is a concentration response curve for Compound 177 in a cAMP signaling assay using the MOR and an $EC_{20}$ concentration of 0.45 nM endomorphin-1. The compound exhibits a moderate positive allosteric effect on EM1 agonism of the MOR.
Figure 6E:
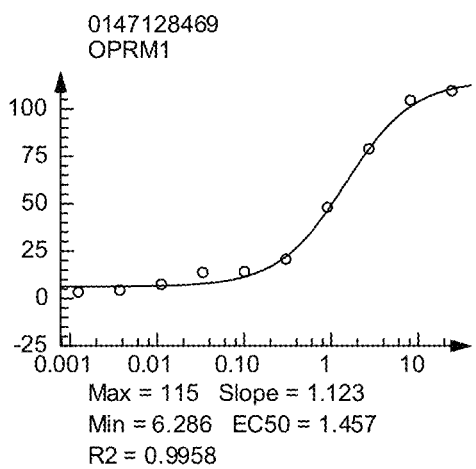
FIG. 6E is a concentration response curve for Compound 6 in a beta-arrestin recruitment assay using the MOR and an $EC_{20}$ concentration of 4.5 nM endomorphin-1. The compound exhibits a moderate positive allosteric effect on EM1 agonism of the MOR.
Figure 6F:
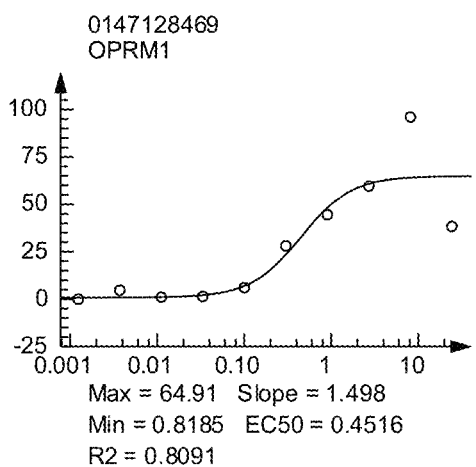
FIG. 6F is a concentration response curve for Compound 6 in a cAMP signaling assay using the MOR and an $EC_{20}$ concentration of 0.45 nM endomorphin-1. The compound exhibits a moderate positive allosteric effect on EM1 agonism of the MOR.
Figure 6G:
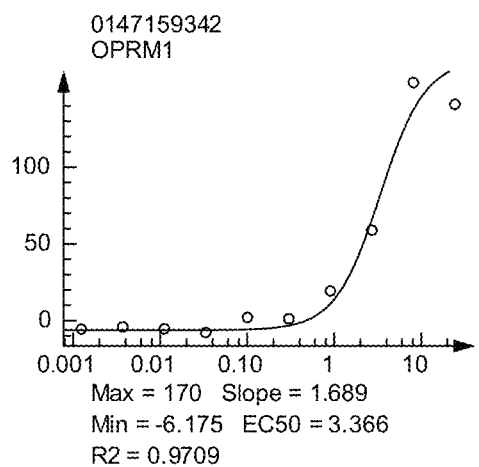
FIG. 6G is a concentration response curve for Compound 110 in a beta-arrestin recruitment assay using the MOR and an $EC_{20}$ concentration of 4.5 nM endomorphin-1. The compound exhibits a moderate positive allosteric effect on EM1 agonism of the MOR.
Figure 6H:
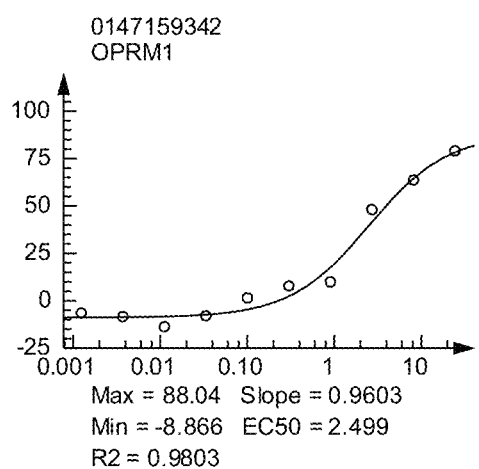
FIG. 6H is a concentration response curve for Compound 110 in a cAMP signaling assay using the MOR and an $EC_{20}$ concentration of 0.45 nM endomorphin-1. The compound exhibits a moderate positive allosteric effect on EM1 agonism of the MOR.
Figure 6I:
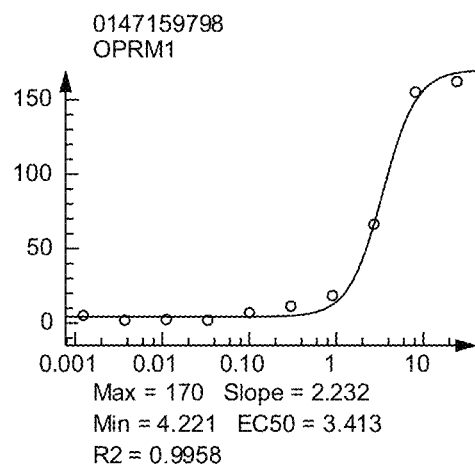
FIG. 6I is a concentration response curve for Compound 109 in a beta-arrestin recruitment assay using the MOR and an $EC_{20}$ concentration of 4.5 nM endomorphin-1. The compound exhibits a moderate positive allosteric effect on EM1 agonism of the MOR.
Figure 6J:
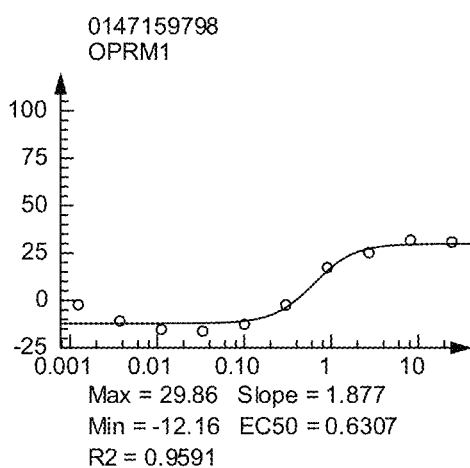
FIG. 6J is a concentration response curve for Compound 109 in a cAMP signaling assay using the MOR and an $EC_{20}$ concentration of 0.45 nM endomorphin-1. The compound exhibits a moderate positive allosteric effect on EM1 agonism of the MOR.
Figure 7A:
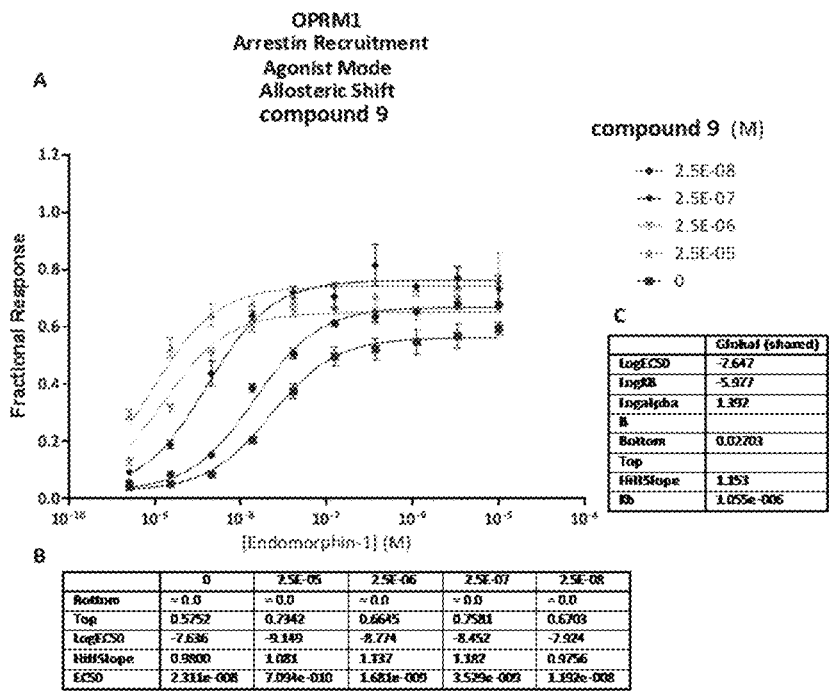
FIG. 7A shows concentration response curves (CRCs) for the effect of compound 9 on oxycodone-induced β-arrestin recruitment.
Figure 7B:
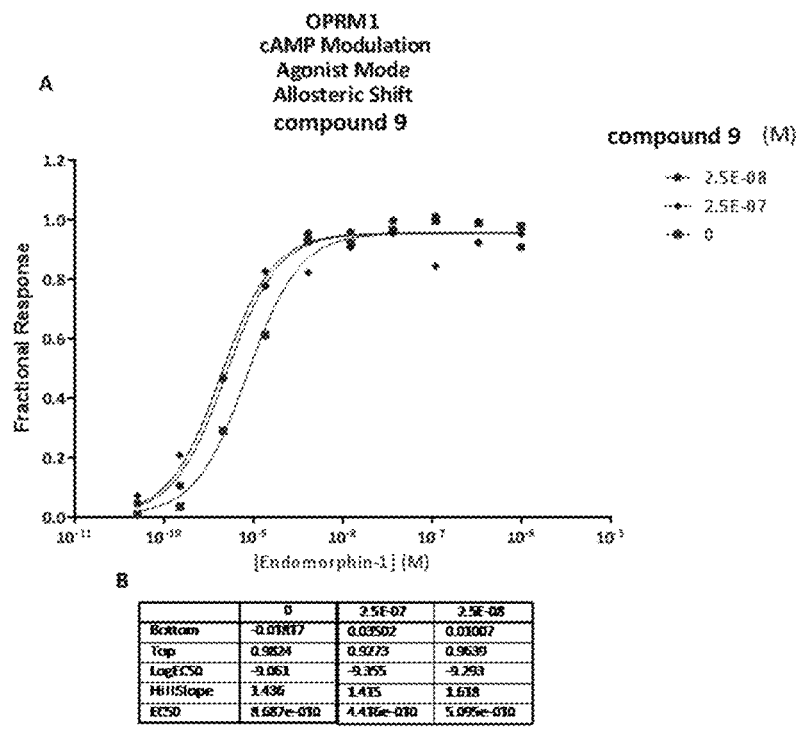
FIG. 7B shows concentration response curves (CRCs) for the effect of compound 9 on oxycodone-induced adenylyl cyclase inhibition.

The positive allosteric effects of compound 9 on endomorphin activity are consistent with increased endomorphin efficacy (i.e., an increased β value) induced by compound 9, as was observed in vitro (FIGS. 7A and 7B). This effect is valuable, as discussed previously, in terms of increasing low levels of response. However, the affinity effect (α value) is also significant, since the overall affinity of all PAMs depends on the co-binding ligand and also the magnitude of a. Kenakin (2012) *Brit. J. Pharmacol.* 165:1659-1669. The fact that α is >1 for compound 9 indicates that it will bind the MOR with reasonably high affinity in the brain in the presence of endomorphin. This is due to the reciprocal effect of allosteric energy, i.e. as compound 9 increases the affinity of EM1, so too does EM1 increase the affinity of the receptor for compound 9. The positive β effects of compound 9 may be especially beneficial as PAM-induced changes in efficacy have been shown to be uniquely powerful.

Example 10: Activity Switching

It has been observed that allosteric modulators of GPCRs can often exhibit "activity switching" within a chemical series: this occurs when minor modifications to its chemical structure change a compound from a PAM to a negative (NAM) or silent (SAM) allosteric modulator. The loss of observed PAM efficacy that accompanies activity switching may be due to loss of binding affinity, or functional switching from PAMs to NAMs or SAMs. Examples are provided in Table 24.

TABLE 24

Activity switching by MOR PAMs*

| No. | β-arrestin EC$_{50}$ | β-arrestin Max Response | cAMP EC$_{50}$ | cAMP Max Resp. |
|---|---|---|---|---|
| 18 | C | F | C | D |
| 55 | C | F | C | D |
| 57 | C | F | C | E |
| 60 | C | F | C | D |
| 63 | C | F | C | E |
| 71 | C | F | C | D |
| 72 | B | F | A | D |
| 73 | C | F | C | D |
| 79 | C | F | C | D |
| 83 | C | D | C | D |

Legend:
The first column provides the compound number (identified elsewhere herein) of the compound tested.
The second column provides EC$_{50}$ values for β-arrestin recruitment;
the third column provides maximal response values for β-arrestin recruitment;
the fourth column provides EC$_{50}$ values for adenylyl cyclase inhibition; and
the fifth column provides maximal response values for adenylyl cyclase inhibition.
EC$_{50}$ values are coded as follows: A represents an EC$_{50}$ <700 nM; B represents an EC$_{50}$ between 700 nM and 2.1 μM; and C represents an EC 50 >2.1 μM.
Maximal response values are coded as follows: D represents a maximal response of <40%; E represents a maximal response of 40-60%; and F represents a maximal response of >60%.

Example 11: Activity of EM1-Specific MOR PAMs on EM2 Activity

As EM1 and EM2 have very similar structures and activities, but have differential concentrations in relevant tissues, it is necessary to assess the activity of EM1-specific MOR PAMS with respect to EM2 activity. Concentration response curves (CRCs) for three exemplary compounds were obtained to identify the maximal response and EC$_{20}$ concentrations for the β-arrestin and cAMP responses to EM1 (see Table 23 above). These assays were then used to assess the effect of these three compounds on EM2 activity. This data is shown in Table 25. As can be seen, the compounds retain potency against EM2 and have higher signal bias compared to EM1 (cf. Table 23, above). Based on these results, the direct correlation between the intensity of EM2 staining and the etiology of CCI-induced neuropathic pain described herein (see, e.g., Example 13) can be modulated using an EM2 MOR PAM.

TABLE 25

Allosteric effects of compounds on EC$_{20}$ EM2 agonism of MOR

| Compound | Assay | RC$_{50}$ (μM) | Max. Response |
|---|---|---|---|
| 6 | β-arrestin | 3.34 | 117 |
| 6 | cAMP | 0.173 | 91 |
| 2 | β-arrestin | 0.61 | 97 |
| 2 | cAMP | 0.10 | 83 |
| 9 | β-arrestin | 0.78 | 138 |
| 9 | cAMP | 0.14 | 80 |

Example 12: Inflammatory Pain

It is known that, upon inflammatory insult, the body traffics MORs from the dorsal root ganglia (DRG) to the site of injury. (Stein & Machelska, supra; (Stein et al. (1993) *Lancet* 342:321-324. Concomitant with this relocalization of MORs, trafficking of endogenous opioid peptides is thought to occur, possibly via leukocytes, in a temporally- and spatially-dependent fashion. (Przewlocki et al. (1992), supra; Rittner et al., supra; Stein et al. (1990) *Proc. Natl. Acad. Sci. USA* 87:5953-5939; Martin-Schild et al., supra. Some of these leukocytes (CD45[+]3E7) have been shown to specifically traffic EM1 and EM2, and are upregulated in inflamed tissue compared to non-inflamed tissue. Mousa et al., supra.

To test the efficacy of MOR-PAMs for relief of inflammatory pain in a murine model, 50-150 μl of Freund's complete adjuvant is introduced into the paw by intraplantar injection; inducing swelling and mechanical hyperalgesia. Subsequent to the establishment of inflammation, 15 mg/kg of a MOR PAM (e.g., compound 9) is introduced into the animal by subcutaneous injection. Prior to administration of the MOR PAM and at various time points thereafter, pain levels are assessed, e.g., by withdrawal of the paw from mechanical pressure, using, for example, a von Frey apparatus or a Randall & Selitto apparatus. See, e.g., Martinov et al. (2013) *J. Vis. Exp.* 82:51212. After administration of the MOR PAM, the pain response is reduced, and is further reduced at succeeding time points.

It has been shown that in an inflammatory setting, additional exogenous stress can release EM1. This has been shown to result in a switching from hyper to hypo algesia in the ipsilateral vs. contralateral paws. Rittner et al., supra. Accordingly, in further tests, after induction of inflammation the rodent is subjected to stress to cause a release of suprabasal EM1 and is administered a MOR PAM (e.g., compound 9). Under these conditions, hypoalgesia is amplified and occurs at lower endogenous stress levels.

In additional experiments, a MOR PAM such as compound 9 is administered prior to mechanical hyperalgesia and pain response is assessed at various times after induction of mechanical hyperalgesia. Pain response is compared to an animal that has been subjected to mechanical hyperalgesia but has not received a prior administration of a MOR PAM. At all times after induction of mechanical hyperalgesia, the animal that received the MOR PAM shows a lower pain response.

Example 13: Neuropathic Pain

Pain arising from peripheral nerve injury is a severe disability and has profound societal impacts. Neuropathic pain (NP) is poorly treated clinically and is an unmet medical need of great societal importance. Williams & Christo (2009) "Pharmacological and interventional treatments for neuropathic pain." In M. Dobretsov, & J. Zhang, Mechanisms of Pain in Peripheral Neuropathy (pp. 295-375). Kerala, India: Research Signpost.

It has been shown in animal models of chronic constrictive injury (CCI) of nerves that the recruitment of opioid-containing leukocytes as well as an increase in MOR density occurs at the site of injury. Vasudeva et al. (2014) PLoS One 9:e90589; Truong et al., supra; Stein & Machelska, supra. Some of the leukocytes that are recruited in response to CCI were shown to traffic endogenous opioids. Celik et al. (2016) Brain, Behavior and Immunity 57:227-242. Activation of these leukocytes upon exposure to corticotrophin releasing factor (or other substances), is hypothesized to cause a release of endogenous opioids, which ablates mechanical hyperalgesia normally accompanied by neuropathic pain. Labuz et al. (2010) Brain, Behavior and Immunity 24:1045-1053; Celik et al. (2013) Brain, Behavior and Immunity 29:S2-S9. Furthermore, a direct correlation between the intensity of EM2 staining and the etiology of CCI induced neuropathic pain has been shown (Smith et al. (2001) Neuroscience 105:773-778. Additionally, in animal models of neuropathic pain, there is substantial precedent that exogenously applied endogenous opioids have significant effect (Horvath, supra; Przewlocka et al. (1999a), supra.

A number of animal model systems for neuropathic pain exist, including, for example, spinal crushing; Bennett, Xie or Setzler models; chronic constriction injury (CCI); the sciatic nerve crush model; spinal nerve ligation; and laser-induced sciatic nerve injury. See, for example, Jaggi et al. (2009) Fund. & Clin. Pharmacology 25:1-28. To test the efficacy of MOR-PAMs for relief of neuropathic pain, 15 mg/kg of a MOR PAM (e.g., compound 9) is introduced into an animal (e.g., a mouse or a rat) prior to, concurrent with, or subsequent to, induction of neuropathic pain in one or more of these model systems. Administration of the MOR PAM is by subcutaneous injection or orally (e.g., in the animal's food or water). At various time points after administration of the MOR PAM, pain levels are assessed. After administration of the MOR PAM, the pain response is reduced, and is further reduced at succeeding time points.

In additional experiments, animals are subjected to procedures that induce neuropathic pain, and pain response in an animal receiving a MOR PAM is compared to pain response in an animal that has not received a MOR PAM. At all time points, the animal that received the MOR PAM shows a lower pain response.

In further experiments, prophylactic addition of a MOR PAM upon nerve damage delays or ameliorates the onset or intensity of neuropathic pain.

Example 14: Chemotherapy-Induced Neuropathy

Pain arising from chemotherapy (chemotherapy induced neuropathic pain, CINP) is common (for example, it is estimated that 90 to 100% of females receiving cisplatin or paclitaxel for ovarian cancer present symptoms of CINP) and can be a disabling side effect of cancer treatment. In fact, the development of painful neuropathy is often a dose-limiting criterion for oncologic medications. This often leaves the patient with the limited options of either dose reduction or discontinuation of potentially curative or palliative chemotherapeutic agents. Kaley & DeAngelis (2009) Br. J. Haematology 145:3-14; Williams & Christo, supra. CINP incidence and severity are directly related to dose, number of treatment cycles, duration of treatment, etc.

In animal models of CINP, it has been shown that the administration of exogenous EM-1 and EM-2 at the spinal level results in a stronger analgesic effect than that of morphine. Przewlocka et al. (1999a), supra; Grass et al. (2002) Neurosci. Letts. 324:197-200; Przewlocki et al. (1999b), supra. It has been found that there is a linear correlation between the spinal concentration of EM-2 and the degree of mechanical hyperalgesia observed in an animal model of CINP. Yang et al., supra; (Chen et al. (2015) Neuroscience 286:151-161. It was further found that decreasing levels of EM2-like immunoreactivity was the consequence of DPP4 upregulation, and that the concentration of EM-2, and thus the manifestation of CINP mediated mechanical hyperalgesia, can be halted by the prophylactic addition of a DPP4 inhibitor.

Given the involvement of EM2 in relief of CINP, taken together with the MOR PAM effects on EM2 shown above (Example 11), MOR PAMS are used for the relief of CINP. To this end, 15 mg/kg of a MOR PAM (e.g., compound 9) is introduced into an animal (e.g., a mouse or a rat) prior to, concurrent with, or subsequent to, introduction of a chemotherapeutic agent, in one or more of the model systems described above. Administration of the MOR PAM is by subcutaneous injection or orally (e.g., in the animal's food or water). Control animals do not receive a chemotherapeutic agent; additional controls receive a chemotherapeutic agent, but do not receive a MOR PAM. At various time points after administration of the MOR PAM, pain levels are assessed. After administration of the MOR PAM, the pain response is reduced, and is further reduced at succeeding time points.

A possible contributory mechanism for CINP is the inability of the endogenous opioid system to manage the pain caused by the cytotoxic agent. As such, increasing the levels of endogenous opioids with DPP4 inhibitors and/or increasing the potency and duration of the endogenous opioids may be a preventative method to delay the onset or intensity of CINP. This could alter the dose limiting toxicity observed with many cytotoxic agents, thus relieving patients of the pain associated with the administration of lifesaving medicine. The application of a MOR PAM to coincide with the physiologic peptidase upregulation that accompanies chemotherapy can ablate the mechanical hyperalgesia using the higher than basal levels of the endogenous opioids. Additionally, the use of a MOR PAM in combination with the action of peptidase inhibitors (to increase the concentration of EM1 and EM2), results in mechanical hypoalgesia, delaying or ameliorating the onset or intensity of neuropathic pain.

Example 15: Sexual Dysfunction

Just as hormone and neurotransmitter levels have been shown to have effects on behavior, similar effects have been demonstrated with the endogenous opioids. Thus, in addition to the amelioration of pain, the compositions and methods disclosed herein can also be used to address a variety of additional conditions (e.g., depression, anxiety, etc.) that result from pain and/or stress; by using MOR PAMs to enhance the body's ability to modulate pain and/or stress via the action of endogenous ligands.

One such condition is sexual dysfunction. Research has shown that opioid peptides are involved in the copulatory behavior of male mammals, including humans. The regulatory effect of opioids on sexual behavior is dose-dependent and varies depending on the site of infusion. In humans, acute opioid administration results in an intense euphoria, but long term opioid use is associated with a deterioration of sexual function. Deteriorated sexual function in humans and animals is associated with long term opioid abuse, as evidence by but not limited to increased intromission latency, a reduction in mounting frequency, and reduction in intromission frequency. Different lines of evidence suggest that sexual behavior is a physiological stimulus that releases endogenous opioids with two possible effects: to facilitate subsequent sexual behavior and to enhance the rewarding properties of mating and ejaculation. It has been shown that exogenously administered EM1 has direct effects on the intromission latency, mount and intromission frequency in a murine model. Parra-Gamez et al. (2009) *Physiology and Behavior* 97:98-101. Though intensity of the ejaculatory events could not be quantified, this evidence indicates that sexual behavior and ejaculation can be influenced by the release of endogenous opioids. This adds to a body of evidence that EM1 is involved with the rewarding aspects associated with mating.

In light of the involvement of EM1 in male sexual behavior, MOR PAMs can be used to treat certain types of male sexual dysfunction. To test the effects of MOR-PAMs for relief of sexual dysfunction, 15 mg/kg of a MOR PAM (e.g., compound 9) is introduced into a male or female animal (e.g., a mouse or a rat) prior to, concurrent with, or subsequent to, introduction to a sexually active partner of the opposite gender. Administration of the MOR PAM is by subcutaneous injection or orally (e.g., in the animal's food or water). At various time points after administration of the MOR PAM, intromission latency, mount and intromission frequency are assessed. Animals receiving the MOR PAM have shorter intromission latency, higher mount frequencies and higher intromission frequencies than animals that did not receive a MOR PAM.

Example 16: Gastrointestinal Transit

Inhibition of gastrointestinal transit is a significant side effect associated with opioid treatment of acute and chronic pain. Efforts to generate analgesics that dissociate pain relief from side effects are critical to the advancement of public health. Drug-related side effects affecting bowel function including, for example, constipation, abdominal constriction and diarrhea, can cause a great deal of discomfort and pain.

The GI transit model is designed to identify compounds that produce effects on bowel function and cause inhibition of gut transit. The opioid comparator compound, morphine, is well known to inhibit gastrointestinal function. GI transit is an intestinal transport model measuring the distance traveled through the GI tract by an orally administered charcoal bolus. Opioids, which are known to cause constipation in the clinic, slow the transport of the charcoal bolus.

An experiment was performed to examine the effects of a MOR PAM compound on the rate of GI transit in comparison to negative (vehicle) and positive (morphine) controls. Sprague-Dawley rats were fasted for 18 hrs prior to the start of the study. Morphine (10 mg/kg in saline), compound 9 (15, 30, 60 mg/kg in 5% DMSO:10% cremophor EL:85% $H_2O$) and vehicle (5% DMSO:10% cremophor EL:85% $H_2O$) were administered subcutaneously 1 hour prior to administration of the charcoal suspension. Charcoal and gum arabic were suspended in distilled water at a ratio of 10 grams of charcoal:2.5 grams of gum arabic:100 mL of water. The charcoal suspension was administered by lavage to rats at a dose of 1 mL/100 g of body weight. Twenty minutes after charcoal administration rats were sacrificed and the small intestine was removed. The stomach was weighed before and after flushing with saline and the values recorded. The difference (stomach contents) was calculated. The small intestine was uncoiled and the distance covered by the charcoal was measured and recorded. Percent transit was calculated for each rat using the formula: (distance charcoal travelled/length of intestine)×100.

As shown in FIG. 13, GI transit was significantly decreased by morphine (10 mg/kg). In contrast, GI transit was unchanged following administration of compound 9. As shown in FIG. 14, stomach weight was increased after administration of morphine (10 mg/kg). In contrast, stomach weight was unchanged following administration of the MOR PAM compound 9. These results provide evidence that a MOR PAM (at doses of 15, 30, 60 mg/kg) does not exhibit opioid-like impairment of GI transit.

Example 17: Respiratory Depression

Respiratory depression is a significant side effect associated with opioid treatment of acute and chronic pain. Drug-related overdose deaths are often a function of the respiratory depression which occurs with opioid use. Efforts to generate analgesics that dissociate pain relief from side effects are critical to the advancement of public health. Pulse oximetry has been demonstrated to be a reliable non-invasive method for evaluating respiratory depression. Blood oxygen saturation levels in awake rats are measured and compared, using morphine as a positive control.

An experiment was performed to examine the effects of a MOR PAM compound on oxygen saturation levels in comparison to negative (vehicle) and positive (morphine) controls. After baseline pulse oximetry measurements, Sprague-Dawley rats were dosed sucutaneously with morphine (10 mg/kg in saline), compound 9 (15, 30, 60 mg/kg in 5% DMSO:10% cremophor EL: 85% $H_2O$) or vehicle (5% DMSO:10% cremophor EL: 85% $H_2O$) and examined for 90 minutes. Blood oxygen saturation was assessed in awake rats with the MouseOx oximeter system (Starr Life Sciences, Holliston, Mass.). Up to 5 samples were measured every 5 minutes for 15 minutes prior to dosing and 90 minutes after dosing. Each animal was habituated to the device over several days prior to the study.

As shown in FIG. 15, morphine (10 mg/kg) resulted in a significant reduction in oxygen saturation. In comparison, none of the doses evaluated for the MOR PAM compound 9 resulted in a reduction of oxygen saturation compared to vehicle at any point during the 90 minute evaluation. This indicates that the MOR PAM compound did not induce respiratory depression that is typically associated with opioid compounds such as morphine. This is the first demonstration that an MOR PAM does not cause opioid-like respiratory depression.

What is claimed is:

1. A compound having the formula:

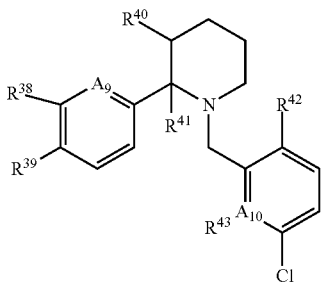

Formula 2 wherein
A9 is CH or N and A10 is C or N;
R38 is Br, Cl, CF$_3$ or OCF$_3$;
R39 is H, Cl or F;
R40 is H or F;
R41 is H or D (deuterium);
R42 is H or F;
R43 is H or F when A10 is C; and
R43 is null when A10 is N.

2. A compound having the formula:

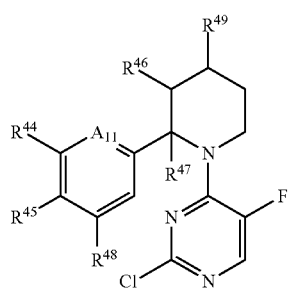

Formula 3 wherein:
A11 is CH or N;
R44 is Cl, Br, F or CF$_3$;
R45 is H, Cl, F or OCF$_3$;
R46 is H or F;
R47 is H or D (deuterium);
R48 is H or F; and
R49 is H, =CH or F.

3. The compound of claim 2, wherein:
A11 is CH;
R44 is CF$_3$;
R45 is H;
R46 is H;
R47 is H;
R48 is H; and
R49 is H.

4. A compound having the formula:

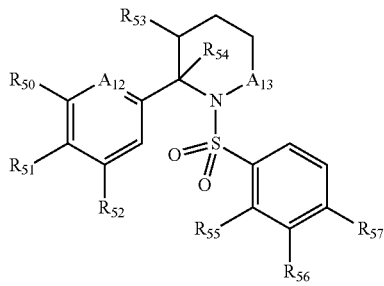

Formula 4 wherein:
A12 is CH or N;
A13 is CH$_2$ or null;
R50 is Cl, Br or CF$_3$;
R51 is H, F or Cl;
R52 is H or F;
R53 is H, F or CH$_3$;
R54 is H or D;
R55 is H or F;
R56 is H or Cl; and
R57 is H or Cl; and
if A13 is null, R53 is F.

5. The compound of claim 2 wherein the compound is a positive allosteric modulator (PAM) of the mu-opioid receptor (a MOR PAM).

6. The compound of claim 5, wherein the compound augments one or more of beta-arrestin-1/2 recruitment, inhibition of adenylate cyclase activity, phosphorylation of ERK1/2 and G-protein activation.

7. The compound of claim 6, wherein the compound possesses selective signal bias for adenylate cyclase inhibition, compared to β-arrestin recruitment.

8. The compound of claim 5, wherein the compound selectively modulates the activity of the mu opioid receptor, compared to the delta, kappa or ORL1 opioid receptors.

9. The compound of claim 5, wherein the compound is an endomorphin-1-dependent or an endomorphin-2-dependent positive modulator of MOR activity.

10. A method for treating pain in a subject in need thereof, the method comprising administering to the subject a compound of claim 5.

11. A method for treating pain in a subject in need thereof, the method comprising administering to the subject:
(a) a compound of claim 5, and
(b) an orthosteric agonist of an opioid receptor.

12. The method of claim 11, wherein the opioid receptor is the mu opioid receptor (MOR).

13. The method of claim 12, wherein the orthosteric agonist is endomorphin-1.

14. A method for potentiating the effect of an exogenous opioid in a subject, the method comprising:
co-administering to the subject, with the exogenous opioid, a MOR PAM according to claim 5.

15. The method of claim 14, wherein the MOR PAM is administered at the same time as the exogenous opioid.

16. A method for reducing the side effect of an exogenous opioid in a subject, the method comprising:
co-administering to the subject, with the exogenous opioid, a MOR PAM according to claim 5.

17. The method of claim 16, wherein a sub-therapeutic dose of the exogenous opioid is administered.

18. The method of claim 16, wherein the MOR PAM possesses selective signal bias for adenylate cyclase inhibition, compared to β-arrestin recruitment.

19. A pharmaceutical composition comprising a MOR PAM according to claim 5 and a pharmaceutically acceptable excipient.

20. A compound for use in reducing pain, inducing analgesia, or reducing nociception in a subject, wherein the compound is a MOR PAM according to claim 5.

* * * * *